US008426380B2

(12) United States Patent
Kaspar et al.

(10) Patent No.: US 8,426,380 B2
(45) Date of Patent: Apr. 23, 2013

(54) INHIBITION OF VIRAL GENE EXPRESSION USING SMALL INTERFERING RNA

(75) Inventors: Roger L. Kaspar, Santa Cruz, CA (US);
Heini Ilves, Santa Cruz, CA (US); Attila A. Seyhan, San Jose, CA (US);
Alexander V. Vlassov, Santa Cruz, CA (US); Brian H. Johnston, Scotts Valley, CA (US)

(73) Assignee: Somagenics, Inc., Santa Cruz, CA (US)

( * ) Notice: Subject to any disclaimer, the term of this patent is extended or adjusted under 35 U.S.C. 154(b) by 0 days.

(21) Appl. No.: 13/039,100

(22) Filed: Mar. 2, 2011

(65) Prior Publication Data

US 2011/0269816 A1 Nov. 3, 2011

Related U.S. Application Data

(63) Continuation of application No. 11/444,901, filed on Jun. 1, 2006, now Pat. No. 7,902,351, which is a continuation-in-part of application No. PCT/US2005/032768, filed on Sep. 12, 2005.

(60) Provisional application No. 60/608,574, filed on Sep. 10, 2004.

(51) Int. Cl.
*C12N 15/11* (2006.01)
*C07H 21/04* (2006.01)

(52) U.S. Cl.
USPC ........................................ 514/44 A; 536/24.5

(58) Field of Classification Search ................. 536/24.5; 514/44 A
See application file for complete search history.

(56) References Cited

U.S. PATENT DOCUMENTS

| | | | |
|---|---|---|---|
| 6,001,990 A | 12/1999 | Wands et al. | |
| 6,174,868 B1 | 1/2001 | Anderson et al. | |
| 2003/0143732 A1 | 7/2003 | Fosnaugh et al. | |
| 2003/0175772 A1 | 9/2003 | Wang | |
| 2003/0228597 A1* | 12/2003 | Cowsert et al. | 435/6 |
| 2004/0053875 A1 | 3/2004 | Kreutzer et al. | |
| 2004/0137471 A1* | 7/2004 | Vickers et al. | 435/6 |
| 2004/0209831 A1 | 10/2004 | McSwiggen et al. | |
| 2004/0259247 A1 | 12/2004 | Tuschl et al. | |
| 2005/0164210 A1 | 7/2005 | Mittal et al. | |
| 2005/0186586 A1 | 8/2005 | Zamore et al. | |
| 2006/0142228 A1 | 6/2006 | Ford et al. | |
| 2009/0004739 A1 | 1/2009 | Demura et al. | |
| 2010/0112686 A1 | 5/2010 | Ge et al. | |

FOREIGN PATENT DOCUMENTS

| | | |
|---|---|---|
| JP | 2004-305140 | 11/2004 |
| WO | 03/010180 A1 | 2/2003 |
| WO | WO-03/070750 A2 | 8/2003 |
| WO | 2004029281 | 4/2004 |
| WO | 2005028646 | 3/2005 |
| WO | WO-2006/031901 A2 | 3/2006 |

OTHER PUBLICATIONS

Yu et al., "RNA interference by expression of short-interfering RNAs and hairpin RNAs in mammalian cells" Proc. Natl. Acad. Sci. USA, 99(9):6047-6052 (Apr. 30, 2002).
Yu et al., "Simultaneous Inhibition of GSK3alpha and GSK3beta Using Hairpin siRNA Expression Vectors" Molecular Therapy, 7(2):228-236 (Feb. 2003).
Yokota, Takanori. Gene therapy of virus disease with RNAi, Igaku No Ayumi (Journal of Clinical and Experimental Medicine), Feb. 21, 2004, vol. 208, No. 8, pp. 669-673. (Partial translation attached).
Ohta, Jun, RNAi Ni Kansuru Kisokenkyu To Sono Ouyou (Basic research on and application of RNA interference) Gan To Kagaku Ryouhou (Japanese Journal of Cancer and Chemotherapy) Jun. 2004, vol. 31, No. 6, pp. 827-831. (Partial translation attached).
Simmonds et al. (1994) "Identification of genotypes of hepatitis C virus by sequence comparisons in the core, E1 and NS-5 regions" J. Gen. Virol. 75:1053-1061.
Kalota, et al. Design of antisense oligonucleotides and short interfering RNA duplexes (siRNA) targeted to BCL6 mRNA: towards rational drug development for specific lymphoma subsets. Blood Cells Mol Dis. May-Jun. 2007;38 (3):199-203.
Vickers, et al. Efficient reduction of target RNAs by small interfering RNA and RNase H-dependent antisense agents. A comparative analysis. J Biol Chem. Feb. 28, 2003;278(9):7108-18.
Paddison, et al. Short hairpin RNAs (shRNAs) induce sequence-specific silencing in mammalian cells. Genes Dev. Apr. 15, 2002;16(8):948-58.
Latham, et al. in RNA Interference Technology From Basic Science to Drug Development (Copyright 2005, Ed. Appasani,K), Cambridge University Press, Chapter 10, pp. 153-154.
Birmingham et al., "3' UTR Seed Matches, but Not Overall Identity, are Associated with RNAi Off-Targets," Nature Methods. 3(3):199-204 (2006); Addendum: Nature Methods, 3(6):487 (2006).
Blight et al., "Efficient Initiation of HCV RNA Replication in Cell Culture," Science, 290:1972-1974 (2000).
Bridge et al., "Induction of an Interferon Response by RNAi Vectors in Mammalian Cells," Nature Genetics, 34(3):263-264 (2003).
Brown et al., "Secondary Structure of the 5' Nantranslated Regions of Hepatitis C Virus and Pestivirus Genomic RNAs," Nucleic Acids Research, 20(19):5041-5045 (1992).
Bukh et al., "Sequence Analysis of the 5' Noncoding Region of Hepatitis C Virus," Proc. Nat. Acad. Sci. USA, 89:4942-4946 (1992).
Choo et al., "Genetic Organization and Diversity of the Hepatitis C Virus," Proc. Natl. Acad. Sci. USA, 88:2451-2455 (1991).
Fish et al., "Short-Term Cytotoxic Effects and Long-Term Instability of RNAi Delivered Using Lentiviral Vectors," BMC Molecular Biology, 5:9 (2004).

(Continued)

*Primary Examiner* — Brian Whiteman
(74) *Attorney, Agent, or Firm* — Wilson, Sonsini, Goodrich & Rosati

(57) ABSTRACT

The invention provides methods, compositions, and kits comprising small interfering RNA (shRNA or siRNA) that are useful for inhibition of viral-mediated gene expression. Small interfering RNAs as described herein can be used in methods of treatment of HCV infection. ShRNA and siRNA constructs targetING the internal ribosome entry site (IRES) sequence of HCV are described.

16 Claims, 26 Drawing Sheets

OTHER PUBLICATIONS

Grimm et al., "Fatality in Mice Due to Oversaturation of Cellular MicroRNA/Short Hairpin RNA Pathways," Nature, 441:537-541 (2006).

Han et al., "Characterization of the Terminal Regions of the Hepatitis C Viral RNA: Identification of Conserved Sequences in the 5' Untranslated Region and Poly(A) Tails at the 3' End," Proc. Natl. Acad. Sci. USA, 88:1711-1715 (1991).

Hannon et al., "Unlocking the Potential of the Human Genome with RNA interference," Nature, 431:371-378 (2004).

Hugle et al., "Current Therapy and New Molecuiar Approaches to Antiviral Treatment and Prevention of Hepatitis C," Rev. Med. Virol., 13:361-371 (2003).

Jubin et, al., "Hepatits C Virus Internal Ribosome Entry Site (IRES) Stem Loop IIId Contains Phylogenetically Conserved GGG Triplet Essential for Translation of IRES Folding," Journal of Virology, 74(22):10430-1437 (2000).

Kapadia et al., "Interference of Hepatitis C Virus RNA Replication by Short Interfering RNAs," Proc. Natl. Acad. Sci. USA, 100(4):2014-2018 (2003).

Kawasaki et al., "Short Hairpin Type at dsRNAs that are Controlled by tRNA$^{Val}$ Promoter Significantly Induce RNAi-mediated Gene Silencing in the Cytoplasm of Human Cells," Nucleic Acids Research, 31(2):700-707 (2003).

Kim et al., "Interferon Induction by siRNAs and ssRNAs Synthesized by Phage Polymerase," Nature Biotechnology, 22(3):321-325 (2004).

Kronke et al., "Alternative Approaches for Efficient Inhibition of Hepatitis C Virus RNA Replication by Small Interfering RNAs," Journal of Virology, 78(7):3436-3446 (2004).

Lagos-Quintana et al., "Identification of Novel Genes Coding for Small Expressed RNAs," Science, 294:853-858 (2001).

Layzer et al., "In Vivo Activity of Nuclease-Resistant siRNAs," RNA, 10:776-771 (2004).

Lieberman et al., "Interfering with Disease: Opportunities and Roadblocks to Harnessing RNA Interference," TRENDS in Molecular Medicine, 9(9):397-403 (2003).

Marques et al., "A Structural Basis for Discriminating Between Self and Nonself Double-Stranded RNAs in Mammalian Cells," Nature Biotechnology, 24(5):559-565 (2006).

McCaffrey et al., "Determinants of Hepatitis C Translational Initiation In Vitro, in Cultured Cells and Mice," Molecular Therapy, 5(6):676-684 (2002).

McCaffrey et al., "RNA Interference in Adult Mice," Nature, 418:38-39 (2002).

McCaffrey et al., "A Potent and Specific Morpholino Antisense Inhibitor of Hepatitis C Translation in Mice," Hepatology, 38(2):503-508 (2003).

McHutchison et al., "Future Therapy of Hepatitis C," Hepatology, 36(5-S1):S245-S252 (2002).

Mercer et al., "Hepatitis C Virus Replication in Mice with Chimeric Human Livers," Nature Medicine, 7(8):927-933 (2001).

Okamoto et al., "Nucleotide Sequence of the Genomic RNA of Hepatitis C Virus Isolated from a Human Carrier: Comparison with Reported Isolates for Conserved and Divergent Regions," J. Gen, Virol., 72(PT. 11):2697-2704 (1991) (Abstract).

Pietschmann et al., "Tissue Culture and Animal Models for Hepatitis C Virus," Clinics in Liver Disease, 7:23-43 (2003).

Qin et al., "Inhibiting HIV-1 Infection in Human T Cells by Lentiviral-Mediated Delivery of Small Interfering RNA Against CCR5," Proc. Natl. Acad. Sci. USA, 100(1):183-188 (2003).

Radhakrishnan et al., "RNA Interferences as a New Strategy Against Viral Hepatitis," Virology, 323:173-181 (2004).

Randall et al., "Interfering with Hepatitis C Virus RNA Replication," Virus Research, 102:19-25 (2004).

Randall et al, "Clearance of Replicating Hepatitis C Virus Replicon RNAs in Cell Culture by Small Interfering RNAs," Proc. Natl. Acad. Sci. USA, 100(1):235-240 (2003).

Rice, "Fresh Assault on Hepatitis C," Nature, 426:129-131 (2003).

Robbins et al., "Stable Expression of shRNAs in Human CD34$^+$ Progenitor Cells can Avoid lnduction of Interferon Responses to siRNAs In Vitro," Nature Biotechnology, 24(5):566-571 (2006).

Sen et al., "Inhibition of Hepatitis C Virus Protein Expression by RNA Interference," Virus Research, 96:27-35 (2003).

Seo et al., "Letter to the Editor: Small Interfering RNA-Mediated Inhibition of Hepatitis C Virus Replication in the Human Hepatoma Cell Line Huh-7," Journal of Virology, 77(1):810-812 (2003).

Seyhan et al., "Complete, Gene-Specific siRNA Libraries: Production and Expression in Mammalian Cells," RNA, 11(5)837-846 (2005).

Sookoian "New Therapies on the Horizon for Hepatitis C," Annals of Hepatology, 2(4):164-170 (2003).

Wang et al., "Small Hairpin RNAs Efficiently Inhibit Hepatitis C IRES-Mediated Gene Expression in Human Tissue Culture Cells and a Mouse Model," Molecular Therapy, 12(3):562-568 (2005).

Wilson et al., "RNA Interference Blocks Gene Expression and RNA Synthesis from Hepatitis C Replicons Propagated in Human Liver Cells,",Proc. Natl. Acad. Sci. USA, 100(5):2783-2788 (2003).

Yokota et al., "Inhibition of Intracellular Hepatitis C Virus Replication by Synthetic and Vector-Derived Small Interfering RNAs," EMBO Reports, 4(6):602-608 (2003).

Zhang et al., "Down-Regulation of Viral Replication by Adenoviral-Mediated Expression of siRNA Against Cellular Cofactors for Hepatitis C Virus," Virology, 320:135-143 (2004).

Zhang et al., "Antisense Oligonucleotide Inhibition of Hepatitis C Virus (HCV) Gene Expression in Livers of Mice Infected with an HCV-Vaccinia Virus Recombinant," Antimicrobial Agents and Chemotherapy, 43(2):347-353 (1999).

Yakota, et al., °Inhibition of Intracellular Hepatitis C Virus Replication by Synthetic and Vector-Derived Small Interfering RNAs, EMBO Reports, 4(6):602-608 (2003).

International Search Report, corresponding to PCT/US2006/021253, mailed Jun. 28, 2007 (3 Pages).

Ilves Heini et al. "Inhibition of hepatitis C IRES-mediated gene expression by small hairpin RNAs in human hepatocytes and mice." Annals of the New York Academy of Sciences, vol. 1082, Oct. 2006, pp. 52-55.

* cited by examiner

Seq ID NO: 11

1- GCCAGCCCCCGAUUGGGGGGCGACACUCCACCAUAGAUCACUCCCUGUGA -50
GGAACUACUGUCUUCAGCAGAAAGGCGUCUAGCCAUGGCGUUAGUAUGAG -100
UGUCGUGCAGCCUCCAGGACCCCCCCUCCGGGAGAGCCAUAGUGGUCUG -150
CGGAACCGGUGAGUACACCGGAAUUGCCAGGACGACCGGGUCCUUUCUUG -200
GAUCAACCCGCUCAAUGCCUGGAGAUUUGGGCGUGCCCCCGGAGACUGC -250
UAGCCGAGUAGUGUUGGGUCGCGAAAGGCCUUGUGGUACUGCCUGAUAGG -300
GUGCUUGCGAGUGCCCCGGGAGGUCUCGUAGACCGUGCACC[AUG]AGCACG -350
AAUCCUAAACCUCAAAGAAAAACCAAAACGUAACCAACCGCC

HCV IRES sequence

FIG. 1A

```
       C                              C                              C                              C
    C U U C                       C U U C                       C U U C                       C U U C
5'GG                       5'GG                       5'GG                       5'GG
    GAGCACCGAAUCCUAAACCUCAAAGA       GAGCACCGAAUCCUAAACCUCAAAGA       GAGCACCGAAUCCUAAAGCUCAAAGA       GAGCACCGAAUCCUAAAGCUCAAAGA
    ||||||||||||||||||||||||||       ||||||||||||||||||||||||||       ||||||||||||||||||||||||||       ||||||||||||||||||||||||||
    CUCGUGGCUUAGGAUUUGGAGUUUCU       CUCGUGGCUUAGGAUUUGGAGUUUCU       CUCGUGGCUUAGGAUUUCGAGUUUCU       CUCGUGGUUAGGAUUUCGAGUUUCU
3' U                        U   U    3' U                        U   U    3' U                        U   U    3' U                        U   U
      U                      C A      U                      C A      U                      C A      U                      C A
       C                              C                              C                              C
```

HCVa-wt shRNA (SEQ ID NO: 12)

HCVa-S

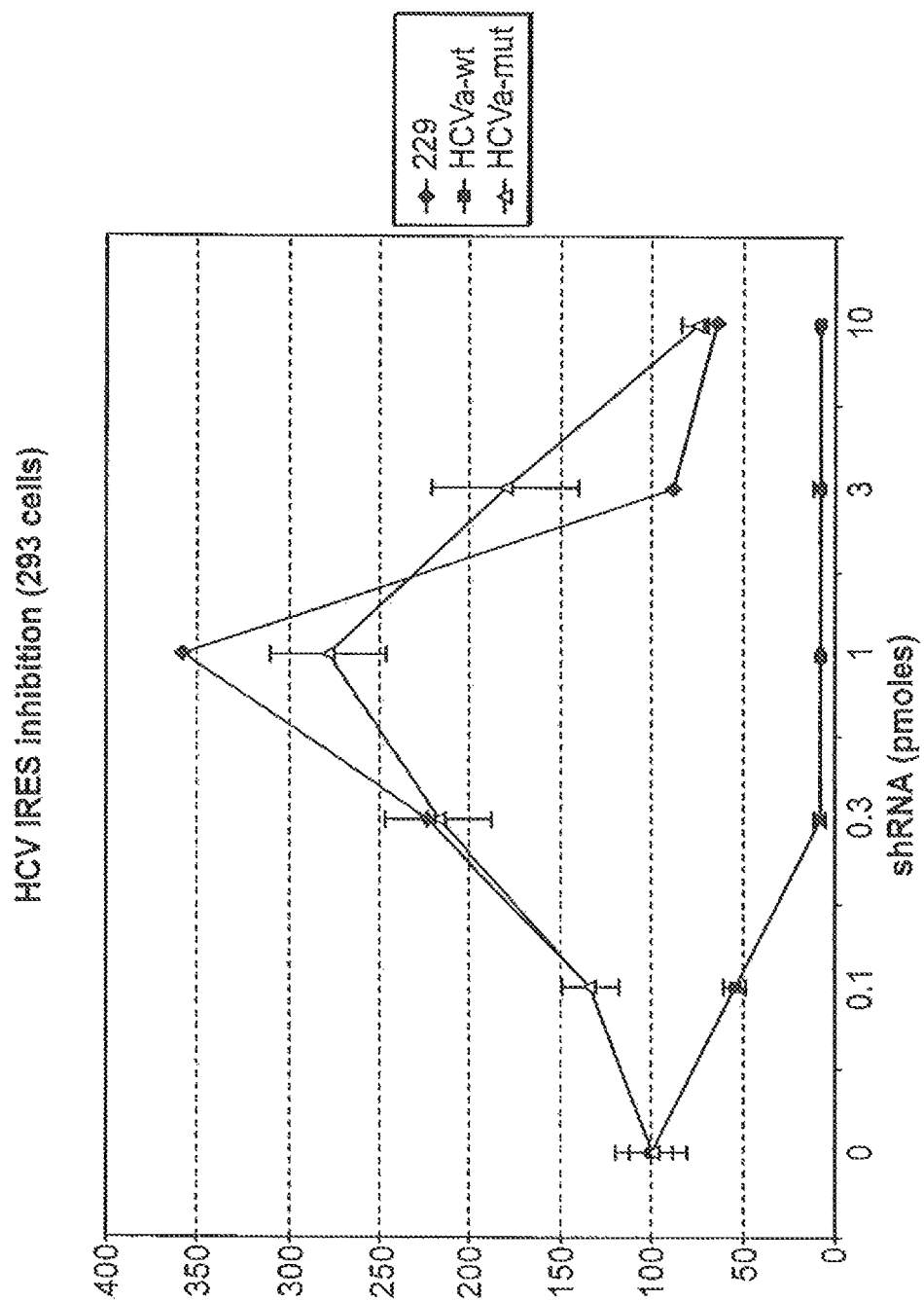

344-GAGCACGAAUCCUAAACCUCAAAGAAAAACC-374 (SEQ ID NO: 26)

CUCGUGCUUAGGAUUUGGA   #1 (SEQ ID NO: 19)
UCGUGCUUAGGAUUUGGAG   #2 (SEQ ID NO: 20)
CGUGCUUAGGAUUUGGAGU   #3 (SEQ ID NO: 21)
GUGCUUAGGAUUUGGAGUU   #4 (SEQ ID NO: 22)
UGCUUAGGAUUUGGAGUUU   #5 (SEQ ID NO: 23)
GCUUAGGAUUUGGAGUUUC   #6 (SEQ ID NO: 24)
CUUAGGAUUUGGAGUUUCU   #7 (SEQ ID NO: 25)

| SEQ ID NO of target site sequence | shRNA # | HCV IRES target site | Antisense sequence (5'-3') | fluc expression (%) at 1 nM shRNA | fluc expression (%) at 1 nM shRNA (Mutated target) | fluc expression (%) at 5 nM shRNA |
|---|---|---|---|---|---|---|
| SEQ ID NO:34 | hcv3 | 29-51 | CUCACAGGGGAGUGAUCUAUGGU | 74 +/-8 | | 50 +/-6 |
| SEQ ID NO:35 | sh23 | 35-59 | AGUAGUUCCUCACAGGGGAGUGAUC | 52 +/-5 | | 39 +/-4 |
| SEQ ID NO:36 | sh24 | 52-75 | CUUUCUGCGUGAAGACAGUAGUUCC | 44 +/-6 | | 28 +/-3 |
| SEQ ID NO:37 | hcv45 | 65-86 | AUGGUAGACGCUUUCUGCGUG | 82 +/-12 | | 62 +/-7 |
| SEQ ID NO:38 | sh17 | 73-94 | CUAACGCCAUGGCUAGACGCUU | 72 +/-9 | | 69 +/-8 |
| SEQ ID NO:39 | sh20 | 75-99 | UCAUCUAACGCCAUGGCUAGACGC | 63 +/-6 | 65 +/-6 | 42 +/-3 |
| SEQ ID NO:40 | sh25 | 82-106 | ACGACACUCAUAACGCCAUGGC | 64 +/-8 | | 39 +/-4 |
| SEQ ID NO:41 | sh19 | 135-159 | CCGGUUCCGCAGACCACUAUGGCUC | 50 +/-6 | 52 +/-12 | 27 +/-4 |
| SEQ ID NO:42 | sh26 | 152-176 | CAAUUCGGGUGUACUCACCGGUUCC | 66 +/-11 | | 50 +/-5 |
| SEQ ID NO:43 | hcv44 | 196-217 | CAUUGAGCGGGUUGAUCGGGUUG | 99 +/-10 | | 75 +/-8 |
| SEQ ID NO:44 | hcv41 | 204-224 | CUCCUAGGCAUUGAGCGGGUUG | 75 +/-9 | | 51 +/-6 |
| SEQ ID NO:45 | sh27 | 224-248 | AGUUCGCCGGGUCACGCCCAAAUUC | 75 +/-12 | | 70 +/-8 |
| SEQ ID NO:46 | sh28 | 253-277 | CUUUGGACCAACACUACUCGGUUCC | 40 +/-8 | | 36 +/-5 |
| SEQ ID NO:47 | sh29 | 278-302 | ACCCUAUCAGCAGUACCACAGGGC | 62 +/-6 | | 21 +/-3 |
| SEQ ID NO:48 | hcv7 | 288-309 | CGCAAGCACCCUAUCAGCAGUAG | 69 +/-8 | | 47 +/-5 |
| SEQ ID NO:31 | HCVb-wt | 299-323 | CCUUCCGGGGCACCUGAAGCACCC | 74 +/-9 | 72 +/-12 | 43 +/-5 |
| SEQ ID NO:32 | HCVc-wt | 318-342 | UGGUGCACGUCUACGAGACCUCCC | 36 +/-4 | 32 +/-5 | 17 +/-3 |
| SEQ ID NO:49 | sh7 | 320-342 | UGGUGCACGUCUACGAGACC | 41 +/-5 | 43 +/-8 | 21 +/-5 |
| SEQ ID NO:50 | hcv30 | 323-342 | UGGUGCACGUCUACGAGACC | 59 +/-6 | 57 +/-7 | 35 +/-4 |
| SEQ ID NO:51 | sh18 | 323-346 | CUCAUGGUGCACGUCUACGAGAC | 62 +/-8 | 65 +/-13 | 31 +/-8 |
| SEQ ID NO:52 | hcv22 | 326-346 | UUCGAGUGCAUGGUGCACGUCUAC | 50 +/-6 | 76 +/-9 | 55 +/-7 |
| SEQ ID NO:53 | sh38 | 328-352 | UUCGAGUGCAUGGUGCACGUCUAC | 54 +/-4 | 69 +/-6 | 12 +/-2 |
| SEQ ID NO:54 | sh39 | 331-355 | GGAAUUCGUGUGCAUGGUGCAC | 13 +/-1 | 24 +/-3 | 7 +/-1 |
| SEQ ID NO:55 | sh37 | 335-359 | UUUAGGAAUUCGUGUGCAUGGUG | 15 +/-2 | 16 +/-2 | 5 +/-1 |
| SEQ ID NO:56 | hcv17 | 337-359 | UUUAGGAAUUCGUGUGCAUGGUGC | 16 +/-2 | 24 +/-3 | 17 +/-2 |
| SEQ ID NO:27 | HCVa-wt | 344-368 | UCUUGAGGUUUAGGAAUUCGUGUGC | 8 +/-1 | 10 +/-1 | 4 +/-1 |
| SEQ ID NO:33 | HCVd-wt | 350-374 | GGUUUUCUUUGAGGUUUAGGAAUUC | 10 +/-1 | 10 +/-1 | 5 +/-1 |

FIG. 10

| Sequence ID# | Sequence (5'-3') | Target position on IRES | shRNA abbrev |
|---|---|---|---|
| SEQ ID NO:57 | gggACCAUGAUCACUCCUGAGCUUCCUGUCACUCAAGAGGGAGUGAUCUAUGGU | 29-51 | hcv3 |
| SEQ ID NO:58 | gggGAAGACUCCCUGAGUUCAAGAACUACUGAGGAGUCCUCACAGGAGUAGUUC | 35-59 | sh22 |
| SEQ ID NO:59 | gggAAGUACUGAGGAGUCCUGCUGUCCUGCUUCCUGUCACUCGUGAAGACAGUUC | 52-75 | sh24 |
| SEQ ID NO:60 | gggCACGGAGAAAGCGUCUAGCCAUGGCUAGACGCUUUCUCCGUG | 65-86 | hcv45 |
| SEQ ID NO:61 | gggAAGCGUCUAGCCAUGGCUAGAGCCAUGGCUAGACGCUU | 73-94 | hcv40 |
| SEQ ID NO:62 | gggCGUCUAGCCAUGGCGUUAGUAGUGUUGGGUCGCGAAAGGCCUUGUGGUACUGCCUGAUAGGGUGCUUGCGAGUGCCCCGGGAGGUCUCGUAGACCGU | 75-99 | sh20 |
| SEQ ID NO:63 | gggCCAUGGCGUUAGUAUGAGUGUCGUGCAGCCUCCAGGACCCCCCCUCCCGGGAGAGCCAUAGUGGUCUGCGGAACCGGUGAGUACACCGGAAUUGCCAGGA | 82-106 | sh25 |
| SEQ ID NO:64 | gggAGCCAUAGUGGUCUGCGGAACCGGUGAGUACACCGGAAUUGCCAGGACGACCGGGUCCUUUCUUGGAUCAACCCGCUCAAUGCCUGGAGAUUUGGGCGUGCCCCCCGCGAGACUGCUAGCCGAGUAGUGUUGGGUCGCGAAAGGCCUU | 135-159 | sh19 |
| SEQ ID NO:65 | gggAACCGGUGAGUACACCGGAAUUGCCAGGACGACCGGGUCC | 152-176 | sh26 |
| SEQ ID NO:66 | gggUCUUGGAUCAACCCGCUCAAUGCCUGGAGAUUUGGGCGUGCCCCCCGCGAGACUGCUAGCCGAGUAGUGUUGGGUCGCGAAAGGCCUUGUGGUACUGCCUGAUAGGGUGCUUGCGAGUGCCCCGGGAGGUCUCGUAGACCGUGCAUCAUGAGCACAAAUCCUAAACCUCAAAGA | 196-217 | hcv44 |
| SEQ ID NO:67 | cggCCAACCCGCUCAAUGCCUGGAGAUUUGGGCGUGCCCCCGCGAGACUGCUAGCCGAGUAGUGUUGGGUCGCGAAAGGCCUUGUGGUACUGCCUGAUAGGGUGCUUGCGAGUGCCCCGGGAGGUCUCGUAGACCGUGCAUCAUGAGCACAAAUCCUAAACCUCAAAGA | 204-224 | hcv41 |
| SEQ ID NO:68 | ggGAUUGGGCGUGCCCCCGCAGAGACUGCUAGCCGAGUAGUGUUGUGAGCGGUUG | 224-248 | sh27 |
| SEQ ID NO:69 | gggCCGAGUAGUGUUGGGUCGCGAAAGGCCUUGUGGUACUGCCUGAUAGGGUG | 253-277 | sh28 |
| SEQ ID NO:70 | gggGCCUGAUAGGGUGCUUGCGAGUGCCCCGGGAGGUCUCGUAGACCGUG | 279-302 | sh29 |
| SEQ ID NO:71 | gggCGCCUAUUGGGUCGGGGUUCUUGCGAGUGCCGUAGCCGAGUGCCCCUAGCACCGG | 279-302 | hcv7 |
| SEQ ID NO:16 | gggCGUGCCUAGCCGAGUAGU | 288-309 | HCVb-wt |
| SEQ ID NO:17 | gggGUGCCUAGCCGAGUAGUGUUGGGUCGCGAAAGGCCUUGUGGUACUGCCUGAUAGGGUGCUUGCGAGUGCCCCGGGAGGUCUCGUAGACCGUGCAUCAUGAGCACC | 299-323 | HCVc-wt |
| SEQ ID NO:72 | gggAGGUCUCGUAGACCGUGCACCAUGAGCACGAAUCCUAAACCUCAAAGACCCCUCCCGGGAGAGCCAUAGUGGUCUGCGGAACCGGUGAGUACACCGGAAUUGCCAGGAC | 318-342 | sh17 |
| SEQ ID NO:73 | gggUCUCGUAGACCGUGCACCAUGGUCUACGAGACC | 320-342 | hcv30 |
| SEQ ID NO:74 | gggCGUAGACCGUGCACCAUGAGCACGAAUCCUAAACCUCAAAGAAAAACCAAACGUAACACCAACCGUCGCCCACAAGGACGUCGGCGAACCGGUGAGUACACCGGAAUUGCCAGGACGACCGGGUCCUUUCUUGGAUCAACCCGCUCAAUGCCUGGAGAUUUGGGCGUGCCCCCGCGAGACUGCUAGCCGAGUAGUGUUGGGUCGCGAAAGGCCUUGUGGUACUGCCUGAUAGGGUG | 322-342 | sh18 |
| SEQ ID NO:75 | gggUAGACCGUGCACCAUGAGCACGAAUCCUUGCACGGUCUACGAGAC | 323-346 | hcv22 |
| SEQ ID NO:76 | gggACCGUGCACCAUGAGCACGAAUCCUGCACCGGUCUACGA | 326-346 | sh38 |
| SEQ ID NO:77 | gggGUAGACCGUGCACCAUGAGCACGAAUCCCGUGCACGGUCACGUCUAC | 328-352 | sh39 |
| SEQ ID NO:78 | gggGUGCACCAUGAGCACGAAUCCUAAACCUGCACGGUGCAC | 331-355 | sh37 |
| SEQ ID NO:79 | gggCACCAUGAGCACGAAUCCUAAACGAGUGCUCAUGGUGCAC | 335-359 | hcv17 |
| SEQ ID NO:12 | gggAGCAGAGCACGAAUCCUAAACGAGCACGAAUCCUAAACCUCUUAGAUUCGUGCUCU | 337-359 | sh11 |
| SEQ ID NO:18 | gggAAUCCUAAACCUCAAAGAAAAACCAAACGUAAGCACACCGGGUUAGGAUUGUu | 344-368 | HCVa-wt |
| SEQ ID NO:80 | cggGAAUCCGUGCACCGUGCACGAAUUCUUCGUGCUCAUGGUGCACGGUu | 350-374 | HCVd-wt |
| SEQ ID NO:81 | cccCGUGCACCAUGAGCACGAAUCCUGUGCACCAUGGUGCACGGUu | 334-352 | sh51 |

*shRNA loops are underlined

FIG. 16A

| Sequence ID# | sequence (5'-3') | Target position on IRES | shRNA abbrev |
|---|---|---|---|
| SEQ ID NO:82 | ggGUGCACCAUGAGCAAGAAUCUUGUCAAUCGUCUCAUGGUGCACuu | 335-353 | sh52 |
| SEQ ID NO:83 | gggCCUAAACCUCAAAGAAACUUCCGUCAUUCUGUAGGUUUAGGuu | 354-372 | sh53 |
| SEQ ID NO:84 | gggCUAAACCUCAAAGAAACUUCCGUCUGUCAGUUUCUGAGGUUAGcuu | 355-373 | sh54 |
| SEQ ID NO:85 | gggUAAACCUCAAAGAAACUUCCUCCACUUCUCAGGUUUGAGGUUUAuu | 356-374 | sh55 |
| SEQ ID NO:86 | gggCACGAAUCCUCAAAGAAACUGGCACGAACUUCUUGAGGAUUCGUGuu | 346-364 | sh40 |
| SEQ ID NO:87 | gggCACGAAUCCUCAAAACCUCACAACAACUGAGGUUAGGAUUCGUGCuu | 345-364 | sh49 |
| SEQ ID NO:88 | gggCACGAAUCCUCAAACCUCAAACCUCUUGAGGUUUAGGAUUCGUGCuu | 346-364 | sh42 |
| SEQ ID NO:89 | gggCACGAAUCCUCAAACCUAACCUCUUGAGGUUAGGAUUCGUGCuu | 346-364 | sh46 |
| SEQ ID NO:90 | gggCACGAAUCCUCAAACCUAAACC*CAUCUUUGAGGUUUAGGAUUCGUGuu | 346-364 | sh44 |
| SEQ ID NO:91 | gggCACGAAUCCUAAACCUCAAAAGAAACACUUCUUUGAGGUUUAGGAUUCGUGuu | 346-364 | sh48 |
| SEQ ID NO:92 | gggCACGAAUCCUAAACCUCAAAGAAACAAUUCUUUCUUGAGGUUUAGGAUUCGUGuu | 346-364 | sh43 |
| SEQ ID NO:93 | gggCACGAAUCCUAAACCUCAAAGAAACAAUUCUUUGAGGUUUAGGAUUCGUGuu | 346-364 | sh47 |
| SEQ ID NO:94 | gggCACGAAUCCUAAACCUCAAACCUCGUCAUUGAGGUUUAGGAUUCGUGC | 346-364 | sh41 |
| SEQ ID NO:95 | gggCACGAAUCCUAAACCUCAAACCUCGUCCUUCGUCAUUGAGGAUUCGUGuu | 346-364 | sh45 |
| SEQ ID NO:96 | gggAGCACGAAUCCUAACCUCCAAAGAAACACUUUGAGGUUAGGAUUCGUGCUGCuu | 344-368 | sh22 |
| SEQ ID NO:97 | gggAGCACGAAUCCUAAACCCCAAAGACAAUGAACACACUUUCUUUGAGGUUAGGAUUCGUGCUGCuu | 344-368 | sh61 |
| SEQ ID NO:98 | gggAGCACGAAUCCUAAACCUCAAAGAAACACUUCCUUCUUUGAGGUUAGGAUUCGUGCUuu | 344-368 | sh60 |
| SEQ ID NO:99 | gggAGCACGAAUCCUAAACCUCAAAGAAACAAUAUCUUUCUUGAGGUUAGGAUUCGUGCUuu | 344-368 | sh59 |
| SEQ ID NO:100 | gggAGCACGAAUCCUAAACCUCAAAGAAACAACUUCUUUCUUGAGGUUAGGAUUCGUGCUuu | 344-368 | sh58 |
| SEQ ID NO:101 | gggAGCACGAAUCCUAAACCUAAGACACUUCUUUGAGGUUUAGGAUUCGUGCUuu | 344-368 | sh57 |
| SEQ ID NO:102 | cccAGCACGAAUCCUAAACCUAAAGACAAUUCGUCAUUGAGGUUAGGAUUCGUGCUCuu | 344-368 | sh56 |
| SEQ ID NO:103 | gggAGCACGAAUCCUAAACCUAAGACUACUCCGUCAUCGUCCACUGAGGUUAGGAUUGUGUCuu | 344-369 | sh35 |
| SEQ ID NO:104 | gggAGCACGAAUCCUAAACCUCAAAGACAAUUCUUGAGGUUAGGAUUAGGAGUUUCu | 344-368 | sh2 |
| SEQ ID NO:105 | gggAGCAACGAAUCCUAAACCUCCAAGCAAGACUACGGCGACUGAGGUUAGGAUUGAGUUUCu | 344-368 | sh36 |
| SEQ ID NO:106 | gggAGCAGCACGAAUCCUAAAUCCUAAACCUCUCCGUCGAAGGUCAGGAUUGAGCUuu | 344-362 | sh19-1 |
| SEQ ID NO:107 | gggAGCAGCACGAAUCCUAAACCUCACAUUCCGUCAAGGUUAGGAUUCGUGCuu | 345-363 | sh19-2 |
| SEQ ID NO:108 | gggAGCACGAAUCCUAAACCUCAACUUCCGUCUGUCUGUCAUGAGGUUAGGAUUCGUGuu | 346-364 | sh19-3 |
| SEQ ID NO:109 | gggCACGAAUCCUAAACCUCAAACUUCCGUCAUUGAGGUUUAGGAUUCGUGuu | 347-365 | sh19-4 |
| SEQ ID NO:110 | gggACGAAUCCUAAACCUCAAACUUCCGUCAUUGAGGUUUAGGAUUCGuu | 348-366 | sh19-5 |

*shRNA loops are underlined

FIG. 16B

SEQUENCE LISTING

<160> NUMBER OF SEQ ID NOS: 113

<210> SEQ ID NO 1
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
taatacgact cactataggg agcacgaatc ctaaacctca aagacttcct gtcatctttg     60
aggtttagga ttcgtgctct t                                              81

<210> SEQ ID NO 2
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aagagcacga atcctaaacc tcaaagatga caggaagtct tgaggttta ggattcgtgc     60 tccctatagt gagtcgtatt a                                              81

<210> SEQ ID NO 3
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
taatacgact cactataggg gcggtgccta tgtctcagcc tcttctcact tcctgtcatg    60
agaagaggct gagacatagg caccgcctt                                      89

<210> SEQ ID NO 4
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
attatgctga gtgatatccc cacggataca gagtcggaga agagtgaagg acagtactct    60
tctccgactc tgtatccgtg gcggaa                                         86

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atcgatcccc agtggaaaga cgcgcag                                        27

<210> SEQ ID NO 6
<211> LENGTH: 42

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aacacctttc ctgctttgtg gcaccagaag cttaagccta gg                            42

<210> SEQ ID NO 7
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
accggagcac gaatcctaaa cctcaaagac ttcctgtcat ctttgaggtt taggattcgt         60
gctctttttt g                                                             71

<210> SEQ ID NO 8
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatccaaaaa agagcacgaa tcctaaacct caaagatgac aggaagtctt tgaggtttag         60
gattcgtgct c                                                             71

<210> SEQ ID NO 9
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
accgggcggt gcctatgtct cagcctcttc tcacttcctg tcatgagaag aggctgagac         60
ataggcaccg ccttttttt                                                     78

<210> SEQ ID NO 10
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccgccacgga tacagagtcg gagaagagtg aaggacagta ctcttctccg actctgtatc         60
cgtggcggaa aaaactag                                                      78

<210> SEQ ID NO 11
<211> LENGTH: 393
<212> TYPE: RNA
<213> ORGANISM: Hepatitis C Virus

<400> SEQUENCE: 11
gccagccccc gauuggggc gacacuccac cauagaucac uccccuguga ggaacuacug          60
```

```
ucuucacgca gaaagcgucu agccauggcg uuaguaugag ugucgugcag ccuccaggac    120
ccccccuccc gggagagcca uaguggucug cggaaccggu gaguacaccg gaauugccag    180
gacgaccggg uccuuucuug gaucaacccg cucaaugccu ggagauuugg gcgugcccc     240 gcgagacugc uagccgagua guguuggguc gcgaaaggcc uugugguacu gccugauagg    300
gugcuugcga gugccccggg aggucucgua gaccgugcac caugagcacg aauccuaaac    360
cucaaagaaa aaccaaacgu aacaccaacc gcc                                 393
```

<210> SEQ ID NO 12
<211> LENGTH: 64
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 12

```
gggagcacga auccuaaacc ucaaagacuu ccugucaucu uugagguuua ggauucgugc    60
ucuu                                                                 64
```

<210> SEQ ID NO 13
<211> LENGTH: 64
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 13

```
gggagcacca auccuaaacc ucaaagacuu ccugucaucu uugagguuua ggauggugc     60 ucuu                                                                 64
```

<210> SEQ ID NO 14
<211> LENGTH: 64
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 14

```
gggagcacga auccuaaagc ucaaagacuu ccugucaucu uugagcuuua ggauucgugc    60
ucuu                                                                 64
```

<210> SEQ ID NO 15
<211> LENGTH: 64
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 15

```
gggagcacca auccuaaagc ucaaagacuu ccugucaucu uugagcuuua ggauggugc     60 ucuu                                                                 64
```

<210> SEQ ID NO 16
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide

```
<400> SEQUENCE: 16
gggugcuugc gagugccccg ggaggcuucc ugucaccucc cggggcacuc gcaagcaccc    60

<210> SEQ ID NO 17
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gggaggucuc guagaccgug caccacuucc ugucauggug cacggucuac gagaccuccc    60

<210> SEQ ID NO 18
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gggaaugcua aaccucaaag aaaaacccuu ccugucaggu uuucuuuga gguuuacgau    60 uc                                                                 62

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonuclectide

<400> SEQUENCE: 19
cucgugcuua ggauuugga                                                19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ucgugcuuag gauuuggag                                                19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
cgugcuuagg auuuggagu                                                19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 22
gugcuuagga uuuggaguu                                                   19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ugcuuaggau uuggaguuu                                                   19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gcuuaggauu uggaguuuc                                                   19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
cuuaggauuu ggaguuucu                                                   19

<210> SEQ ID NO 26
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gagcacgaau ccuaaaccuc aaagaaaaac c                                     31

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ucuuugaggu uuaggauucg ugcuc                                            25

<210> SEQ ID NO 28
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
```
ucuuugaggu uuaggauugg ugcuc                              25

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucuuugagcu uuaggauucg ugcuc                              25

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ucuuugagcu uuaggauugg ugcuc                              25

<210> SEQ ID NO 31
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ccucccgggg cacucgcaag caccc                              25

<210> SEQ ID NO 32
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uggugcacgg ucuacgagac cuccc                              25

<210> SEQ ID NO 33
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gguuuuucuu ugagguuuag gauuc                              25

<210> SEQ ID NO 34
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
cucacagggg agugaucuau ggu                                23

```
<210> SEQ ID NO 35
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
aguaguuccu cacaggggag ugauc                                              25

<210> SEQ ID NO 36
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cuuucugcgu gaagacagua guucc                                              25

<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
auggcuagac gcuuucugcg ug                                                 22

<210> SEQ ID NO 38
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cuaacgccau ggcuagacgc uu                                                 22

<210> SEQ ID NO 39
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ucauacuaac gccauggcua gacgc                                              25

<210> SEQ ID NO 40
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
acgacacuca uacuaacgcc auggc                                              25
```

```
<210> SEQ ID NO 41
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ccgguuccgc agaccacuau ggcuc                                       25

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
caauuccggu guacucaccg guucc                                       25

<210> SEQ ID NO 43
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cauugagcgg guugauccaa ga                                          22

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
cuccaggcau ugagcggguu g                                           21

<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
agucucgcgg gggcacgccc aaauc                                       25

<210> SEQ ID NO 46
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cuuucgcgac ccaacacuac ucggc                                       25

<210> SEQ ID NO 47
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
acccuaucag gcaguaccac aaggc                                              25

<210> SEQ ID NO 48
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
cgcaagcacc cuaucaggca gu                                                 22

<210> SEQ ID NO 49
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
uggugcacgg ucuacgagac cuc                                                23

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
uggugcacgg ucuacgagac c                                                  21

<210> SEQ ID NO 51
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cucauggugc acggucuacg agac                                               24

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cucauggugc acggucuacg a                                                  21

<210> SEQ ID NO 53
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 53
uucgugcuca uggugcacgg ucuac                                               25

<210> SEQ ID NO 54
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ggauucgugc ucauggugca cgguc                                               25

<210> SEQ ID NO 55
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uuuaggauuc gugcucaugg ugcac                                               25

<210> SEQ ID NO 56
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uuuaggauuc gugcucaugg ugc                                                 23

<210> SEQ ID NO 57
<211> LENGTH: 59
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gggaccauag aucacucccc ugugagcuuc cugucacuca caggggagug aucuauggu          59

<210> SEQ ID NO 58
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gggaucacuc cccugugagg aacuacucuu ccugucaagu aguccucac aggggaguga          60 uc                                                                        62

<210> SEQ ID NO 59
<211> LENGTH: 61
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 59
gggaacuacu gucuucacgc agaaagcuuc cugucacuuu cugcgugaag acaguaguuc    60
c                                                                   61

<210> SEQ ID NO 60
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gggcacgcag aaagcgucua gccaucuucc ugucaauggc uagacgcuuu cugcgug       57

<210> SEQ ID NO 61
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gggaagcguc uagccauggc guuagcuucc ugucacuaac gccauggcua gacgcuu       57

<210> SEQ ID NO 62
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gggcgucuag ccauggcguu aguaugacuu ccugucauca uacuaacgcc auggcuagac    60
gc                                                                  62

<210> SEQ ID NO 63
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gggccauggc guuaguauga gugucgucuu ccugucaacg acacucauac uaacgccaug    60
gc                                                                  62

<210> SEQ ID NO 64
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
gggagccaua guggucugcg gaaccggcuu ccugucaccg guuccgcaga ccacuauggc    60
uc                                                                  62
```

```
<210> SEQ ID NO 65
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
gggaaccggu gaguacaccg gaauugcuuc cugucacaau uccgguguac ucaccgguuc     60
c                                                                    61

<210> SEQ ID NO 66
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gggucuugga ucaacccgcu caaugcuucc ugucacauug agcggguuga uccaaga       57

<210> SEQ ID NO 67
<211> LENGTH: 55
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gggcaacccg cucaaugccu ggagcuuccu gucacuccag gcauugagcg gguug         55

<210> SEQ ID NO 68
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gggauuuggg cgugccccg cgagacucuu ccugucaagu ucgcgggggg cacgcccaaa     60
uc                                                                   62

<210> SEQ ID NO 69
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gggccgagua guguugggguc gcgaaagcuu ccugucacuu ucgcgaccca acacuacucg   60
gc                                                                   62

<210> SEQ ID NO 70
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 70
gggccuugug uacugccug auagggucuu ccugucaacc uaucaggca guaccacaag    60 gc    62

<210> SEQ ID NO 71
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gggacugccu gauaggugc uugcgcuucc ugucacgcaa gcacccuauc aggcagu    57

<210> SEQ ID NO 72
<211> LENGTH: 58
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gggaggucuc guagaccgug caccacuucc ugucauggug cacggcuac gagaccuc    58

<210> SEQ ID NO 73
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
gggucucgua gaccgugcac cacuuccugu cauggugcac ggucuacgag acc    53

<210> SEQ ID NO 74
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
gggucucgua gaccgugcac caugagcuuc cugucacuca uggugcacgg ucuacgagac    60

<210> SEQ ID NO 75
<211> LENGTH: 55
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gggucguaga ccgugcacca ugagcuuccu gucacucaug gugcacgguc uacga    55

<210> SEQ ID NO 76
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonuceotide -continued

```
<400> SEQUENCE: 76
ggguagaccg ugcaccauga gcacgaacuu ccugucauuc gugcucaugg ugcacggucu    60
ac                                                                  62

<210> SEQ ID NO 77
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gggaccgugc accaugagca cgaaucccuu ccugucagga uucgugcuca uggugcacgg    60
uc                                                                  62

<210> SEQ ID NO 78
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gggugcacca ugagcacgaa uccuaaacuu ccugucauuu aggauucgug cucauggugc    60
ac                                                                  62

<210> SEQ ID NO 79
<211> LENGTH: 58
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gggcaccaug agcacgaauc cuaaacuucc ugucauuuag gauucgugcu cauggugc      58

<210> SEQ ID NO 80
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gggaccgugc accaugagca ccuuccuguc agugcucaug gugcacgguc uu            52

<210> SEQ ID NO 81
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gggcgugcac caugagcacg aacuuccugu cauucgugcu cauggugcac guu           53

<210> SEQ ID NO 82
<211> LENGTH: 52
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 82
gggugcacca ugagcacgaa ucuuccuguc aauucgugcu cauggugcac uu            52

<210> SEQ ID NO 83
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
gggccuaaac cucaaagaaa aacuuccugu cauuuuucuu ugagguuuag guu           53

<210> SEQ ID NO 84
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
gggcuaaacc ucaaagaaaa accuuccugu caguuuucu uugagguuua guu            53

<210> SEQ ID NO 85
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
ggguaaaccu caaagaaaaa cccuuccugu cagguuuuuc uuugaggguu auu           53

<210> SEQ ID NO 86
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gggcacgaau ccuaaaccuc acuuccuguc augagguuua ggauucgugc uu            52

<210> SEQ ID NO 87
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gggcacgaau ccuaaaccuc acaacaacaa cugagguuua ggauucgugc uu            52

<210> SEQ ID NO 88
<211> LENGTH: 48
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 88
gggcacgaau ccuaaaccuc acuuccuuga gguuuaggau ucgugcuu              48

<210> SEQ ID NO 89
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
gggcacgaau ccuaaaccuc aaacaacuga gguuuaggau ucgugcuu              48

<210> SEQ ID NO 90
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
gggcacgaau ccuaaaccuc auucuuugag guuuaggauu cgugcuu               47

<210> SEQ ID NO 91
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
gggcacgaau ccuaaaccuc acaauaugag guuuaggauu cgugcuu               47

<210> SEQ ID NO 92
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
gggcacgaau ccuaaaccuc agaaaugagg uuuaggauuc gugcuu                46

<210> SEQ ID NO 93
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
gggcacgaau ccuaaaccuc acucuugagg uuuaggauuc gugcuu                46

<210> SEQ ID NO 94
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 94
gggcacgaau ccuaaaccuc acuuccuguc augagguuua ggauucgugc            50

<210> SEQ ID NO 95
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
gggcacgaau ccuaaaccuc aacuuccugu cauugagguu uaggauucgu gc          52

<210> SEQ ID NO 96
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
gggagcacga auccuaaacc ucaaagacaa caacaacucu uugagguuua ggauucgugc  60
ucuu                                                              64

<210> SEQ ID NO 97
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
gggagcacga auccuaaacc ucaaagaaac aacucuuuga gguuuaggau ucgugcucuu  60

<210> SEQ ID NO 98
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gggagcacga auccuaaacc ucaaagacuu ccuucuuuga gguuuaggau ucgugcucuu  60

<210> SEQ ID NO 99
<211> LENGTH: 59
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
gggagcacga auccuaaacc ucaaagacaa uaucuuugag guuuaggauu cgugcucuu   59

<210> SEQ ID NO 100
<211> LENGTH: 59
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 100
gggagcacga auccuaaacc ucaaagauuc uuucuuugag guuuaggauu cgugcucuu    59

<210> SEQ ID NO 101
<211> LENGTH: 58
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
gggagcacga auccuaaacc ucaaagacuc uucuuugagg uuuaggauuc gugcucuu    58

<210> SEQ ID NO 102
<211> LENGTH: 58
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gggagcacga auccuaaacc ucaaagagaa aucuuugagg uuuaggauuc gugcucuu    58

<210> SEQ ID NO 103
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
gggagcacga auccuaaacc ucaaagacuu ccugucaucu uugagguuua ggauucgugc    60
uc                                                                 62

<210> SEQ ID NO 104
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
gggagcacga auccuaaacc ucaaagacuu ccugucaucu uugagguuua              50

<210> SEQ ID NO 105
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
gggagaaacu ccaaauccua agcacgagcu uccugucacu cgugcuuagg auuggaguu    60 ucuuu                                                              65

<210> SEQ ID NO 106
<211> LENGTH: 52
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 106
gggagcacga auccuaaacc ucuuccuguc aagguuuagg auucgugcuc uu             52

<210> SEQ ID NO 107
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
gggagcacga auccuaaacc uccuuccugu cagagguuua ggauucgugc uuu            53

<210> SEQ ID NO 108
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
gggcacgaau ccuaaaccuc acuuccuguc augagguuua ggauucgugc uu             52

<210> SEQ ID NO 109
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gggcacgaau ccuaaaccuc aacuuccugu cauugagguu uaggauucgu guu            53

<210> SEQ ID NO 110
<211> LENGTH: 53
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
gggacgaauc cuaaaccuca aacuuccugu cauugaggu uuaggauucg uuu             53

<210> SEQ ID NO 111
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
cuuccuguca                                                           10

<210> SEQ ID NO 112
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 112
caacaacaac                                                                      10

<210> SEQ ID NO 113
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gggcacgaau ccuaaaccuc acuccuguc augagguuua ggauucgugc uu                        52
```

INHIBITION OF VIRAL GENE EXPRESSION USING SMALL INTERFERING RNA

CROSS-REFERENCE TO RELATED APPLICATIONS

This application is a continuation patent application of U.S. application Ser. No. 11/444,901 filed on Jun. 1, 2006 now U.S. Pat. No. 7,902,351, which is a continuation-in-part of PCT application PCT/US2005/032768, filed Sep. 12, 2005, which claims priority under 35 U.S.C. §119 from U.S. Provisional Application No. 60/608,574, filed Sep. 10, 2004, all of which are incorporated herein by reference in their entirety.

STATEMENT REGARDING FEDERALLY SPONSORED RESEARCH OR DEVELOPMENT

This invention was made in part during work supported by grant no. 5R43AI056611 from the National Institutes of Health. The government may have certain rights in the invention.

FIELD OF THE INVENTION

The invention relates to inhibition of viral gene expression, for example, hepatitis C IRES-mediated gene expression, with small interfering RNA (shRNA and siRNA).

BACKGROUND OF THE INVENTION

Treatment and prevention of Hepatitis C virus (HCV) infections remains a major challenge for controlling this worldwide health problem; existing therapies are only partially effective and no vaccine is currently available. Hepatitis C (HCV) virus infects more than 170 million people worldwide and is the leading cause of liver transplants. Existing treatments, including ribavirin and pegylated interferon alpha, are effective only in approximately 50 percent of patients and have substantial side effects. The development of more effective HCV treatments is hampered by the lack of a good small animal model, the inability to stably culture the virus in tissue culture cells, and the high viral mutation rate [1-3]. The availability of an HCV replicon system has allowed the study of HCV replication, host-cell interactions and evaluation of anti-viral agents, and more recently, a transgenic chimeric humanized mouse liver model was developed that allows full HCV infection [4-7]. Moreover, the use of in vivo imaging of HCV IRES-dependent reporter systems has facilitated efficient evaluation of delivery and inhibition by anti-HCV agents in mouse liver over multiple time points using the same animals [8].

RNA interference is an evolutionarily conserved pathway that leads to down-regulation of gene expression. The discovery that synthetic short interfering RNAs (siRNAs) of about 19-29 base pairs can effectively inhibit gene expression in mammalian cells and animals without activating an immune response has led to a flurry of activity to develop these inhibitors as therapeutics [9]. Chemical stabilization of siRNAs results in increased serum half life [10], suggesting that intravenous administration may achieve positive therapeutic outcomes if delivery issues can be overcome. Furthermore, small hairpin RNAs (shRNA) have also shown robust inhibition of target genes in mammalian cells and can be easily expressed from bacteriophage (e.g. T7, T3 or SP6) or mammalian (pol III such as U6 or H1 or polII) promoters, making them excellent candidates for viral delivery [11].

Efforts have been made to find effective nucleic acid-based inhibitors against HCV, as existing treatments are not fully effective (reviewed in [4, 12]). These efforts include traditional antisense oligonucleotides, phosphorodiamidate morpholino oligomers [8], ribozymes, and more recently siRNAs. It has been shown that siRNAs can effectively target HCV in human tissue culture cells [13-19] and in animal systems [20].

BRIEF SUMMARY OF THE INVENTION

The invention provides methods, compositions, and kits for inhibition of IRES-mediated gene expression in a virus, e.g., hepatitis C virus (HCV).

For the inhibitory RNA sequences listed in FIGS. 4A and 10 and Table 1 (e.g., SEQ ID NOs:19-26), a complementary sequence is implied, as are sequences unrelated to the target that may be appended one or both ends of each strand, for example the 3' ends, as will be known to one skilled in the art. The inhibitory (antisense recognition) sequences shown in FIG. 4A, FIG. 10, and in Table 1 can be incorporated into either shRNA or siRNA. In the case of shRNA, the sequence shown is additionally linked to its complementary sequence by a loop that includes nucleotide residues usually unrelated to the target. An example of such a loop is shown in the shRNA sequences depicted in FIG. 1B and FIG. 1C as well as in FIG. 16A-B. In the case of both siRNAs and shRNAs, the strand complementary to the target generally is completely complementary, but in some embodiments, the strand complementary to the target can contain mismatches (see, for example, SEQ ID NOs:13, 14, and 15). The sequence can be varied to target one or more genetic variants or phenotypes of the virus being targeted by altering the targeting sequence to be complementary to the sequence of the genetic variant or phenotype. The strand homologous to the target can differ at about 0 to about 5 sites by having mismatches, insertions, or deletions of from about 1 to about 5 nucleotides, as is the case, for example, with naturally occurring microRNAs. In some embodiments, a sequence can target multiple viral strains, e.g., of HCV, although the sequence differs from the target of a strain at least one nucleotide (e.g., one, two, or three nucleotides) of a targeting sequence In one aspect, the invention provides a composition comprising at least one small interfering RNA that is at least partially complementary to, and capable of interacting with a polynucleotide sequence of a virus, such that inhibition of viral gene expression results from the interaction of the small interfering RNA with the viral target sequence. In one embodiment, the composition includes at least one shRNA, for example, comprising, consisting of, or consisting essentially of a sequence selected from the group consisting of SEQ ID NO:12, SEQ ID NO:16, SEQ ID NO:17, and SEQ ID NO:18, or comprising or consisting essentially of a sequence selected from the group consisting of SEQ ID NO:27, SEQ ID NO:32, and SEQ ID NO:33. In one embodiment, the shRNA comprises, consists of, or consists essentially of the sequence depicted in SEQ ID NO:12. In another embodiment, the composition includes at least one siRNA. In one embodiment, the composition includes at least one siRNA or shRNA, for example, comprising or consisting essentially of a sequence selected from the group consisting of SEQ ID NO:19, SEQ ID NO:20, SEQ ID NO:21, SEQ ID NO:22, SEQ ID NO:23, SEQ ID NO:23, SEQ ID NO:24, SEQ ID NO:25, SEQ ID NO:27, SEQ ID NO:32, and SEQ ID NO:33. In some embodiments, the small interfering RNA, e.g., shRNA or siRNA, interacts with a viral sequence of about 19 to about 30 nucleotides, or about 19 to about 25 nucleotides, for example, any of about 19, 20, 21, 22, 23, 24, 25, 26, 27, 28, 29, or 30 nucleotides. In some embodiments, the small interfering RNA binds to a hepatitis C virus sequence. In one embodiment, the small interfering RNA binds to a sequence within the internal ribosome entry site (IRES) sequence of a hepatitis C virus, for example, to the sequence depicted in SEQ ID NO:26 (residues 344-374 of SEQ ID NO:11). In one embodiment, the hepatitis C virus is HCV genotype 1a.

In some embodiments, a composition of the invention comprises a pharmaceutically acceptable excipient, for example, water or saline, and optionally, are provided in a therapeutically effective amount, e.g., for treating HCV infection in a human or in a non-human primate such as a chimpanzee or new world monkey. In one embodiment, the composition is a pharmaceutical composition comprising, consisting of, or consisting essentially of at least one shRNA or siRNA as described herein and a pharmaceutically acceptable excipient.

In another aspect, the invention relates to a kit that includes any of the compositions described above, and optionally, further includes instructions for use in a method of inhibiting gene expression in a virus or treating a viral infection in an individual as described herein. In one embodiment, the kit is for use in a method for treating HCV infection in an individual, such as a human, and comprises an shRNA comprising, consisting of, or consisting essentially of a sequence selected from the group consisting of SEQ ID NO:12, SEQ ID NO:16, SEQ ID NO:17, and SEQ ID NO:18; or comprising or consisting essentially of a sequence selected from the group consisting of SEQ ID NO:27, SEQ ID NO:32, and SEQ ID NO:33, or an siRNA comprising or consisting essentially of a sequence selected from the group consisting of SEQ ID NO:19, SEQ ID NO:20, SEQ ID NO:21, SEQ ID NO:22, SEQ ID NO:23, SEQ ID NO:23, SEQ ID NO:24, SEQ ID NO:25, SEQ ID NO:27, SEQ ID NO:32, and SEQ ID NO:33, and optionally further comprises instructions for use in a method of inhibiting gene expression in a hepatitis C virus, such as HCV genotype 1a, or instructions for use in a method of treating a hepatitis C (such as HCV genotype 1a) viral infection in an individual, such as a human, or a non-human primate such as a chimpanzee.

In another aspect, the invention provides a method for treatment of a viral infection in an individual, such as a mammal, for example, a human or non-human primate. The method includes administering to the individual a therapeutically effective amount of a small interfering RNA, such as shRNA or siRNA, that is at least partially complementary to and capable of binding to a polynucleotide sequence of the virus and a pharmaceutically acceptable excipient, such that binding of the small interfering RNA to the viral polynucleotide sequence inhibits gene expression in the virus, e.g., decreases the amount of viral expression in the individual or decreases the amount of viral expression that would be expected in an individual that did not receive the small interfering RNA. In one embodiment, the viral infection comprises a hepatitis C virus, such as HCV genotype 1a. In some embodiments, the virus is selected from the group consisting of hepatitis C genotypes 1a, 1b, 2a, and 2b. In some embodiments, the small interfering RNA comprises, consists of, or consists essentially of any of the shRNA or siRNA sequences described herein as well as sequences located within five nucleotides of one of the siRNA or shRNA sequences described herein. In some embodiments, the small interfering RNA is complementary to a viral sequence of about 19 to about 30 nucleotides, or about 19 to about 25 nucleotides, for example, any of about 19, 20, 21, 22, 23, 24, 25, 26, 27, 28, 29, or 30 nucleotides. In one embodiment, the virus is a hepatitis C virus, such as HCV genotype 1a. In one embodiment, the small interfering RNA binds to a sequence of about 19 to about 25 nucleotides within the IRES region of HCV 1a depicted in SEQ ID NO:26. Treatment may include therapy (e.g., amelioration or decrease in at least one symptom of infection) or cure. In some embodiments, the shRNA is administered parenterally, for example, by intravenous injection or infusion.

In another aspect, the invention provides a method of inhibiting gene expression in a virus, comprising contacting viral RNA or viral mRNA with a small interfering RNA or introducing a small interfering RNA into a virus-containing cell, such that the small interfering RNA, e.g., shRNA or siRNA, contains a sequence that is at least partially complementary to a polynucleotide sequence of the virus and capable of inhibiting viral gene expression, for example, by inducing cleavage of viral polynucleotide sequences. In some embodiments, the small interfering RNA comprises, consists of, or consists essentially of any one of the shRNA or siRNA sequences described herein. In some embodiments, the small interfering RNA binds to a viral sequence of about 19 to about 30 nucleotides, or about 19 to about 25 nucleotides, for example, any of about 19, 20, 21, 22, 23, 24, 25, 26, 27, 28, 29, or 30 nucleotides. In one embodiment, the virus is a hepatitis C virus, such as HCV 1a. In one embodiment, the small interfering RNA interacts with a sequence of about 19 to about 30 nucleotides within the IRES region of HCV genotype 1a depicted in SEQ ID NO:26 as well as sequences located within five nucleotides of one of the siRNA or shRNA sequences described herein. In yet other embodiments, at least two small interfering RNAs are introduced into a cell.

The invention also relates to an RNA sequence that consists of (a) a first RNA sequence, such that the first RNA sequence is a sequence illustrated in FIG. 10 or FIG. 16A-B, e.g., SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51; SEQ ID NO:52, SEQ ID NO:53, SEQ ID NO:54, SEQ ID NO:55, SEQ ID NO:56, or a sequence that differs from a foregoing sequence by one, two, or three nucleotides; (b) a second RNA sequence that is a complement of the first sequence; (c) a loop sequence positioned between the first and second nucleic acid sequence, the loop sequence consisting of 4-10 nucleotides; and (d) optionally, a two nucleotide overhang. In some embodiments of the invention, the first RNA sequence is SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51; SEQ ID NO:52, SEQ ID NO:53, SEQ ID NO:54, SEQ ID NO:55, or SEQ ID NO:56. The RNA sequence can, in some cases, include at least one modified nucleotide. The loop sequence of an RNA sequence of the invention can be, e.g., four nucleotides, five nucleotides, six nucleotides, seven nucleotides, eight nucleotides, nine nucleotides, ten nucleotides, or at least ten nucleotides. In some embodiments, the RNA sequence is an shRNA and includes an HCV target sequence as described herein and a complementary sequence, linked by a loop that includes at least one non-nucleotide molecule. In certain embodiments, the loop of the RNA sequence is 3' to a sense strand and 5' to the complementary antisense strand of the shRNA. In other embodiments, the loop of the RNA sequence is 3' to an antisense strand and 5' to the complementary sense strand of the shRNA. In some cases, the RNA sequence includes a two nucleotide overhang and the two nucleotide overhang is a 3'UU. In some cases, the overhang is one nucleotide, two nucleotides, three nucleotides, or more. In some cases, the first RNA sequence is any one of SEQ ID NOs:57-79, SEQ ID NO:12, SEQ ID NO:16, SEQ ID NO:17, or SEQ ID NO:18. In some cases, the RNA sequence is a sequence illustrated in FIG. 16A-B.

The invention also relates to a DNA sequence that includes a sequence encoding an RNA sequence disclosed herein (e.g., an RNA sequence illustrated in FIG. 10 or FIG. 16A-B). The invention also includes an expression vector comprising such a DNA sequence. Also included is a retroviral vector that includes such a DNA sequence, e.g., a retroviral vector that, upon infection of a cell with the vector, can produce a provirus that can express an RNA sequence of the invention, for example, without limitation, an shRNA sequence illustrated in FIG. 16A-B.

In some aspects, the invention relates to a composition that includes an RNA sequence as disclosed herein (for example, without limitation, an shRNA illustrated by FIG. 16A-B) and a pharmaceutically acceptable excipient. In some embodiments, the composition comprises a vector as disclosed herein and a pharmaceutically acceptable excipient. In certain embodiments, a composition of the invention includes at least two RNA sequences as disclosed herein.

In another aspect, the invention includes a method of inhibiting expression or activity of a hepatitis C virus. The method includes providing a cell that can express a hepatitis C virus, and contacting the cell with an RNA sequence as disclosed herein (non-limiting examples of which are illustrated in FIG. 16A-B). The cell can be in a mammal, e.g., a human or a non-human primate such as a chimpanzee. In certain embodiments, the cell is contacted with at least two different RNA sequences.

In some aspects, the invention relates to a method that includes identifying a subject infected with or suspected of being infected with a hepatitis C virus, providing to the subject a therapeutically effective amount of a composition containing one or more different RNA sequences disclosed herein. In some embodiments, the method also includes determining whether the viral load of the subject is decreased subsequent to providing the composition to the subject. In some embodiments, the method also includes determining whether at least one viral protein or viral nucleic acid sequence is decreased in the subject subsequent to providing the composition to the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DESCRIPTION OF THE DRAWINGS

FIG. 1A is a representation of the IRES nucleotide sequence of hepatitis C genotype 1a (see GenBank Accession No. AJ242654). Nucleotides of a target region, 344-374, are underlined. Various regions (indicated in bold) have been successfully targeted by inhibitors, including Heptazyme™ ribozyme (siRNA.com; positions 189-207), Chiron 5U5 siRNA [25] (positions 286-304), ISIS 14803 phosphorothioate antisense oligonucleotide [34] (positions 330-349), Mizusawa 331 siRNA [15] (positions 322-340) and a phosphorodiamidate morpholino oligomer [8, 35] (positions 344-363). A more complete list of siRNAs that have been tested to down-regulate the HCV IRES and other HCV elements can be found in [2, 3].

FIG. 1B is a representation of RNA sequences of shRNA HCVa-wt (shRNA1) and mutated variants thereof resulting from pol III transcription from a U6 promoter of corresponding DNA templates. Two base pairs (underlined) of HCVa-wt were altered to create versions of HCVa-wt containing 1 (HCVSNP1 or HCVSNP2) or 2 mismatches (HCVa-mut) shRNAs as shown.

FIG. 2D is a line graph depicting the resulting of experiments testing dose response of inhibition of HCV-IRES-driven gene expression by HCVa-wt and mutated (HCVa-mut) or control (229) shRNAs. Experimental conditions were as described for FIG. 2A. The data are represented as luciferase divided by SEAP normalized to 100. All data are the results of individual, independent experiments performed in triplicate.

FIG. 10 is a table depicting sequences and results of a screen of shRNAs for the ability to inhibit HCV IRES-mediated gene expression in 293FT cells. Cells were cotransfected (using Lipofectamine™ 2000) with pCDNA3/HCV IRES dual luciferase reporter construct (40 ng), pSEAP2 (25 ng, as a transfection and specificity control), and an shRNA (at 1 or 5 nM) in a well of a 48-well tissue culture plate. Plasmid pUC18 was added to provide a total of 400 ng nucleic acid per well. Forty-eight hours post-transfection, the supernatants were removed for SEAP analysis, cells were lysed, and firefly luciferase activity was measured by a luminometer. All data are the results of at least two independent experiments performed in triplicate. SEAP levels were uniform in all samples. Control experiments to assay specificity of shRNAs were performed on mutated pCDNA3/HCV IRES dual luciferase reporter construct as well, where C340 (in IRES) was substituted with U.

FIG. 16A-B is a table depicting shRNA sequences targeting HCV IRES as indicated. ShRNA loops are underlined. Nucleotides indicated by low-case are non-complementary to the target.

DETAILED DESCRIPTION OF THE INVENTION

Figure 1C:
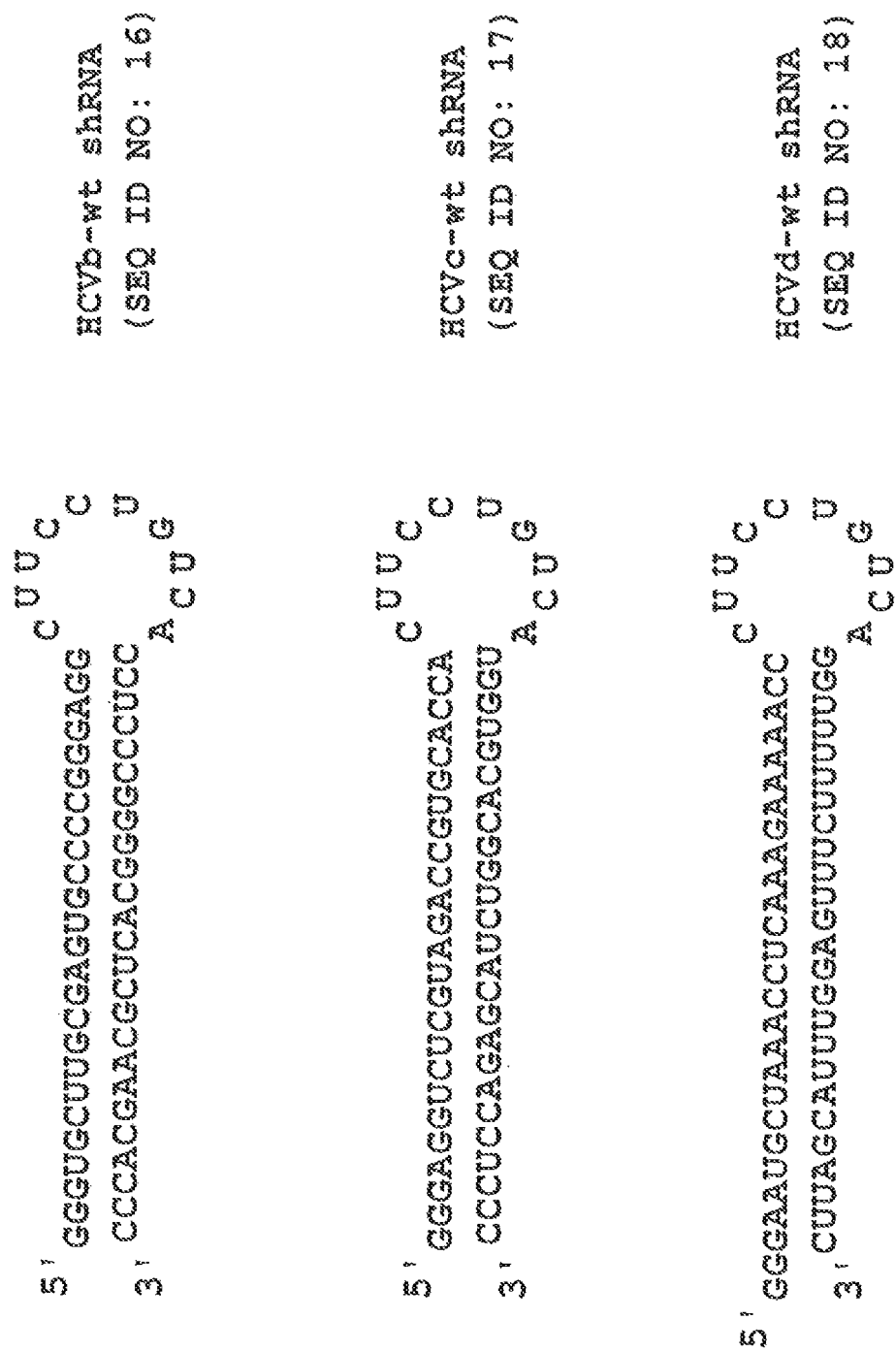
FIG. 1C is a representation of the sequences of shRNAs HCVb-wt (sh9), HCVc-wt (sh10), and HCVd-wt (sh11).
Figure 1D:
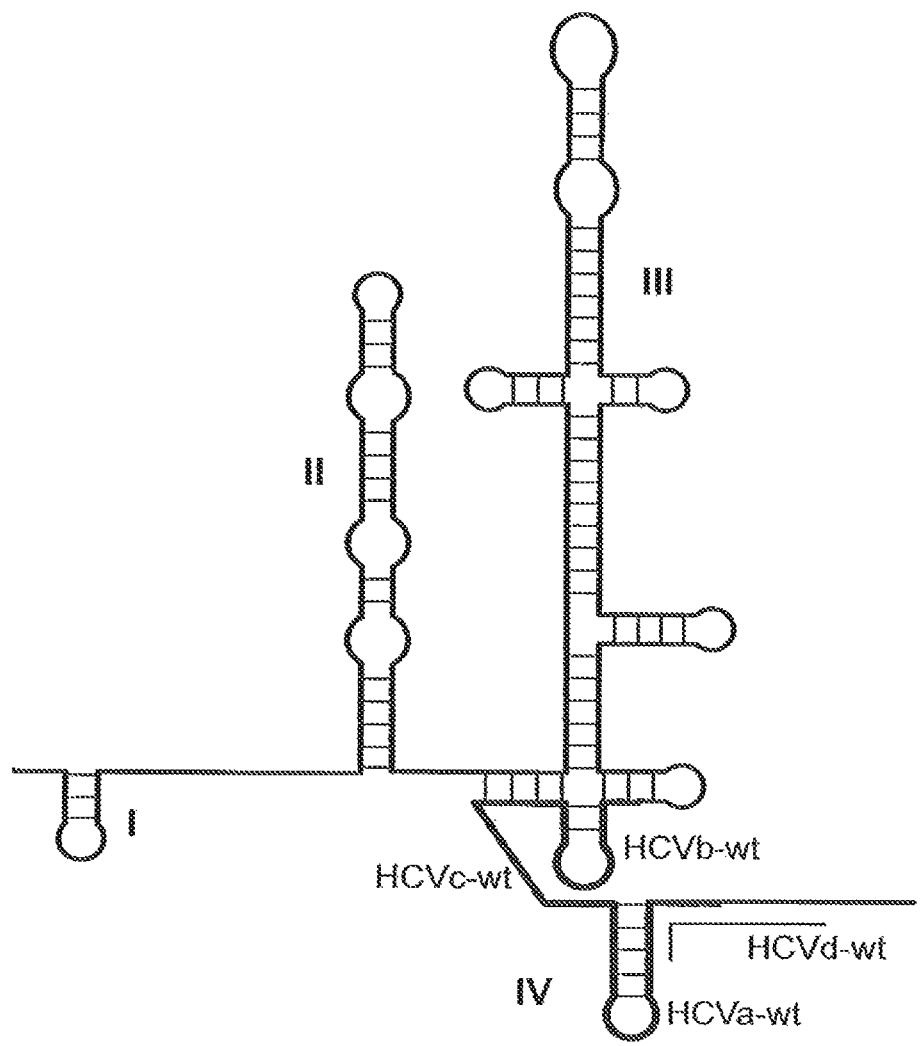
FIG. 1D is a representation of the secondary structure of the HCV IRES with indicated target sites for shRNA HCVa-wt, HCVb-wt, HCVc-wt, and HCVd-wt.

The invention provides compositions, methods, and kits for inhibiting viral (e.g., hepatitis C) gene expression and/or treating a viral infection in a mammal.

RNA interference offers a novel therapeutic approach for treating viral infections. The present invention provides small interfering RNAs (e.g., shRNAs and siRNAs) that target a viral sequence and inhibit (i.e., reduce or eliminate) viral gene expression, and methods of using such small interfering RNAs for treatment of a viral infection in a mammal, such as a human. In some embodiments, the small interfering RNA constructs of the invention inhibit gene expression of a virus by inducing cleavage of viral polynucleotide sequences within or near the target sequence that is recognized by the antisense sequence of the small interfering RNA.

As used herein, "small interfering RNA" refers to an RNA construct that contains one or more short sequences that are at least partially complementary to and can interact with a polynucleotide sequence of a virus. Interaction may be in the form of a direct binding between complementary (antisense) sequences of the small interfering RNA and polynucleotide sequences of the viral target, or in the form of an indirect interaction via enzymatic machinery (e.g., a protein complex) that allows the antisense sequence of the small interfering RNA to recognize the target sequence. In some cases, recognition of the target sequence by the small interfering RNA results in cleavage of viral sequences within or near the target site that is recognized by the recognition (antisense) sequence of the small interfering RNA. The small interfering RNA can exclusively contain ribonucleotide residues, or the small interfering RNA can contain one or more modified residues, particularly at the ends of the small interfering RNA or on the sense strand of the small interfering RNA. The term "small interfering RNA" as used herein encompasses shRNA and siRNA, both of which are understood and known to those in the art to refer to RNA constructs with particular characteristics and types of configurations.

As used herein, "shRNA" refers to an RNA sequence comprising a double-stranded region and a loop region at one end forming a hairpin loop. The double-stranded region is typically about 19 nucleotides to about 29 nucleotides in length on each side of the stem, and the loop region is typically about three to about ten nucleotides in length (and 3'- or 5'-terminal single-stranded overhanging nucleotides are optional). One example of such an shRNA, HCVa-wt shRNA, has a 25 base pair double-stranded region (SEQ ID NO:12), a ten nucleotide loop, a GG extension on the 5' end, and a UU extension on the 3' end. Additional examples of suitable shRNAs for use in, e.g., inhibiting HCV expression, are provided throughout the specification, e.g., FIG. 16A-B.

As used herein, "siRNA" refers to an RNA molecule comprising a double-stranded region with a 3' overhang of non-homologous residues at each end. The double-stranded region is typically about 18 to about 30 nucleotides in length, and the overhang may be of any length of nonhomologous residues, for example, 2, 3, 4, 5, 6, 7, 8, 9, 10, 11, 12, 13, 14, 15, 16 or more nucleotides. The siRNA can also comprise two or more segments of 19-30 base pair separated by unpaired regions. Without committing to any specific theory, the unpaired regions may function to prevent activation of innate immunity pathways. One example of such an siRNA is HCVa-wt siRNA, which has a 25 base pair double-stranded region (SEQ ID NO:12), and a UU extension on each 3' end.

In one embodiment, a small interfering RNA as described herein comprises a sequence complementary to a sequence of the internal ribosome entry site (IRES) element of hepatitis C ("HCV"). In one embodiment, the virus is HCV genotype 1a.

SiRNA gene inhibition has been shown to robustly inhibit gene expression in a number of mammalian systems. Due to its high level of secondary structure, the HCV IRES has been suggested to be a poor target for siRNAs or shRNAs. Mizusawa reported, however, successful targeting of the HCV IRES in 293 and Huh7 tissue culture cells, reporting 50 and 74 percent knock-down of gene expression, respectively. Similarly, Seo and coworkers [25] reported the ability of 100 nM siRNA to inhibit HCV replication (about 85% knock-down) in 5-2 Huh7 cells. It has now been demonstrated as described herein that small interfering RNAs (shRNAs and siRNAs) directed against the 3' end of the HCV IRES, including and downstream of the AUG translation start site, can induce 96 percent knockdown of HCV IRES-dependent luciferase expression at 0.3 nM in 293FT cells and 75 percent knockdown at 0.1 nM in Huh7 cells (see FIGS. 2D and 3A). Furthermore, direct delivery of shRNA to mouse liver was shown to potently inhibit HCV IRES-dependent reporter expression. This is the first demonstration of RNAi-mediated gene inhibition in an animal model following direct delivery of an RNA hairpin (not expressed in vivo from a plasmid or viral vector). The effectiveness of shRNA delivered directly to mouse liver following hydrodynamic injection was surprising in view of the high levels of nucleases found in blood. The observation that these shRNAs effectively knocked down gene expression in liver indicates that these shRNA inhibitors (1) are very potent and not needed at high levels in mouse liver to cause gene inhibition, (2) are delivered sufficiently rapidly to the liver, e.g., before they are cleaved by nucleases in quantities that prevent an inhibitory effect, or (3) are inherently stable to nuclease degradation (or a combination of these characteristics).

Reports suggest that in vitro-synthesized transcripts from bacteriophage promoters potently induce interferon (IFN) alpha and beta due to the presence of an unnatural 5' triphosphate [26]. Furthermore, shRNAs expressed from pol III expression vectors may also induce IFN [27]. How this interferon induction would affect use of shRNAs in a clinical setting for HCV infection is unclear. Current HCV therapy includes treatment with interferon alpha, suggesting that if interferon is induced by shRNA, it may have a positive effect. To date, no interferon-related side effects appear to have been reported in animals following administration of RNAi [3]. Additional concerns have been raised regarding off-target effects of siRNA as well as potential cytotoxic effects when siRNAs or shRNAs are delivered by lentiviral vectors [28].

The present invention also relates to methods of testing siRNAs and shRNAs targeting HCV IRES sequences to identify those sequences having sufficient activity (e.g., the highest activity among a selected group of such sequences) to be a candidate for use as a treatment. Testing can also include screening for small interfering activities having undesirable off-target effects or general cytotoxic effects. Off-target effects include, without limitation knockdown of nontargeted genes, inhibition of expression of non-targeted genes, and competition with natural microRNA pathways (Birmingham et al., Nat. Methods. 2006 3(3):199-204; Grimm et al., Nature 2006 441(7092):537-541). Methods of identifying cytotoxic effects are known in the art (for example, Marques et al., Nat. Biotechnol. 2006 24(5):559-565; Robbins et al., Nat. Biotechnol. 2006 24(5):566-571).

The IRES region in the HCV 5'-UTR is highly conserved (92-100% identical [15, 29-31]) and has several segments that appear to be invariant, making the IRES a prime target for nucleic acid-based inhibitors. The region around the AUG translation initiation codon is particularly highly conserved, being invariant at positions +8 to −65 (with the exception of a single nucleotide variation at position −2) as observed in over 81 isolates from various geographical locations [32]. Despite the conservation of sequence in the IRES motif, it is unlikely that targeting a single sequence, even if highly conserved, will be sufficient to prevent escape mutants. RNA viruses are known to have high mutation rates due to the high error rate of the RNA polymerase and the lack of proofreading activity of that enzyme. On average, each time HCV RNA is replicated one error is incorporated into the new strand. This error rate is compounded by the prodigious production of viral particles in an active infection (approximately a trillion per day in a chronically infected patient) [33]. Therefore, in some embodiments of the invention, several conserved sites are targeted or, alternatively, shRNAs as described herein are used as a component of a combination treatment, such as with ribaviran and/or pegylated interferon. As demonstrated herein, a single mismatch does not completely block shRNA activity (see Example 2; FIG. 2D); thus each different shRNA may have some activity against a limited number of mutations. Accordingly, the invention includes methods of inhibiting HCV expression using an shRNA that may include a mismatch to the target sequence. The invention also includes methods of inhibiting HCV expression by administering at least two different shRNAs targeting an HCV IRES, such that the shRNAs differ in the targeting sequences.

McCaffrey and colleagues reported that a phosphorodiamidate morpholino oligonucleotide directed against a conserved HCV IRES site at the AUG translation initiation site potently inhibits reporter gene expression [8]. The same morpholino inhibitor was used for comparison against the shRNA inhibition described herein. It was found that both the morpholine and the shRNA targeting the conserved HCV IRES site potently and robustly inhibited IRES-dependent gene expression. Four mutations in the morpholino were required to block activity, whereas two changes in the shRNA were sufficient, suggesting greater shRNA specificity. This potential advantage, coupled with the lack of unnatural residues in the shRNA inhibitor and presumably fewer resultant side effects, are balanced by the increased stability of the morpholino oligomer.

A dual reporter luciferase plasmid was used in which firefly luciferase (fLuc) expression was dependent on the HCV IRES [24]. Expression of the upstream *renilla* luciferase is not HCV IRES-dependent and is translated in a Cap-dependent process. Direct transfection of HCV IRES shRNAs, or alternatively shRNAs expressed from polIII-promoter vectors, efficiently blocked HCV IRES-mediated fLuc expression in human 293FT and Huh7 cells. Control shRNAs containing a double mutation had little or no effect on fLuc expression, and shRNAs containing only a single mutation showed partial inhibition. These shRNAs were also evaluated in a mouse model where DNA constructs were delivered to cells in the liver by hydrodynamic transfection via the tail vein. The dual luciferase expression plasmid, the shRNAs, and secreted alkaline phosphatase plasmid were used to transfect cells in the liver, and the animals were imaged at time points over 12 to 96 hours. In vivo imaging revealed that HCV IRES shRNA directly, or alternatively expressed from a polIII-plasmid vector, inhibited HCV IRES-dependent reporter gene expression; mutant or irrelevant shRNAs had little or no effect. These results indicate that shRNAs, delivered as RNA or expressed from viral or nonviral vectors, are useful as effective antivirals for the control of HCV and related viruses.

Assay of three additional shRNAs targeting different sites on HCV IRES domain IV revealed another potent shRNA, HCVd-wt, whose target position is shifted six nucleotides from that of HCVa-wt. HCVb-wt and HCVc-wt were much less efficient inhibitors.

To further investigate local sequence effects on potency, seven in vitro-transcribed shRNA constructs comprising a 19 base pair sequence complementary to a sequence of the HCV IRES and the corresponding synthetic siRNA comprising the same 19 base pair sequences, targeting all possible positions within the 25 base pair site of HCVa-wt (344-368), were assayed for inhibitory activity. A 25 base pair synthetic siRNA corresponding to HCVa-wt shRNA was also tested. All of the tested constructs exhibited a high level of activity. In general, 19 base pair siRNAs were more potent than 19 base pair shRNAs. The most potent, siHCV19-3 was effective at 1 nM (>90% inhibition), 0.1 nM (about 90% inhibition) and even at a concentration of 0.01 nM (about 40% inhibition). Thus, 19-25 base pair shRNAs and siRNAs designed to target the region 344-374 on the HCV IRES are generally potent inhibitors of HCV expression, with some local differences.

Small hairpin RNAs of the invention can, optionally, include structures resulting in strong noncovalent bonds between the sense and antisense strands of the shRNA. Examples of such noncovalent bonds include cross-links mediated by metal ions. Such cross-links can be formed between natural or modified nucleotide residues, including, for example, modified bases, sugars, and terminal groups, as described in Kazakov and Hecht 2005, Nucleic Acid-Metal Ion Interactions. In: King, R. B. (ed.), *Encyclopedia of Inorganic Chemistry.* 2nd ed., Wiley, Chichester, vol. VI, pp. 3690-3724, e.g., section 5.4.3. Additional non-limiting examples of variants of such bonds are found patent application WO 99/09045 (US2006074041; e.g., FIG. 10. In general the location of cross-linkable nucleotide residues is at the ends of the complementary RNA strands that lie in close proximity upon duplex formation. The addition of certain metal ions (or metal ion coordination compounds) can result in the cross-linking of functional groups that have strong affinity for these metal ions, such as —SH, —SCH3, phosphorothioates, imidazolides, o-phenanthrolines, and others. These modified nucleotides are introduced during chemical synthesis of the sense and antisense RNA strands. The modified nucleotides in sense and antisense strands may either form base pairs or be part of 1-3 nucleotide overhangs.

Targeting Sequences

Examples of targeting sequences are provided throughout the specification. Non-limiting examples of targeting sequences are provided in, for example, Table 1 and FIG. 10. Non-limiting examples of shRNAs and siRNAs incorporating targeting sequences are found throughout the specification, e.g., in FIG. 1 and FIG. 16A-B.

Loops

Effects of size and sequence of loop region of the shRNA were also investigated. The loop region of the shRNA stem-loop can be as small as two to three nucleotides and does not have a clear upper limit on size; generally, a loop is between four and nine nucleotides, and is generally a sequence that does not cause unintended effects, e.g., by being complementary to a non-target gene. Highly structured loop sequences such as a GNRA tetraloop can be used in the loop region (e.g., as the loop) in an shRNA. The loop can be at either end of the molecule; that is, the sense strand can be either 5' or 3' relative to the loop. Also, a noncomplementary duplex region (approximately one to six base pairs, for example, four CG base pairs) can be placed between the targeting duplex and the loop, for example to serve as a "CG clamp" to strengthen duplex formation. At least 19 base pairs of target-complementary duplex are needed if a noncomplementary duplex is used.

A loop structure can also include reversible linkages such as S—S bonds, which can be formed by oxidation of —SH groups introduced into nucleotide residues, e.g., as described in (Earnshaw et al., J. Mol. Biol., 1997, 274: 197-212; Sigurdsson et al. (Thiol-Containing RNA for the Study of Structure and Function of Ribozymes. METHODS: A Companion to Methods in Enzymology, 1999, 18: 71-77). A non-limiting example of the location for nucleotide residues with SH groups is at the ends of the complementary RNA strands that lie in close proximity upon duplex formation. Such modified nucleotides are introduced during chemical synthesis of the sense and antisense RNA strands of the small interfering RNA. The modified nucleotides in sense and antisense strands may either form base pairs or form non-complementary overhangs of one to three nucleotides.

Additional non-limiting examples of loops and their applications, e.g., in shRNA and siRNA targeting HCV, can be found in the Examples.

Termini

The 3' terminus of an shRNA as described herein can have a non-target-complementary overhang of two or more nucleotides, for example, UU or dTdT, however, the overhangs can be any nucleotide including chemically modified nucleotides that, for example, promote enhanced nuclease resistance. In other embodiments, there are one or zero nucleotides overhanging on the 3' end.

The 5' end can have a noncomplementary extension, e.g., two Gs (as shown in FIG. 1B), a GAAAAAA sequence, or only one or zero nucleotides extending beyond the target-complementary duplex region. In the sequence shown in FIG. 1B, the two 5' G's are included primarily for ease of transcription from a T7 promoter.

Additional Features

Additional features that can optionally be included in shRNAs used to inhibit HCV expression and that are encompassed by the invention are length variations between about 19 base pairs and about 30 base pairs for the target complementary duplex region, small shifts in the sequence targeted (generally zero to about two nucleotides, and shifts as large as about ten nucleotides in either direction along the target may lie within the targetable region). Similarly, mismatches are also tolerated: about one to about two in the antisense strand and about one to about nine in the sense strand (the latter destabilizing the hairpin duplex but not affecting the strength of binding of the antisense strand to the target; the number tolerated depends partly on the length of the target-complementary duplex. As described herein, an shRNA having at least seven G-U mismatches within a 29 base pair target-complementary duplex region can be used successfully for inhibiting HCV expression, e.g., using sequence targeting the HCV IRES. Note that the two mutations shown in FIG. 1B largely abrogated inhibition, but other mutants having mutations in other positions, particularly if they are closely spaced and/or near the end, can be better tolerated. Certain variations are known in the art or demonstrated in the instant application.

Vectors

Suitable vectors for producing shRNAs and siRNAs are described herein and are known in the art. In non-limiting examples, shRNAs can be expressed using Pol III promoters such as U6 or H1, in the context of vectors derived from adeno-associated virus or lentiviruses. The human U6 nuclear RNA promoter and human H1 promoter are among the pol III promoters for expressing shRNAs.

One feature that is generally desirable in a vector is relatively prolonged transgene expression. Lentiviral vectors are able to transduce nondividing cells and maintain sustained long-term expression of transgene. Adeno-associated virus serotype 8 is considered safe and is characterized by prolonged transgene expression.

Candidate shRNA and siRNA

In some cases, one or more small interfering RNAs are identified as having activity for inhibiting a targeted virus such as HCV. Additional tests can be carried out to further characterize the suitability of such RNAs for use, e.g., for inhibiting HCV expression in an animal. Animal models can be used for such testing. One non-limiting examples includes a mouse model, e.g., as illustrated in Example 3 (infra). Other animal models suitable for testing an treatment for HCV are known in the art, for example, using chimpanzees.

Methods

The invention relates to methods of inhibiting gene expression in a virus, comprising contacting the virus with a small interfering RNA, such as a shRNA or siRNA as described herein that comprises a sequence that is at least partially complementary to, and is capable of interacting with a polynucleotide sequence of the virus. In some embodiments, contacting the virus comprises introducing the small interfering RNA into a cell that contains the virus, i.e., a virus infected cell. "Inhibiting gene expression" as used herein refers to a reduction (i.e., decrease in level) or elimination of expression of at least one gene of a virus. For example, reduction in expression compared to corresponding cell or animal infected with the virus. In some embodiments, inhibition of gene expression is accomplished by cleavage of the viral target sequence to which the small interfering RNA binds. Gene expression can be assayed by assaying viral RNA or viral protein. In some cases, efficacy of a method (for example, a treatment using a composition described herein) is assayed by evaluating an infected animal for a decrease in symptoms or a change (e.g., decrease) in the expression or activity of a protein associated with viral infection, e.g., a viral protein such as p24, or a host protein such as an interferon.

The invention also relates to methods for treating a viral infection or for treating a subject suspected of being infected (including a subject exposed to virus for prophylactic treatment) in a mammal, comprising administering to the mammal a composition comprising a therapeutically effective amount of a small interfering RNA, such as a shRNA or siRNA as described herein that includes a sequence that is at least partially complementary to, and capable of interacting with (e.g., hybridizing to under physiological conditions, or effecting RNAi activity), a polynucleotide sequence of the virus, e.g., the IRES sequence of HCV. In some embodiments, the mammal is human. In one embodiment, the mammal is a human and the viral infection is a HCV infection, such as an infection with HCV genotype 1a, and the small interfering RNA comprises a sequence that is at least complementary to a sequence of the IRES of the HCV.

As used herein, a "therapeutically effective amount" is an amount of a small interfering RNA that can render a desired therapeutic outcome (e.g., reduction or elimination of a viral infection). A therapeutically effective amount may be administered in one or more doses. Non-limiting examples of doses are about 0.1 mg/kg to about 50 mg/kg, e.g., about 1 to about 5 mg/kg. Suitable methods of delivery are known in the art and include, for example, intravenous administration (e.g., via a peripheral vein of via a catheter). Non-limiting examples include delivery via the hepatic artery or the portal vein.

Generally, in methods for treating a viral infection in a mammal, the small interfering RNA is administered with a pharmaceutically acceptable carrier. As used herein, a "pharmaceutically acceptable carrier" (also interchangeably termed "pharmaceutically acceptable excipient" herein) is a relatively inert substance that facilitates administration of the small interfering RNA or RNAs. For example, a carrier can give form or consistency to the composition or can act as a diluent. A pharmaceutically acceptable carrier is biocompatible (i.e., not toxic to the host) and suitable for a particular route of administration for a pharmacologically effective substance. Suitable pharmaceutically acceptable carriers include but are not limited to stabilizing agents, wetting and emulsifying agents, salts for varying osmolarity, encapsulating agents, buffers, and skin penetration enhancers. In some embodiments, the pharmaceutically acceptable carrier is water or saline. Examples of pharmaceutically acceptable carriers are described in *Remington's Pharmaceutical Sciences* (Alfonso R. Gennaro, ed., 18th edition, 1990).

In methods for treating a viral infection, small interfering RNAs as described herein are generally administered parenterally, e.g., subcutaneously, intravenously, or intramuscularly.

Compositions

The invention provides compositions for inhibiting viral gene expression and/or treating a viral infection in a mammal comprising at least one small interfering RNA as described herein. Compositions of the invention may comprise two or more small interfering RNAs as described herein. In accordance with the invention, a small interfering RNA, e.g., shRNA or siRNA, comprises a sequence that is substantially complementary to a viral polynucleotide sequence of about 19 to about 30 nucleotides, wherein interaction of the substantially complementary sequence of the small interfering RNA with the polynucleotide sequence of the virus inhibits viral gene expression, for example, by cleavage of viral polynucleotide sequences.

In some embodiments, the composition comprises an shRNA that includes a sequence selected from the group consisting of SEQ ID NOs: 12, 17, 18, 19, 20, 21, 22, 23, 24, and 25. In some embodiments, the composition comprises an shRNA that includes one of the following: SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51; SEQ ID NO:52, SEQ ID NO:53, SEQ ID NO:54, SEQ ID NO:55, or SEQ ID NO:56 (Table 10). In some embodiments, the composition comprises one or more shRNAs of SEQ ID NO:57-110. In some embodiments, the composition comprises a siRNA comprising a sequence selected from SEQ ID NOs: 19, 20, 21, 22, 23, 24, and 25. In other embodiments, the composition comprises a siRNA that includes a sequence of SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51; SEQ ID NO:52, SEQ ID NO:53, SEQ ID NO:54, SEQ ID NO:55, or SEQ ID NO:56 (FIG. 10). In some embodiments, the composition comprises a shRNA or siRNA that binds to, i.e., comprises a sequence substantially complementary to, a sequence of about 19 to about 30 nucleotides within the IRES element of HCV, for example, HCV genotype 1a. A composition can include more than one different shRNA, e.g., shRNAs targeting different sequences of an IRES or different alleles or mutations of a target sequence. An shRNA or siRNA as described herein can include more than one of the identified sequences. Certain compositions contain more than one different shRNA or siRNA sequences.

In some embodiments, the invention provides a pharmaceutical composition comprising a small interfering RNA as described herein and a pharmaceutically acceptable carrier. In some embodiments, the pharmaceutical composition is formulated for parenteral administration to a mammal, for example, a human.

A pharmaceutical composition that includes a short interfering RNA (e.g., an siRNA or an shRNA) is formulated to be compatible with its intended route of administration. Examples of routes of administration include parenteral, e.g., intravenous, intradermal, subcutaneous, inhalation, transdermal (topical), transmucosal, and rectal administration; or oral. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the selected particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some cases, isotonic agents are included, for example, sugars, or polyalcohols such as mannitol, sorbitol, or sodium chloride. Prolonged absorption of an injectable composition can be effected by including in the composition an agent which delays absorption, for example, aluminum monostearate or gelatin.

Sterile injectable solutions can be prepared by incorporating the active compound in the specified amount in an appropriate solvent with one or a combination of ingredients enumerated above, as needed, followed by filtered sterilization. Generally, dispersions are prepared by incorporating the active compound into a sterile vehicle that contains a basic dispersion medium and other ingredients selected from those enumerated above or others known in the art. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the selected pharmaceutical carrier.

Toxicity and therapeutic efficacy of compounds disclosed herein can be determined by pharmaceutical procedures known in the art, for example, in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The invention also relates to a method of making a medicament for use in treating a subject, e.g., for HCV infection. Such medicaments can also be used for prophylactic treatment of a subject at risk for or suspected of having an HCV infection.

Kits

The invention provides kits comprising a small interfering RNA as described herein. In some embodiments, the kits also include instructions for use in the methods for inhibiting viral gene expression and/or methods for treatment of a viral infection in a mammal described herein. Instructions may be provided in printed form or in the form of an electronic medium such as a floppy disc, CD, or DVD, or in the form of a website address where such instructions may be obtained.

In some embodiments, the kits include a pharmaceutical composition of the invention, for example including at least one unit dose of at least one small interfering RNA such as a shRNA or a siRNA, and instructions providing information to a health care provider regarding usage for treating or preventing a viral infection. The small interfering RNA is often included as a sterile aqueous pharmaceutical composition or dry powder (e.g., lyophilized) composition.

Suitable packaging is provided. As used herein, "packaging" refers to a solid matrix or material customarily used in a system and capable of holding within fixed limits a composition of the invention suitable for administration to an individual. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Kits may also optionally include equipment for administration of a pharmaceutical composition of the invention, such as, for example, syringes or equipment for intravenous administration, and/or a sterile solution, e.g., a diluent such as water, saline, or a dextrose solution, for preparing a dry powder (e.g., lyophilized) composition for administration.

FIG. 16A-B illustrates examples of shRNAs containing sequence targeting HCV IRES, and tested using methods described herein.

EXAMPLES

The invention is further illustrated by the following examples. The examples are provided for illustrative purposes only. They are not to be construed as limiting the scope or content of the invention in any way.

Example 1

Design and Construction of shRNA Expression Cassettes, T7 Transcription Reactions, and Reporter Gene Assays Chemically synthesized oligonucleotides were obtained from IDT (Coralville, Iowa), resuspended in RNase- and pyrogen-free water (Biowhittaker), and annealed as described below. The following oligonucleotide pairs, for making shRNA, contain a T7 promoter element (doubly underlined), sense and antisense HCV IRES sequence and a miR-23 microRNA loop structure (reported to facilitate cytoplasmic localization [21, 22]).

T7-HCVa-wt fw:

(SEQ ID NO: 1)
5'-taatacgactcactatagggagcacgaatcctaaacctcaaaga

CTTCCTGTCAtctttgagg tttaggattcgtgctcTT-3';

TABLE 1

Listing of Targeting Sequences Disclosed in the Application that can be Incorporated into shRNA or siRNA and Examples of such shRNAs and siRNAs

| Sequence ID # | Antisense sequence (5'-3') | Target Position on HCV IRES | Examples of shRNA or siRNA |
|---|---|---|---|
| SEQ ID NO: 27 | UCUUUGAGGUUUAGGAUUCGUGCUC | 344-368 | HCVa-wt shRNA |
| SEQ ID NO: 28 | UCUUUGAGGUUUAGGAUUGGUGCUC | 344-368 | HCVa-SNP1 shRNA |
| SEQ ID NO: 29 | UCUUUGAGCUUUAGGAUUCGUGCUC | 344-368 | HCVa-SNP2 shRNA |
| SEQ ID NO: 30 | UCUUUGAGCUUUAGGAUUGGUGCUC | 344-368 | HCVa-mut shRNA |
| SEQ ID NO: 31 | CCUCCCGGGGCACUCGCAAGCACCC | 299-323 | HCVb-wt shRNA |
| SEQ ID NO: 32 | UGGUGCACGGUCUACGAGACCUCCC | 318-342 | HCVc-wt shRNA |
| SEQ ID NO: 33 | GGUUUUUCUUUGAGGUUUAGGAUUC | 350-374 | HCVd-wt shRNA |
| SEQ ID NO: 19 | AGGUUUAGGAUUCGUGCUC | 344-362 | siRNA#1, shRNA#1 |
| SEQ ID NO: 20 | GAGGUUUAGGAUUCGUGCU | 345-363 | siRNA#2, shRNA#2 |
| SEQ ID NO: 21 | UGAGGUUUAGGAUUCGUGC | 346-364 | siRNA#3, shRNA#3 |
| SEQ ID NO: 22 | UUGAGGUUUAGGAUUCGUG | 347-365 | siRNA#4, shRNA#4 |
| SEQ ID NO: 23 | UUUGAGGUUUAGGAUUCGU | 348-366 | siRNA#5, shRNA#5 |
| SEQ ID NO: 24 | CUUUGAGGUUUAGGAUUCG | 349-367 | siRNA#6, shRNA#6 |
| SEQ ID NO: 25 | UCUUUGAGGUUUAGGAUUC | 350-368 | siRNA#7, shRNA#7 |

T7-HCVa-wt rev:

(SEQ ID NO: 2)
5'-AAgagcacgaatcctaaacctcaaagaTGACAGGAAG tctttgaggtttaggattcgtgct ccctatagtgagtcgtatta-3'

(T7 promoter sequence doubly underlined). T7 transcripts for HCVa-mut shRNA were identical with the exception that nucleotide changes (G→C and C→G) were incorporated into the synthesized oligonucleotides at the singly underlined residues.

HCVa-wt shRNA (FIG. 1B) was designed to target the region 344-374 on the HCV IRES; HCVb-wt was designed to target the region 299-323 (FIG. 1C); HCVc-wt was designed to target the region 318-342 (FIG. 1C); and HCVd-wt was designed to target the region 350-374 (FIG. 1C).

ShRNAs #1-7 (targeting positions 344-362, 345-363, 346-364, 347-365, 348-366, 349-367, 350-368 on the HCV IRES; See FIG. 4A, which depicts the 19 base pair viral recognition sequences) were in vitro transcribed using the MEGAscript® kit (Ambion) and contained the same loop sequences and 5', 3'-overhangs as HCVa-wt shRNA. SiRNAs #1-7 (see FIG. 4A, which depicts the 19 base pair viral recognition sequences) were chemically synthesized at Dharmacon (Lafayette, Colo.) and contained 3'-UU overhangs on both sense and antisense strands.

The oligonucleotide pair used to prepare the control shRNA 229 (which targets tumor necrosis factor alpha) is 229-5'-TAATACGACTCACTATAGGGGCG GTGCCTAT-GTCTCAGCCTCTTCTCACTTCCTGTCAT-GAGAAGAGGCTGAGACA TAGGCACCGCC TT-3' (SEQ ID NO:3)
and 229-3'-AAGGCG GTGCCTATGTC TCAGCC TCT TCTCA TGACAGGAAG TGAGA AGAGGCTGA GACAT-AGGCACCCCTATAGTGAGTCGTATTA-5' (SEQ ID NO:4).

Pol III U6 shRNA Expression Vector Construction-Design of Small Hairpin shRNA Expression Vectors Oligonucleotide pairs were incubated together at 95° C. for two minutes in RNA polymerase buffer (e.g., 120 µl of each 100 µM oligonucleotide in 60 µl 5× annealing buffer (Promega; 1×=10 mM Tris-HCl (pH 7.5), 50 mM NaCl) and slowly cooled (annealed) over 1 hour to less than 40° C. The oligonucleotides were designed to provide 4-base overhangs for rapid cloning into Bbs1/BamH1-digested pCRII-U6 plasmid (Bbs1 and BamH1 recognition sites or overhangs are underlined in the oligonucleotide sequences). The pCRII-U6 pol III expression plasmid was prepared by subcloning the PCR product obtained from human HT-1080 genomic DNA using primers and huU6-5' ATCGATCCCCAGTGGAAA-GACGCGCAG (SEQ ID NO:5) and huU6-3'-GGATCCGAATTC GAAGACCACGGTGTTTCGTCCTTTCCACAA-5' (SEQ ID NO:6) [23] into the pCRII vector (Invitrogen) using the TA cloning kit (Invitrogen). The cassette consisting of the annealed oligonucleotides (encoding the HCV IRES shRNA) was ligated into the Bbs1/BamH1-digested pCRII-U6 plasmid. The expressed shRNA contains a miR-23 microRNA loop structure to facilitate cytoplasmic localization [21, 22]. The final pCRII-U6 constructs were confirmed by sequencing. The primers pairs used were: pHCVa-wt 5'-ACCG GAGCACGAATCCTAAACCTCAAAGA CTTC-CTGTCA TCTTTGAGGTTTAGGATTCGTGCTC TTTTTTG-3' (SEQ ID NO:7) and 5'-GATCCAAAAAA GAGCACGAATCCTAAACCTCAAAGA TGACAG-GAAG TCTTTGAGGTTTAGGATTCGTGCTC-3' (SEQ ID NO:8). Oligonucleotides containing the appropriate sequence changes at the underlined residues (see above) were used to generate the pCRII-U6/HCVa-mut (double mutation), HCVsnp1 (single change at 5' side) and HCVsnp2 (single change at 3' end) as depicted in FIG. 1B and described above. The control pCRII-U6/229 was prepared is similar fashion using the oligonucleotides 5'-ACCGGGCG GTGCCTAT-GTCTCAGCCTCTTCTCACTTCCTGTCATGAGA AGAGGCTGAGACATAGGCACCGCCTTTTTT-3' (SEQ ID NO:9) and 3'-GATCAAAAAAGGCGGTGCCTAT-GTCTCAGCCTCTTCTCATGACAGGAAGTGAG AAGAGGCTGAGACATAGGCACCGCC-5' (SEQ ID NO:10).

T7 Transcription Reactions

Oligonucleotide pairs were incubated at 95° C. for two minutes in RNA polymerase buffer (e.g., 120 µl of each 100 µM oligonucleotide in 60 µl 5× transcription buffer (Promega)) and slowly cooled (annealed) over 1 hour to less than 40° C. ShRNA was transcribed at 42° C. for four hours from 5 µM of the resulting annealed double-stranded DNA template using the AmpliScribe™ T7 Flash transcription kit (Epicentre Technologies) followed by purification on a gel filtration spin column (Microspin™ G-50, Amersham Biosciences) that had been thoroughly washed three times with phosphate buffered saline (PBS) to remove preservative.

siRNAs siRNAs were prepared by annealing chemically synthesized (Dharmacon) complementary strands of RNA, each containing the appropriate recognition sequence plus an (overhanging) UU extension on the 3'end.

Transfections and Reporter Gene Assays

Human 293FT (Invitrogen) and Huh7 cells (American Type Culture Collection (ATCC), Manassas, Va.) were maintained in DMEM (Biowhittaker®) with 10% fetal bovine serum (HyClone), supplemented with 2 mM L-glutamine and 1 mM sodium pyruvate. The day prior to transfection, cells were seeded at $1.7\times10^5$ cells/well in a 24-well plate, resulting in about 80% cell confluency at the time of transfection. Cells were transfected with Lipofectamine™ 2000 (Invitrogen, Carlsbad, Calif.) following the manufacturer's instructions. For the inhibition experiments, 293FT or Huh7 cells were cotransfected (in triplicate) with 40 ng pCDNA3/HCV IRES dual luciferase (renilla and firefly) reporter construct, 50 ng pSEAP2-control plasmid (BD Biosciences Clontech, as transfection controls) and the indicated amounts of T7-generated shRNA (typical amount 1 pmole) or pCRII-U6 shRNA expression construct (710 ng). Compensatory pUC18 plasmid was added to the transfection mix to give a final concentration of 800 ng total nucleic acid per transfection. Forty-eight hours later, supernatant was removed, heated at 65° C. for 15-30 minutes, and 5-10 µl of the supernatant was added to 150 µl p-nitrophenyl phosphate liquid substrate system (pNPP, Sigma). After a 30-60 minute incubation at room temperature, samples were read (405 nm) on a Molecular Devices Thermomax microplate reader and quantitated using SOFTmax software (Molecular Devices). The remaining cells were lysed and luciferase activity measured using the Dual-Luciferase Reporter assay system (Promega) and MicroLumat LB 96 P luminometer (Berthold).

Mice

Six-week old female Balb/c mice were obtained from the animal facility of Stanford University. Animals were treated according to the NIH Guidelines for Animal Care and the Guidelines of Stanford University.

Mouse Hydrodynamic Injections and In Vivo Imaging

Hydrodynamic tail vein injections were performed as described by McCaffrey and colleagues with minor modifications including omission of RNasin [24]. A total volume of 1.8 ml of phosphate-buffered saline containing inhibitor (RNA or plasmid), 10 µg of pHCV Dual Luc plasmid, and 2 µg pSEAP2-control plasmid (BD Biosciences Clontech, contains the SV40 early promoter), was steadily injected into the mouse tail vein over about five seconds (N=4-6 animals per group). At the indicated times, 100 of 30 mg/ml luciferin was injected intraperitoneally. Ten minutes following the injection, live anesthetized mice were analyzed using the IVIS7 imaging system (Xenogen Corp., Alameda, Calif.) and the resulting light emission data quantitated using LivingImage software (Xenogen). Raw values are reported as relative detected light per minute and standard errors of the mean for each group (N=4-5 animals) are shown.

Secreted Alkaline Phosphatase (SEAP) Assay

At day 5, mice were bled through the retro-orbital vein of the eye. The serum was separated from blood cells by microcentrifugation, heated at 65° C. for 30 minutes to inactivate endogenous alkaline phosphates, and 5-10 µl of the serum was added to 150 µl pNPP liquid substrate system (see above). After a 30-60 minute incubation at room temperature, samples were read (405 nm) and quantitated as described above.

Example 2 shRNA Inhibition of HCV IRES-Mediated Gene Expression in Human Tissue Culture Cells In this study, short interfering RNAs (shRNAs and siRNAs) designed and constructed as in Example 1 to target a conserved region of the hepatitis C IRES were tested for their ability to inhibit HCV IRES-mediated reporter expression in human tissue culture cells.

FIG. 1A shows the HCV IRES target site (panel A) as well as the HCV shRNA resulting from T7 transcription of a template prepared from hybridized oligonucleotides containing a T7 promoter sequence and HCV IRES target (FIG. 1B). The underlined residues are those that were changed to generate the mutant HCV shRNAs. The shRNAs contain a mir-23 microRNA loop structure that was previously suggested to facilitate cytoplasmic localization [21, 22] and a 25 base pair RNA stem with two nucleotides at the 5' (two guanines) and 3' (two uridines) ends that may also hybridize though non Watson-Crick G:U base pairings. For vector-delivered shRNAs, overlapping oligonucleotides were subcloned into a polIII expression vector (pCRII-U6, see Example 1).

Three other shRNAs were also designed with the same stem length and loop sequence that target nearby positions in Domain IV of the HCV IRES (FIG. 1C). HCVb-wt shRNA targets a highly structured region (used as negative control, to compare efficiency), while HCVc-wt and HCVd-wt shRNA target regions that are more 'accessible' according to biochemical footprinting studies (FIG. 1D; Brown et al., Nucleic Acids Res., 1992, 20:5041-5.). All RNAs were in vitro transcribed from dsDNA templates containing a T7 promoter, similar to the HCVa-wt shRNA.

To test the effectiveness of the HCV shRNAs to inhibit HCV IRES-mediated gene expression, human 293FT or hepatocyte Huh7 cells were co-transfected with pCDNA3/HCV IRES dual luciferase expression plasmid, secreted alkaline phosphatase expression plasmid (pSEAP2, to control for efficiency of transfection) as well as in vitro synthesized shRNAs or alternatively, pol III expression vectors containing the corresponding shRNA cassettes.

Figure 1E:
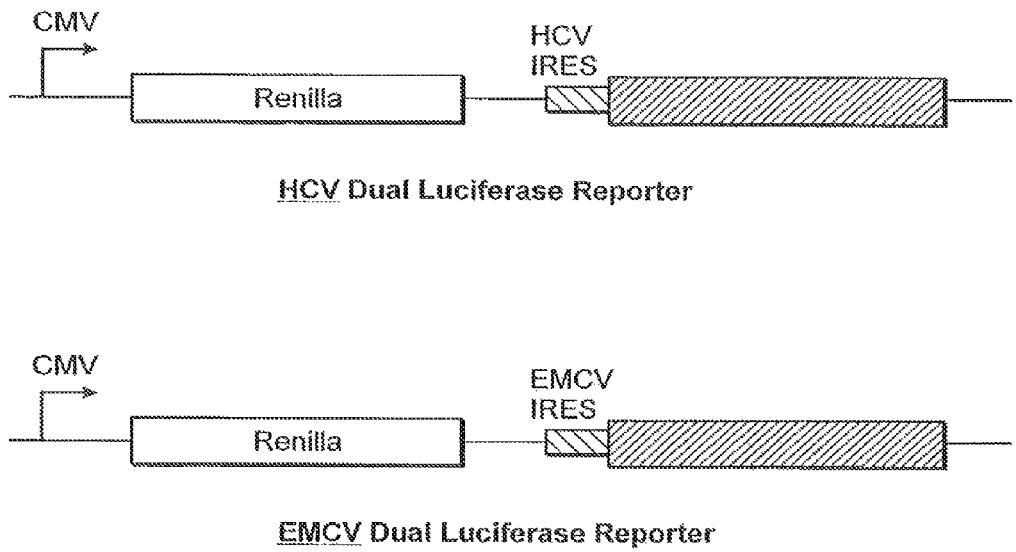
FIG. 1E is a schematic representation of the pCDNA3/HCV IRES dual luciferase reporter construct used to produce the HCV IRES target as well as the EMCV IRES control, in which the IRES from encephalomyocarditis virus replaces the HCV IRES and therefore lacks any target for the HCV-directed shRNAs. In each case, firefly luciferase expression is dependent on initiation of translation from the IRES sequence, whereas *Renilla* luciferase is expressed in a cap-dependent manner.
Figure 1F:
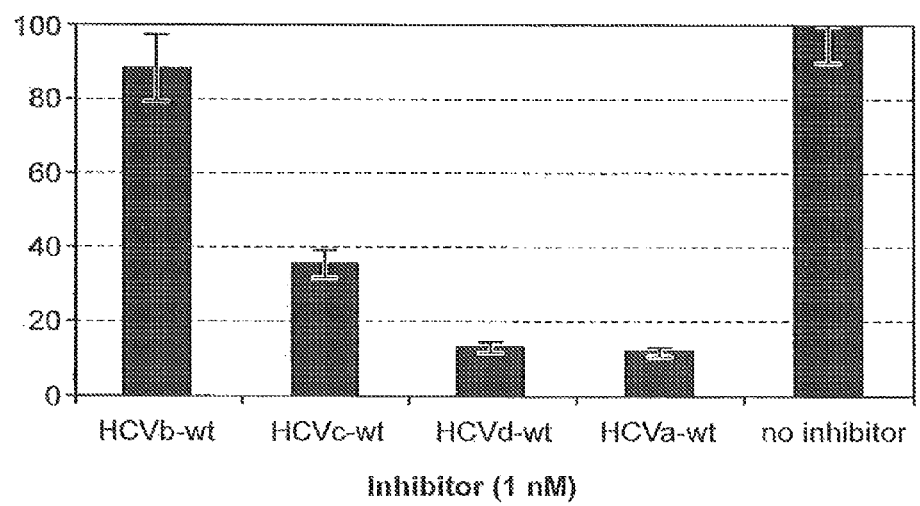
FIG. 1F is a bar graph depicting the results of a screen of shRNAs for the ability to inhibit HCV IRES-mediated gene expression in 293FT cells. 293FT cells were cotransfected with pCDNA3/HCV IRES dual luciferase reporter construct, pSEAP2 (as a transfection and specificity control), and an shRNA (at 1 nM) in a well of a 24-well tissue culture plate. Plasmid pUC18 was added to provide a total of 800 ng nucleic acid per well. 48 hours post-transfection, cells were lysed and firefly luciferase activity was measured by a luminometer. All data are the results of individual, independent experiments performed in triplicate, and normalized to SEAP.

As seen in FIG. 1F, both HCVa-wt and HCVd-wt shRNAs, which target the region of the IRES immediately downstream of the AUG translation start site (positions 344-368 and 350-374, respectively), strongly inhibit HCV IRES-mediated fLuc expression in human 293FT cells. HCVc-wt (targeting 318-342) showed moderate inhibition and HCVb-wt (299-323) displayed little if any activity, as expected. Thus, preliminary screening revealed a potent shRNA, HCVa-wt, that was chosen for further detailed studies.

Figure 2A:
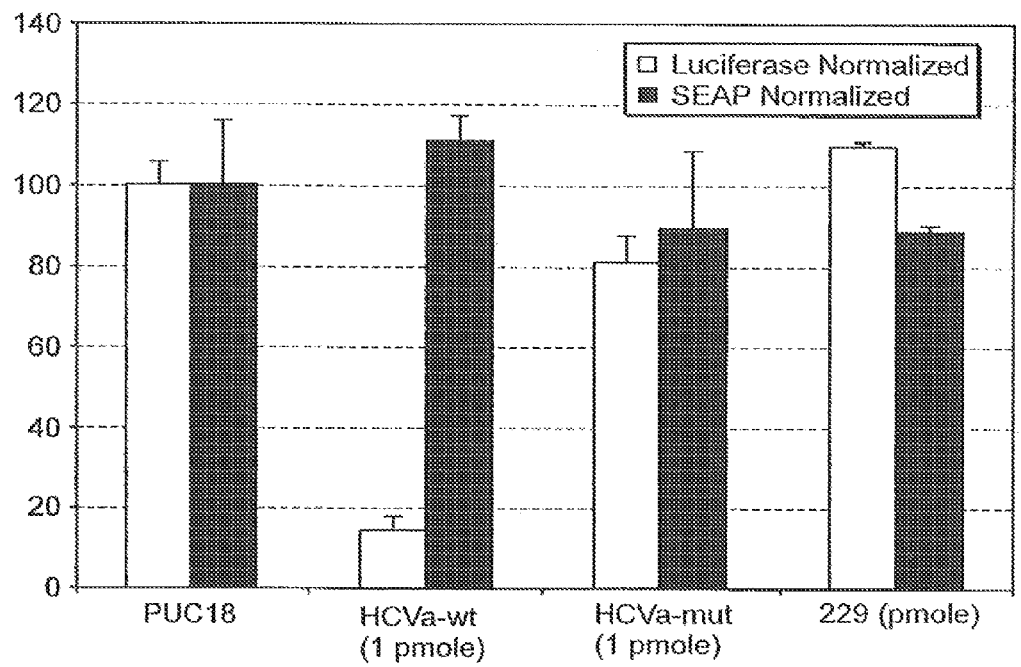
FIG. 2A is a bar graph depicting the results of experiments testing inhibition of HCV-IRES driven gene expression in 293FT cells that were cotransfected with dual luciferase reporter and SEAP expressing plasmids and 1 pmole of in vitro transcribed shRNAs. The target plasmid was pCDNA3/HCV IRES dual luciferase reporter (HCV IRES, as shown in FIG. 1E). Firefly luciferase activity measured as described in Example 1. Firefly luciferase and SEAP activities were normalized to 100.

Specificity and Potency of Inhibition of HCV IRES-Mediated Gene Expression by shRNAs in 293FT Cells To further test inhibition of HCV-IRES driven gene expression, 293FT cells were cotransfected with dual luciferase reporter and SEAP expressing plasmids as well as 1 pmole of in vitro transcribed shRNAs. The target plasmid was pCDNA3/HCV IRES dual luciferase reporter (HCV IRES, as shown in FIG. 1E). pUC18 plasmid was added to the transfection mix to give a final total nucleic acid concentration of 800 ng per transfection per well (24-well tissue culture plates). Forty-eight hours later, supernatant was removed for SEAP analysis, then cells were lysed and firefly and renilla (not shown) luciferase activity measured as described in Example 1. Firefly luciferase and SEAP activities were normalized to 100. Results are shown in FIG. 2A.

HCVa-wt shRNA targeting the region of the IRES immediately downstream of the AUG translation start site strongly inhibited HCV IRES-mediated fLuc expression in both human 293FT (FIG. 2) and hepatocyte Huh7 (FIG. 3B) cell lines. Little or no inhibition was observed using either a mutant shRNA (HCVa-mut) containing two changes in the pairing of the RNA hairpin (for mismatch location, see FIG. 1B) or an unrelated TNF (229) shRNA. The 229 TNF shRNA is highly effective at inhibiting TNF expression (Seyhan et al., RNA, 2005, 11:837-846), suggesting that this shRNA is utilized effectively by the RNAi apparatus. Single nucleotide changes in the hairpin region, at either the upstream or downstream position (SNP1 and SNP2 respectively; see FIG. 2C), had a partial effect.

Figure 2B:
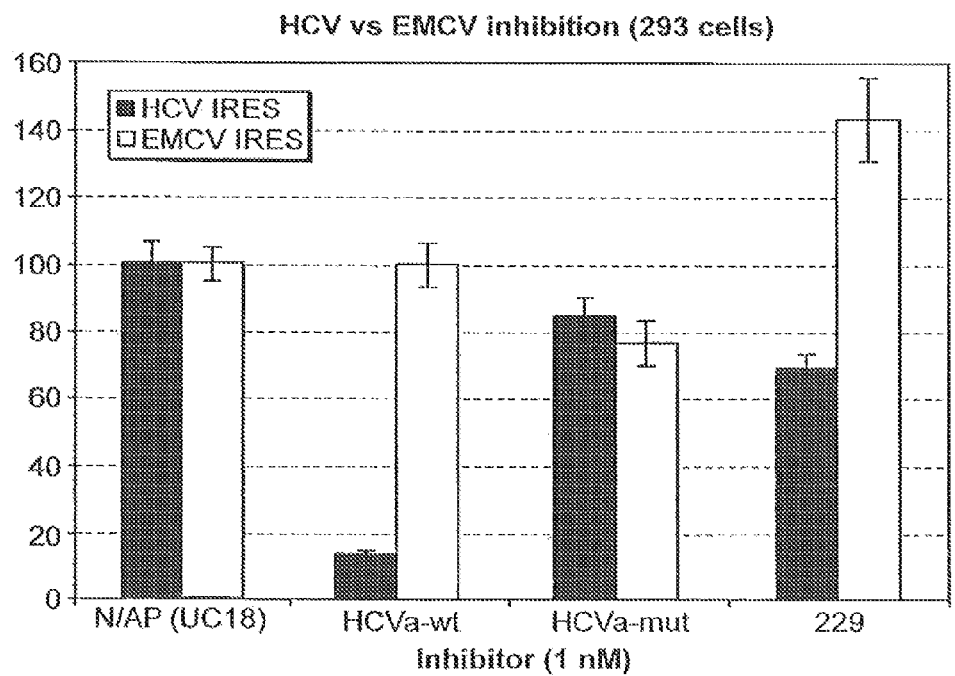
FIG. 2B is a bar graph depicting the results of experiments testing HCV versus EMCB inhibition in 293FT cells. The data are presented as luciferase activity divided by SEAP activity normalized to 100.
Figure 2C:
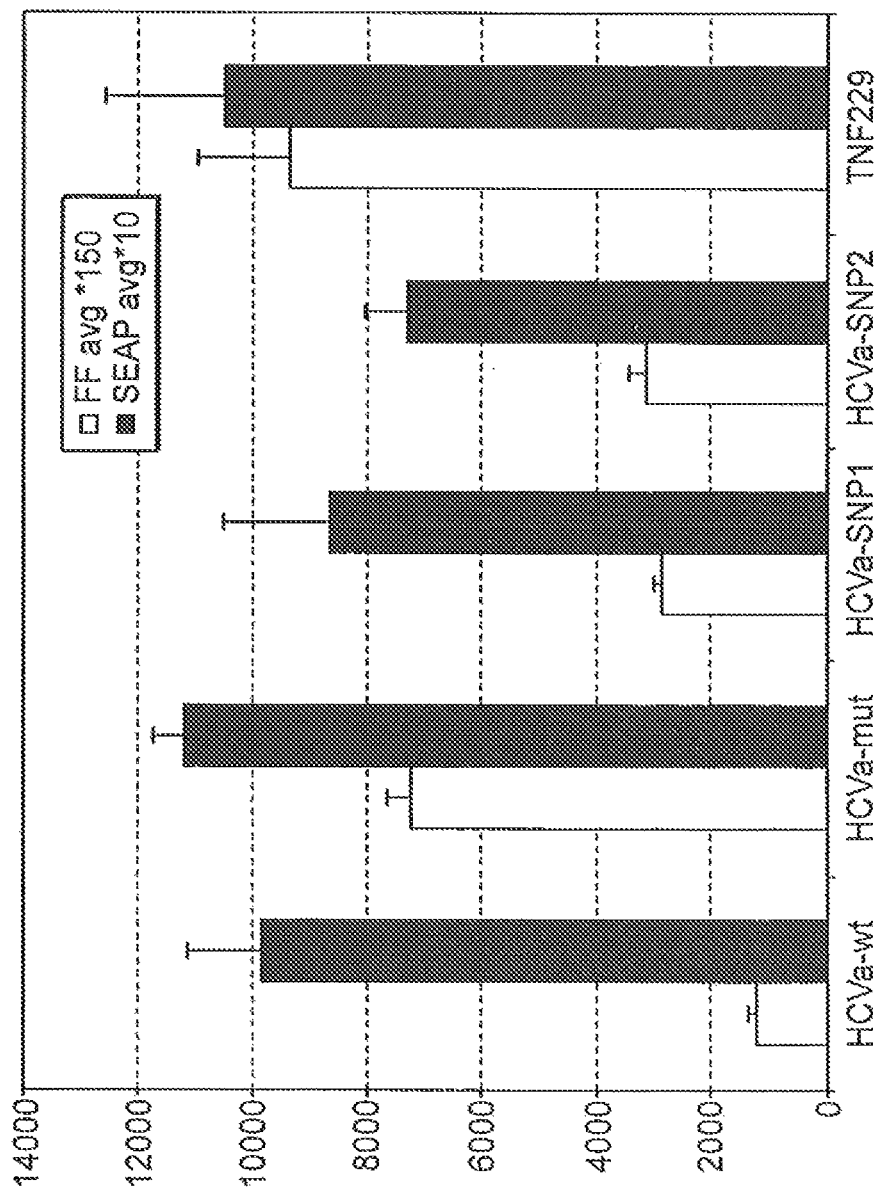
FIG. 2C is a bar graph depicting the results of experiments demonstrating the effect of single-base mismatches on potency of shRNAs. Experimental conditions were as described for FIG. 2A. SNP1 and SNP2 contained mutated base pairs as shown in FIG. 1B.
Figure 2E:
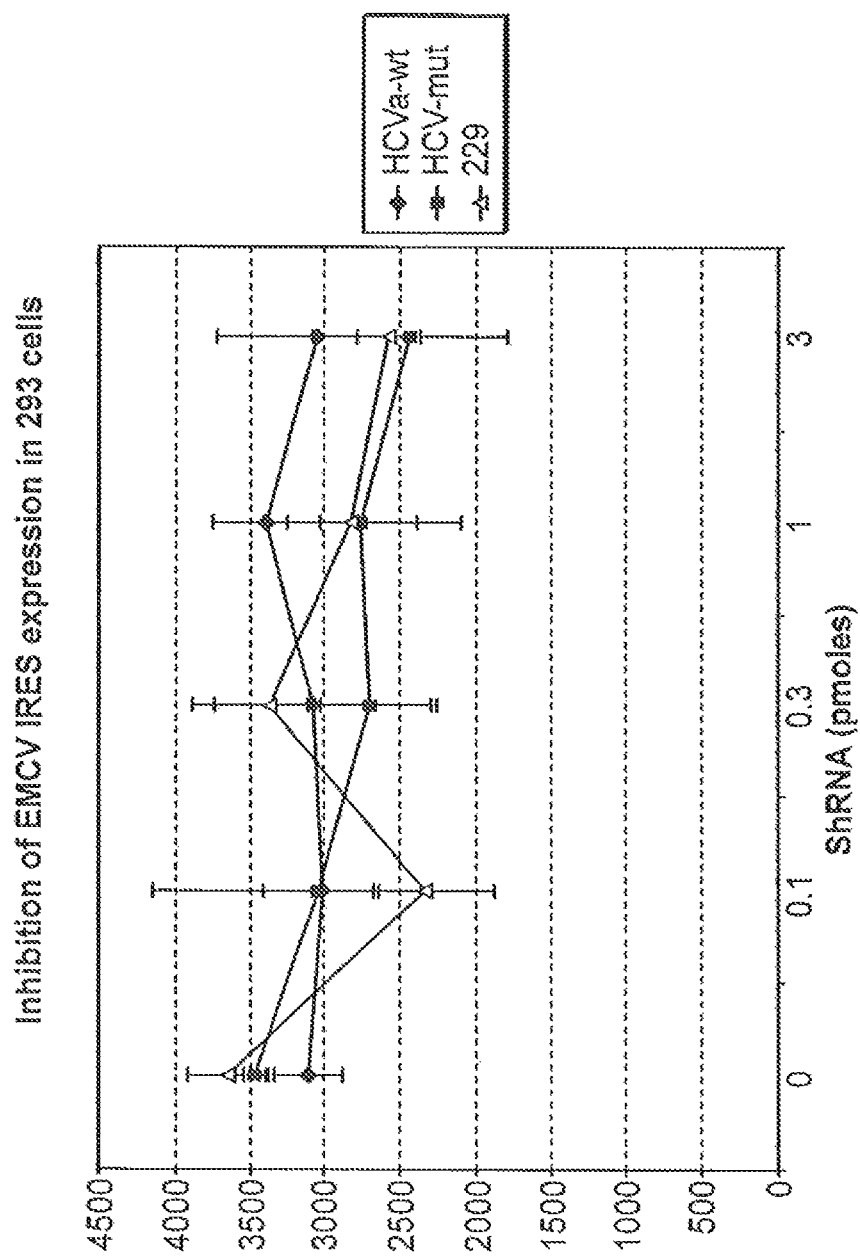
FIG. 2E is a line graph depicting the resulting of experiments testing dose response of HCVa-wt, HCVa-mut), and 229 shRNAs on gene expression from a dual-luciferase reporter lacking shRNA target sites. The procedure was as described for FIG. 2D except target was firefly luciferase driven by EMCV IRES instead of HCV IRES.
Figure 3A:
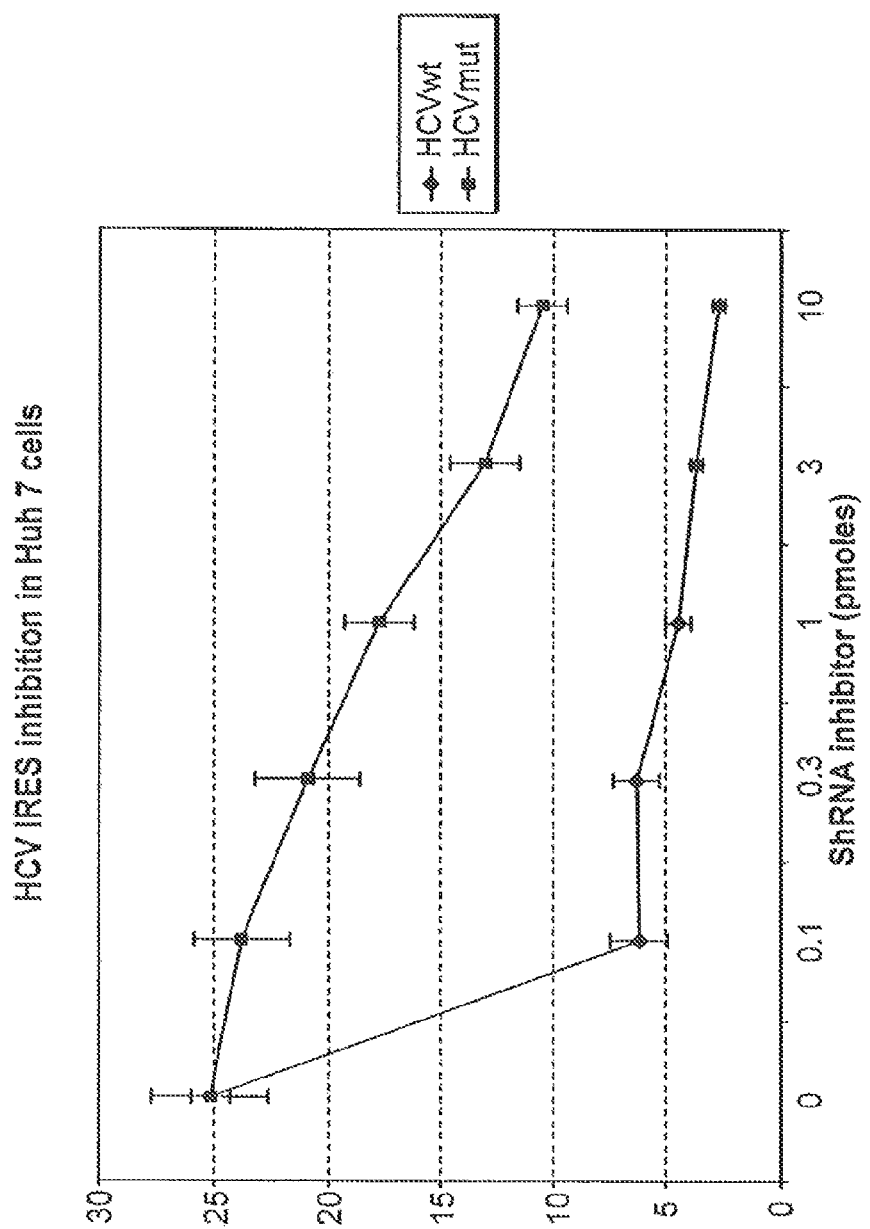
FIG. 3A is a line graph depicting the results of experiments testing dose response to HCVa-wt and HCVa-mut shRNAs using the human hepatocyte cell line, Huh7. Procedures were as described for FIG. 2D, except that Huh7 cells were used.
Figure 3B:
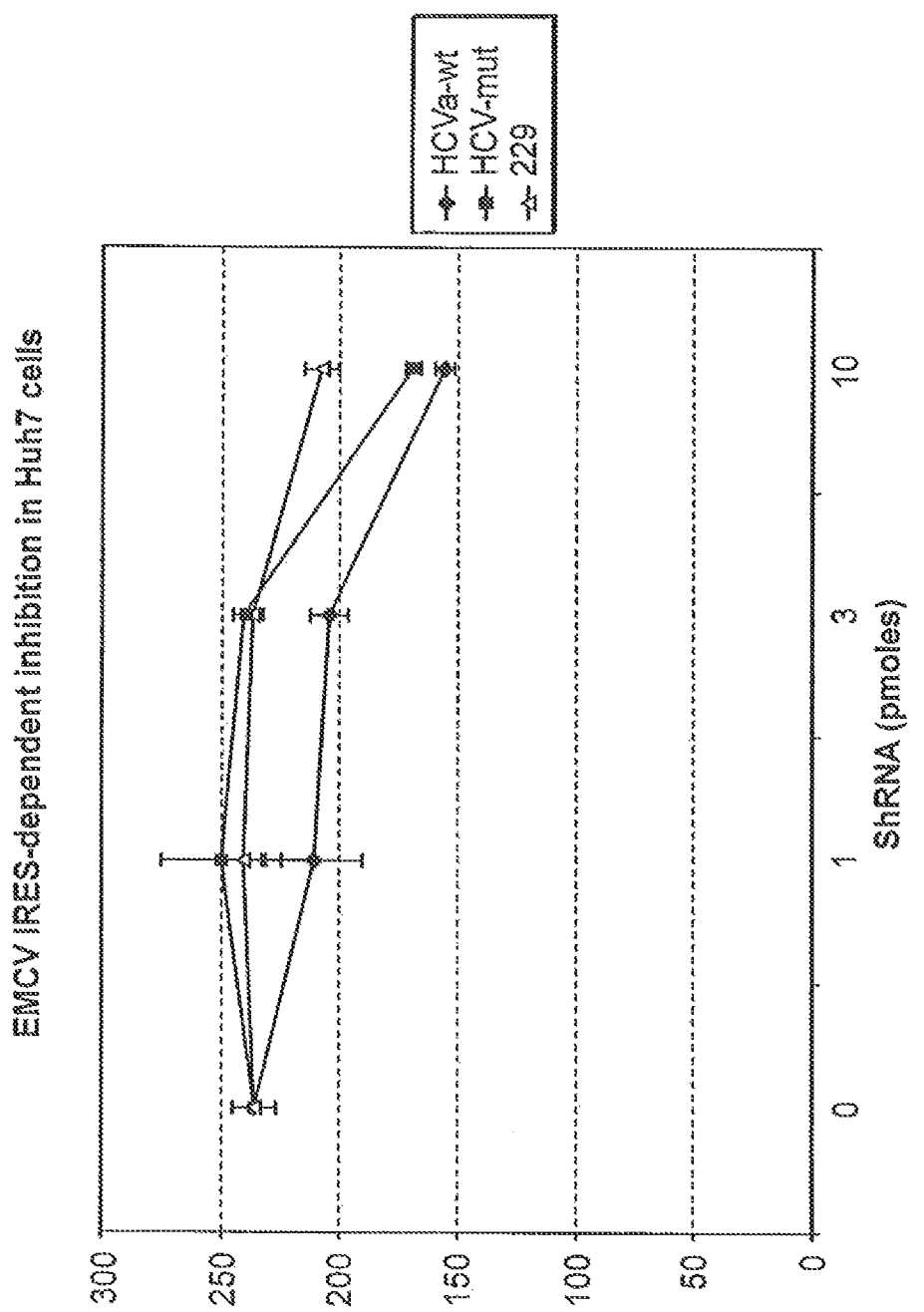
FIG. 3B is a line graph depicting the results of experiments demonstrating that HCVa-wt shRNA does not inhibit a similar target lacking the HCV IRES. Cells were transfected as in FIG. 3A except that pCDNA3/EMCV IRES dual luciferase reporter (EMCV IRES) was added in place of pCDNA3/HCV IRES dual luciferase reporter (HCV IRES). All data are presented as luciferase activity divided by SEAP. All data were generated from individual, independent experiments performed in triplicate.

Little or no inhibition was observed when the HCV shRNA was targeted to a similar dual luciferase construct in which the HCV IRES was replaced by the encephalomyocarditis virus (EMCV) IRES (FIGS. 2B and 3B). Thus, the data of FIG. 2B illustrate that HCVa-wt shRNA does not inhibit a similar target lacking the HCV IRES. In this experiment, cells were transfected as for FIG. 2A except that pCDNA3/EMCV dual luciferase reporter (EMCV IRES) was used as target in place of pCDNA3/HCV. These data are presented in FIG. 2B as luciferase activity divided by SEAP activity normalized to 100.

Figure 2F:
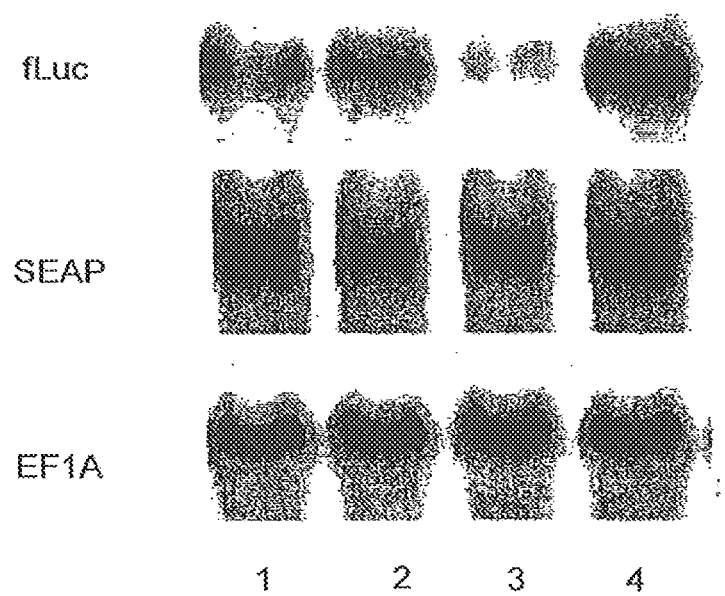
FIG. 2F is a reproduction of a Northern blot analysis of co-transfected 293FT cells treated as follows; 10 µg of total RNA isolated from cells transfected with no inhibitor (lane 1), 229 (lane 2) HCVa-wt (lane 3), or HCVa-mut (lane 4) were separated by denaturing gel electrophoresis, transferred to membrane and hybridized sequentially to $^{32}$P-labeled fLuc, SEAP, or elongation factor 1A (EF1A) cDNA probes. The RNA blot was exposed to a storage phosphor screen for visualization and quantitation (BioRad FX Molecular Imager).

To confirm that the shRNAs were acting by degrading their target mRNA, a Northern blot analysis was performed (FIG. 2F). Equal amounts of total RNA, isolated from cells transfected with no inhibitor or HCVa-wt, HCVmut1/2, or 229 shRNAs, were separated by gel electrophoresis. The separated RNA was transferred to a membrane and hybridized to radiolabeled cDNA probes specific for fLuc, SEAP and elongation factor 1A (EF1A). HCVa-wt shRNA (lane 3) specifically inhibited fLuc mRNA accumulation (63% inhibition compared to 229 shRNA (lane 2) when corrected for SEAP and EF1A mRNA levels; no inhibition was observed for HCVa-mut1/2) (compare lanes 3 and 4) following quantitation by phosphorimager. These data demonstrate that the shRNAs were degrading target mRNA.

Dose response experiments showed that the HCVa-wt shRNA effectively inhibited HCV IRES-dependent gene expression at 0.3 nM in 293FT cells (96 percent inhibition, see FIG. 2D) and 0.1 nM in Huh7 cells (75 percent inhibition, see FIG. 3A).

Figure 4A:
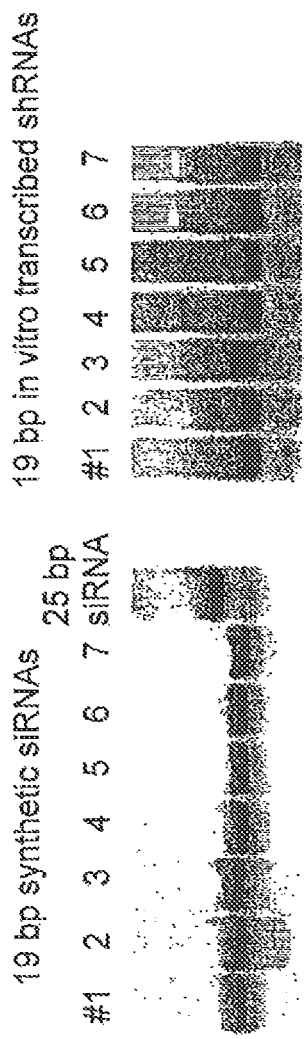
FIG. 4A depicts sequences of seven 19 base pair viral recognition sequences of synthetic siRNAs and shRNAs contained within the 25 nucleotide target site of HCV genotype 1A (SEQ ID NO:26) and analysis of their purity on 10% native polyacrylamide gel stained with ethidium bromide. siRNAs: sense and antisense strands contained 3'-UU overhangs; shRNAs: loop sequences and 3', 5'-end overhangs were identical to those of the 25 base pair shRNAs.
Figure 4B:
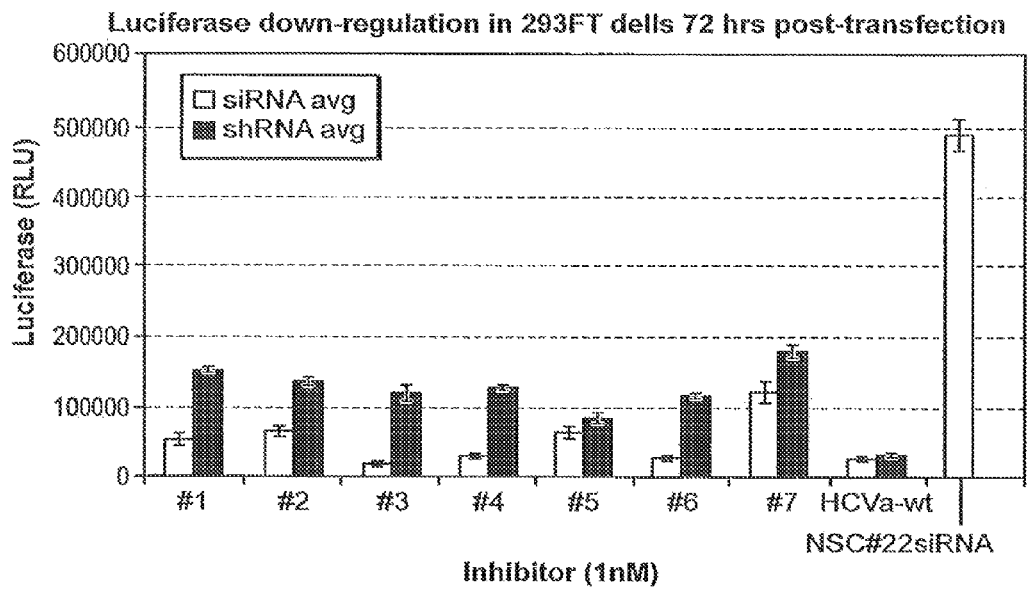
FIG. 4B is a bar graph depicting the results of experiments in which RNA inhibitors (siRNAs and shRNAs) were assayed for inhibition of HCV IRES-mediated gene expression at an inhibitor concentration 1 nM in 293 FT cells.
Figure 4C:
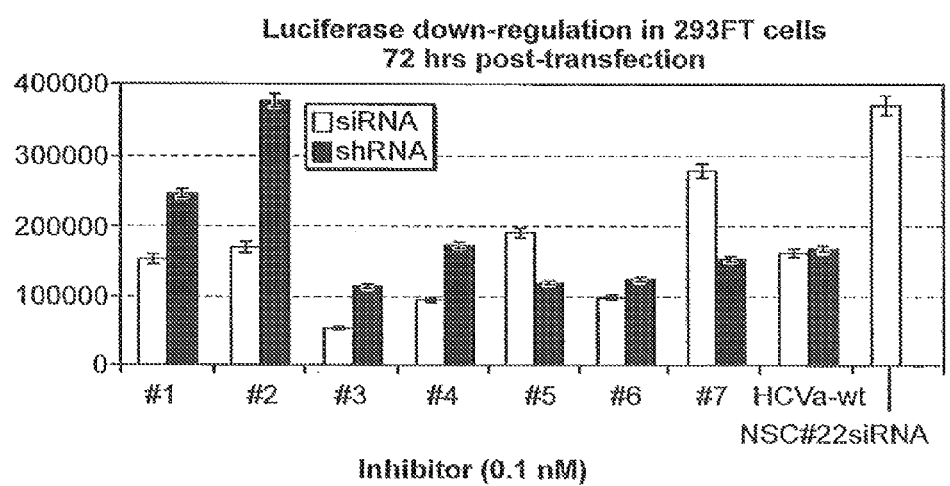
FIG. 4C is a bar graph depicting the results of experiments in which RNA inhibitors were assayed for inhibition of HCV IRES-mediated gene expression at an inhibitor concentration of 0.1 nM in 293 FT cells.

To further investigate local sequence effects on potency, seven in vitro-transcribed 19 bp shRNA and the corresponding synthetic 19 base pair siRNA, targeting all possible positions within the 31-base pair site of HCVa (344-374; FIG. 4A), were assayed for inhibitory activity. A 25 base pair synthetic siRNA corresponding to HCVa-wt shRNA was also tested. All of them exhibited a high level of activity (FIG. 4B). The most potent were siRNA and shRNA versions of HCVa as well as siRNA #3, which was effective at 1 nM (>90% inhibition, FIG. 4B) and 0.1 nM (about 90% inhibition, FIG. 4C). Thus, 19-25 base pair shRNAs and siRNAs designed to target the region 344-374 on the HCV IRES are potent, with some local differences.

Example 3 shRNA Inhibition of HCV IRES-Mediated Gene Expression in a Mouse Model System

Figure 5A:
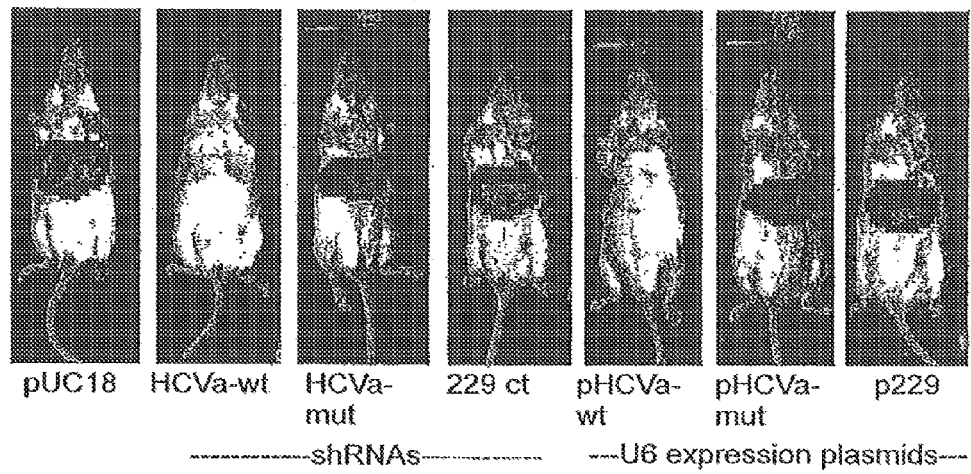
FIG. 5A is a reproduction of IVIS images of mice in which dual luciferase HCV IRES reporter plasmid (10 µg) and SEAP (added to control for injection efficiency and nonspecific inhibition) were co-injected into the tail veins of mice as described in Example 1 with 100 µg of the indicated HCV shRNA or control 229 shRNA) directly or in the form of 100 µg of pol III expression plasmids expressing shRNA (or pUC18 plasmid as control). At various time-points (24, 36, 48, 60, 72, 84 and 100 hours) post-injection, luciferin was administered intraperitoneally, and the mice were imaged using the IVIS in vivo imaging system. Images are of representative mice from the 84 hour time point.
Figure 5B:
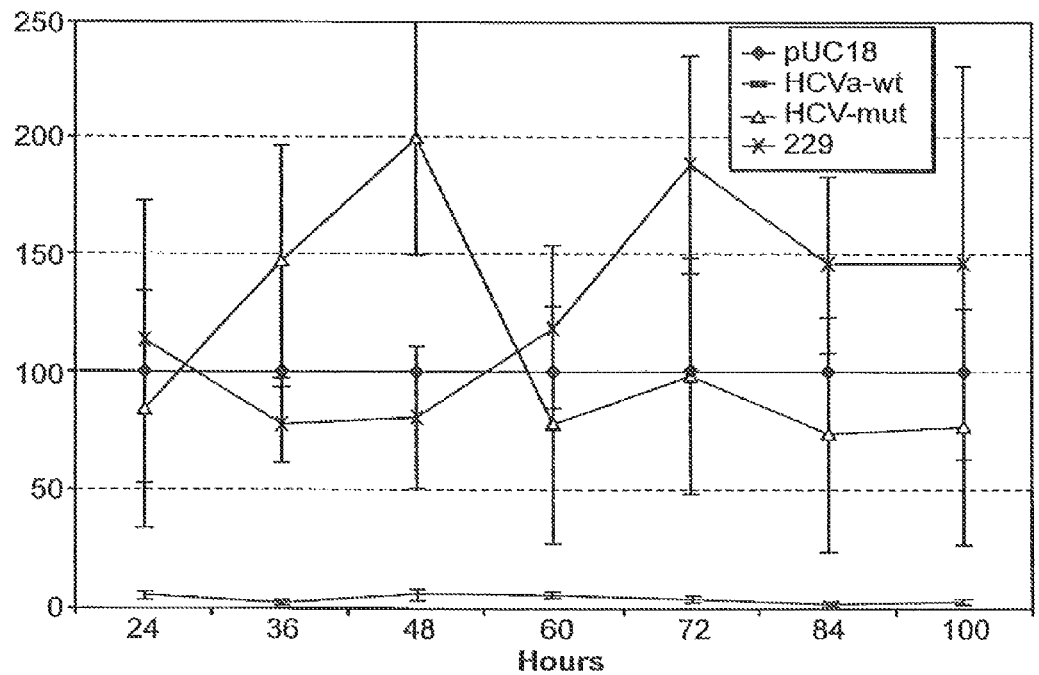
FIG. 5B is a graph depicting the quantitated results of experiments described for FIG. 5A in which there was direct delivery of RNA. Quantitation was performed using ImageQuant™ software. Each time-point represents the average of 4-5 mice. At the 96 hour time point, the mice were bled and the amount of SEAP activity determined by pNPP assay as described in Example 1. The quantitated data are presented as luciferase divided by SEAP activity, normalized to pUC18 control mice (100%, no error bars shown on pUC18 control for clarity; error bars are similar to the others shown).

The ability of the HCV shRNA and HCV shRNA expression plasmid to inhibit target gene expression was extended to a mouse model system using hydrodynamic injection to deliver the nucleic acids to mouse liver. FIG. 5 shows the results of injecting a large volume of PBS (1.8 ml) containing pHCV dual Luc, pSEAP2, and shRNAs (10 fold excess over the target on a mass basis of either shRNA or pol III expression vectors expressing the shRNAs) into the tail veins of mice (n=4-5 mice). At the time points shown in FIG. 5B, luciferin was injected intraperitoneally and the mice were imaged with a high sensitivity, cooled CCD camera. (FIG. 5A shows representative mice chosen from each set (4-5 mice per set) at the 84 hour time point.) At all time points tested, HCV shRNA robustly inhibited luciferase expression ranging from 98% (84 hour time point) to 94% (48-hour time point) inhibition compared to mice injected with pUC18 in place of shRNA inhibitor. Mutant (mut) or control (229) shRNAs had little or no effect. It should be noted that luciferase activity decreases with time, possibly due to loss of DNA or promoter silencing [8] and that the data are normalized within each time point (see description of FIG. 5 above).

Figure 6:
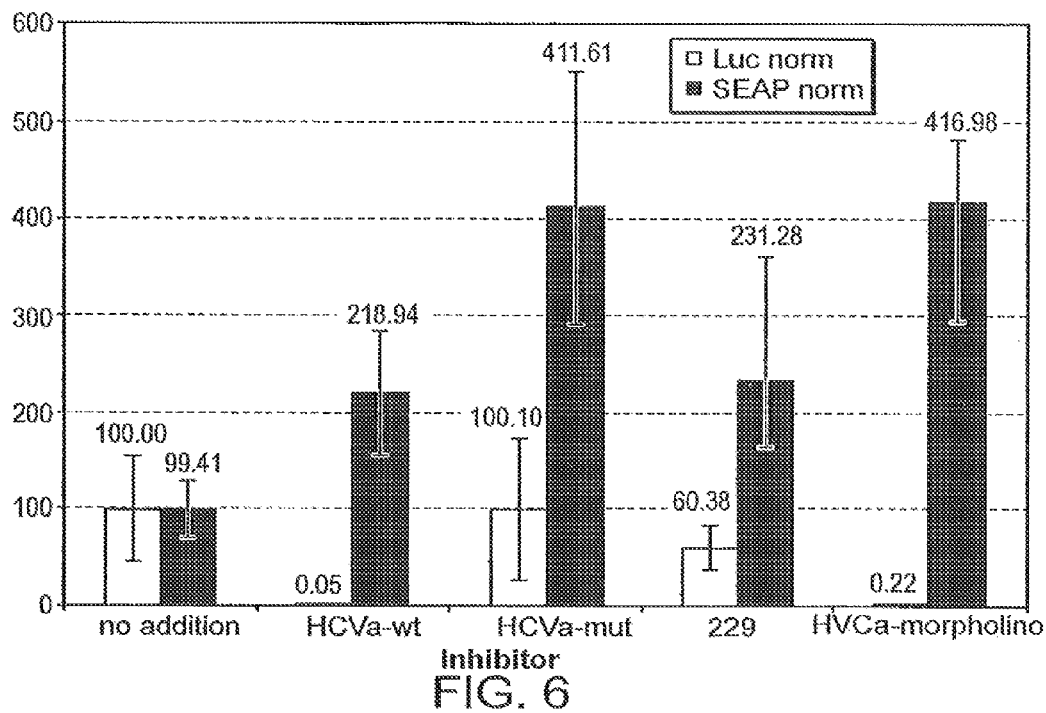
FIG. 6 is a bar graph depicting the results of experiments in which shRNA and phosphorodiamidate morpholino oligomer inhibition of HCV IRES-mediated reporter gene expression in mice was compared. Mice were co-injected as described in experiments for FIG. 5 with dual luciferase HCV IRES reporter plasmid and pSEAP with 100 µg of the indicated HCV shRNA inhibitors or 1 nmole of a morpholino oligonucleotide previously shown to inhibit HCV IRES expression construct [8]. The mice were imaged at various times (12 hours, 24 hours, 48 hours, and 144 hours) post-treatment. Data shown are for the 48 hour time point. The quantitated data are presented as luciferase and SEAP activities, normalized to pUC18 control (no addition) mice. The results presented are from 3-5 mice per construct.

FIG. 6 shows a comparison of HCVa-wt shRNA inhibitory activity with a phosphoramidite morpholino oligomer that was previously shown to effectively target this same site [8]. Both the HCVa-wt shRNA and morpholino oligomers effectively blocked luciferase expression at all time-points tested. Data are shown for the 48-hour time-point, where inhibition was 99.95 and 99.88 percent, respectively for the HCVa-wt shRNA and morpholino inhibitors.

Example 4

Inhibition of Semliki Forest Virus (SFV) Using shRNAs

Figure 7:
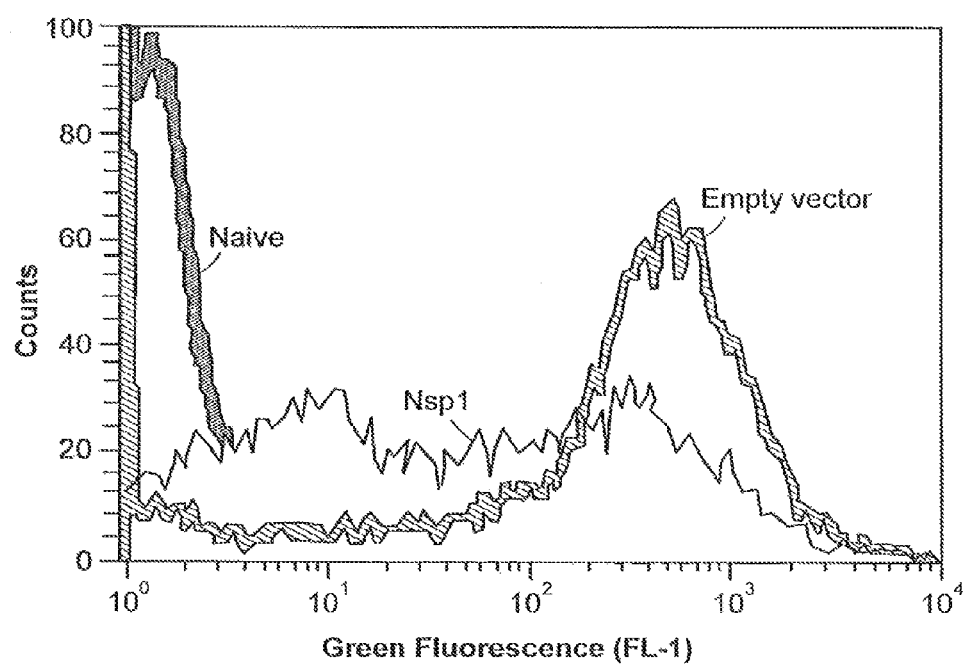
FIG. 7 is a graph depicting the results of experiments in which BHK-21 cells were transiently transfected with plasmids expressing an inhibitory shRNA targeting the nsp-1 gene. Twenty-four hours after transfection, cells were infected with 10 µl of replication-proficient GFP-expressing Semliki Forest virus (SFV-GFP-VA7; multiplicity of infection (MOI) sufficient for about 100% infection) and assayed for virus-mediated GFP expression by flow cytometry 24 hours after infection. The level of siRNA-mediated suppression was about 35%. Labels: Nsp 1. shRNA targeting Nsp-1 gene (nsp-1#2); empty vector, pU6; naive, uninfected BHK cells.

SFV has been used as a model system for more virulent positive-strand RNA viruses. To examine the inhibitory effect of RNAi on SFV growth, shRNAs targeting four SFV genes (nsp-1, nsp-2 and nsp-4, and capsid) and one mismatched control for the nsp-4 site were generated and expressed from a U6 promoter. Their ability to tested their ability to inhibit the proliferation of SFV-A7-EGFP, a version of the replication-proficient SFV strain SFV-A7 that expresses a eGFP reporter gene [49]. A modest reduction (about 35%) of SFV-GFP replication was seen with shRNAs targeting the nsp-1 (FIG. 7) but not nsp-2, nsp-4 or capsid coding regions, nor with the mismatched siRNA (not shown).

Figure 8:
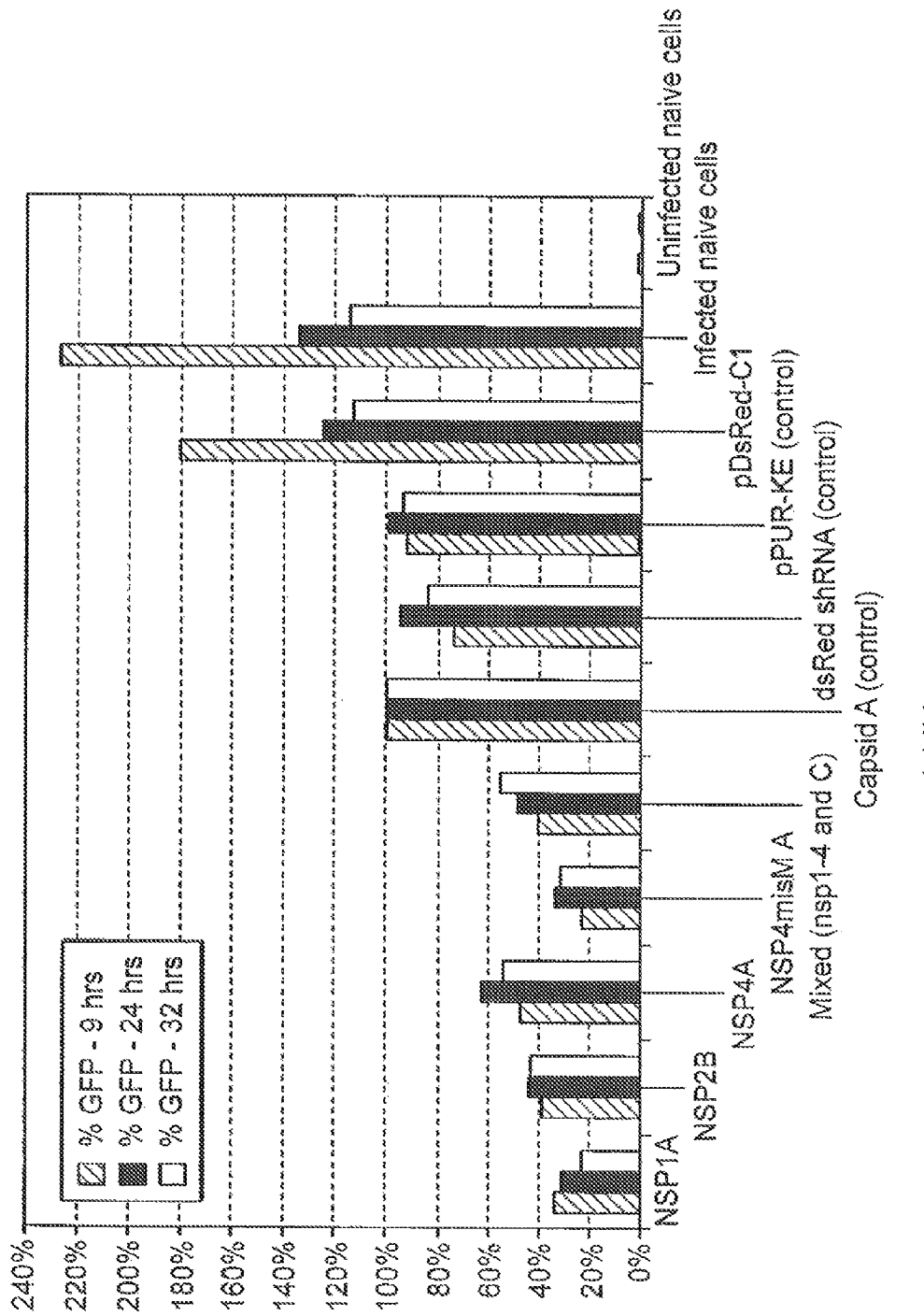
FIG. 8 is a bar graph depicting the results of experiments in which inhibition of replication-deficient SFV (SFV-PD713P-GFP) by shRNAs was investigated. BHK-21 cells were transiently transfected with plasmids expressing inhibitor shRNAs. Forty-six hours after transfection, cells were infected with SFV-GFP virus at an MOI of 5 with 8% PEG in serum-free media for one hour. Then complete media was added and cells were incubated at 37° C. overnight. Cells were analyzed by flow cytometry at 9, 24, 32, 99, and 125 hours after infection. For clarity, only three time points are shown (9, 24 and 32 hours). The amount of inhibition of each shRNA was normalized to capsid shRNA. Capsid mRNA is not present in this SFV-GFP replication-deficient virus and therefore capsid shRNA should have no effect on GFP expression. The transfection efficiency for the shRNA expression constructs for this experiment was about 70%, suggesting that actual viral inhibition is significantly higher than the levels indicated. The fifth set of bars (Mixed) refers to a mixture of shRNAs targeting nsp 1-4 and capsid.
Figure 9:
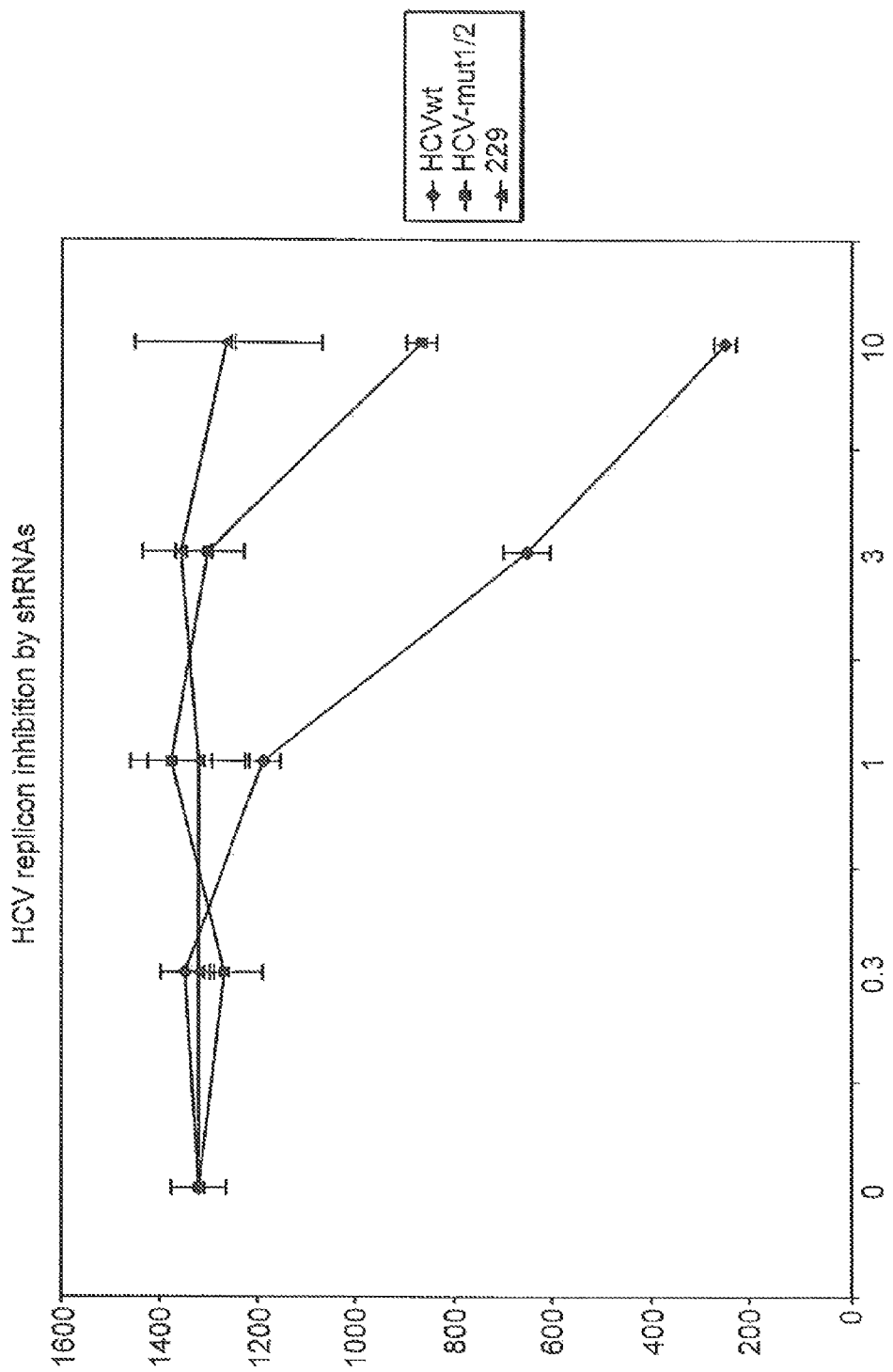
FIG. 9 is a line graph depicting the results of experiments testing HCV replicon inhibition by shRNAs.

A site within the capsid coding region that was previously shown to be effective on Sindbis virus [50] was not effective on SFV. The Sindbis-SFV sequence homology at this site is only 77%. SFV is a very rapidly growing virus, producing up to 200,000 cytoplasmic RNAs during its infectious cycle. To see if cells could better protected from a slower-growing virus, the effects of these siRNAs on a replication-deficient strain of SFV-GFP were tested in two separate experiments. FIG. 8 shows that U6-expressed shRNAs targeting this SFV strain can reduce viral expression by $\geq$70% over a time period of up to five days. This effect was seen with siRNAs targeting the nonstructural genes nsp-1, nsp-2, and nsp-4 as well as an siRNA with one mismatch to nsp-4, but not for the capsid gene (which is lacking in this crippled virus) or other controls (FIG. 8). Note that the length of the sequence targeted by the shRNAs is 29 nucleotides and the single mismatch used in the nsp-4 mismatch shRNA is apparently not disruptive for the RNAi effect. The wide variation in effectiveness of the various shRNAs underscores the importance of a library approach for finding the best siRNAs and shRNAs when dealing with rapidly replicating and highly mutagenic viruses such as SFV.

Dose-response experiments were performed to examine inhibition of an HCV replicon system in Huh7 cells by HCVa-wt shRNA and HCVa-mut shRNA as well as a non-specific control shRNA (229). The antiviral activity of test compounds was assayed in the stably HCV RNA-replicating cell line, AVA5, derived by transfection of the human hepatoblastoma cell line, Huh7 (Blight, et al., Science, 2000, 290:1972). RNA-based inhibitors were co-transfected with DsRed expression plasmid into cultures that were about 80 percent confluent. HCV RNA levels were assessed 48 hours after transfection using dot blot hybridization. Assays were conducted in triplicate cultures. A total of 4-6 untreated control cultures, and triplicate cultures treated with 10, 3, and 1 IU/ml α-interferon (active antiviral with no cytotoxicity), and 100, 10, and 1 uM ribavirin (no antiviral activity and cytotoxic) served as positive antiviral and toxicity controls. The transfection efficiency was estimated by fluorescence microscopy (DsRed expression). Both HCV and b-actin RNA levels in triplicate treated cultures were determined as a percentage of the mean levels of RNA detected in untreated cultures (6 total). Beta-actin RNA levels are used both as a measure of toxicity, and to normalize the amount of cellular RNA in each sample. A level of 30% or less HCV RNA (relative to control cultures) is considered to be a positive antiviral effect, and a level of 50% or less b-actin RNA (relative to control cultures) is considered to be a cytotoxic effect. Cytotoxicity is measured using an established neutral red dye uptake assay (Korba, B. E. and J. L. Gerin (1992). Use of a standardized cell culture assay to determine activities of nucleoside analogs against hepatitis B virus replication (*Antivir. Res.* 19:55-70).

]Inhibition of an HCV replicon system in Huh7 cells by HCVa-wt shRNA and HCVa-mut shRNA as well as an irrelevant control shRNA (229); dose response. The antiviral activity of test compounds was assayed in the stably HCV RNA-replicating cell line, AVA5, derived by transfection of the human hepatoblastoma cell line, Huh7 (Blight et al. Science, 2000, 290:1972). RNA-based inhibitors were co-transfected with DsRed expression plasmid into ~80 percent confluent cultures and HCV RNA levels were assessed 48 hours after transfection using dot blot hybridization. Assays were conducted in triplicate cultures. A total of 4-6 untreated control cultures, and triplicate cultures treated with 10, 3, and 1 IU/ml a-interferon (active antiviral with no cytotoxicity), and 100, 10, and 1 uM ribavirin (no antiviral activity and cytotoxic) served as positive antiviral and toxicity controls. The transfection efficiency was estimated by fluorescence microscopy (DsRed expression). Both HCV and beta-actin RNA levels in triplicate treated cultures were determined as a percentage of the mean levels of RNA detected in untreated cultures (6 total). Beta actin RNA levels were used both as a measure of toxicity, and to normalize the amount of cellular RNA in each sample. A level of 30% or less HCV RNA (relative to control cultures) was considered to be a positive antiviral effect, and a level of 50% or less beta-actin RNA (relative to control cultures) was considered to be a cytotoxic effect. Cytotoxicity was measured using an established neutral red dye uptake assay (Korba et al., Antiviral Res., 1992, 19:55-70). Use of a standardized cell culture assay to determine activities of nucleoside analogs against hepatitis B virus replication (Korba et al., 1992 supra).

Example 5

Identification of shRNAs that Inhibit HCV IRES-Dependent Gene Expression in Tissue Culture Cells The ability of in vitro-transcribed small hairpin RNAs (shRNAs) to inhibit hepatitis C virus internal ribosome entry site (HCV IRES)-dependent gene expression in cultured cells was investigated. As disclosed supra, a 25 base pair shRNA HCVa-wt that targets the 3' end of the HCV IRES, near the AUG translation start site (Table 2) was found to be effective for disrupting expression of HCV. To assess the ability of co-transfected shRNA constructs to interfere with the function of the IRES, a reporter construct (pHCV Dual Luciferase plasmid) in which firefly luciferase (fLuc) expression is dependent on the HCV IRES was used (FIG. 1; Wang et al., Mol. Ther., 2005, 12:562-568. In these experiments, 293FT cells were cultured and transfected with a reporter construct and HCVa-wt or one of the other test sequences as described in Wang et al., 2005, supra.

It was found that at a concentration of 1 nM, HCVa-wt caused 90% inhibition of HCV IRES-dependent luciferase expression in 293FT cells (Wang et al., 2005, supra). In subsequent experiments, 26 additional shRNAs targeting various regions of the HCV IRES were designed and tested (FIG. 10, FIG. 16A-B); 3 of the 26 were duplicates of those described above (HCVb, HCVc, HCVd-wt); 23 were new sequences) to identify additional inhibitors of HCV. The goal was to identify shRNAs that can be used either in combination with HCVa-wt), making it harder for the virus to develop resistance by mutating the HCVa-wt target site, or as alternatives to HCVa-wt. The shRNAs to be tested were chosen to avoid regions that vary among different HCV genotypes. Some test sequences were selected using the algorithm available at (e.g., jura.wi.mit.edu/bioc/siRNAext/, and other test sequences intentionally targeted HCV-IRES sequences that, due to their CG content and other characteristics, would not be recommended by most algorithms would rule out, such as GC-rich or highly structured regions. The shRNAs were generated by in vitro transcription from dsDNA templates using T7 RNA polymerase and, to promote transcription efficiency, began with the sequence 5'-pppGGG. This 5' sequence formed an overhang of two to three nucleotides, the exact length depending on whether the target site contains one or more guanosine residues at its 5' end (see FIG. 16A-B). If the last nucleotide of the RNA sense strand matching a target sequence was 'G,' only two more Gs had to be added for efficient transcription, and those Gs are single-stranded on the 5'-end of the shRNA, not complimentary to the target. If the last nucleotide of the shRNA sense strand matching the target, was not a G, then for efficient transcription in the test systems, three Gs had to be added that were not complimentary to the target. All shRNAs tested in this set of experiments had a duplex stem length of 21-25 base pairs and a 10 nucleotide loop derived from microRNA-23, as described for HCVa-wt.

All of the shRNAs (27 total, including HCVa-wt) were assayed for activity as described in Wang, 2005. Briefly, human 293FT cells were co-transfected with pHCV Dual Luciferase® Reporter expression plasmid (Promega, Madison, Wis.), and a secreted alkaline phosphatase expression plasmid (pSEAP2, Clontech, Mountain View, Calif.) to control for efficiency of transfection and possible off-target effects), and shRNA. Results are shown in FIG. 10. SEAP levels were uniform in all samples, indicating efficient transfection and the absence of nonspecific inhibitory or toxic effects, at shRNA concentrations of 1 nM to 5 nM. Most of the shRNAs displayed only moderate activity (less than 60% inhibition at 1 nM). Without committing to any particular theory, this effect is likely because the targeted areas on IRES are highly structured. The exceptions were HCVd-wt, sh37, sh39, hcv17, which target the IRES positions near the HCVa-wt site. These shRNAs caused 85-90% inhibition of HCV IRES dependent gene expression at 1 nM concentration. The low shRNA concentration of 1 nM was chosen to allow easy identification of hyper-functional shRNAs. If the screening were performed at 10 nM shRNA, more shRNAs would display high activity; however, significant nonspecific inhibition was seen at that concentration in some cases. Thus, the screening revealed a 44 nucleotide region (positions 331-374 on the HCV IRES) where five overlapping shRNAs display high activity.

Example 6

Effect of Single Base Mismatches on shRNA Activity

Figure 11:
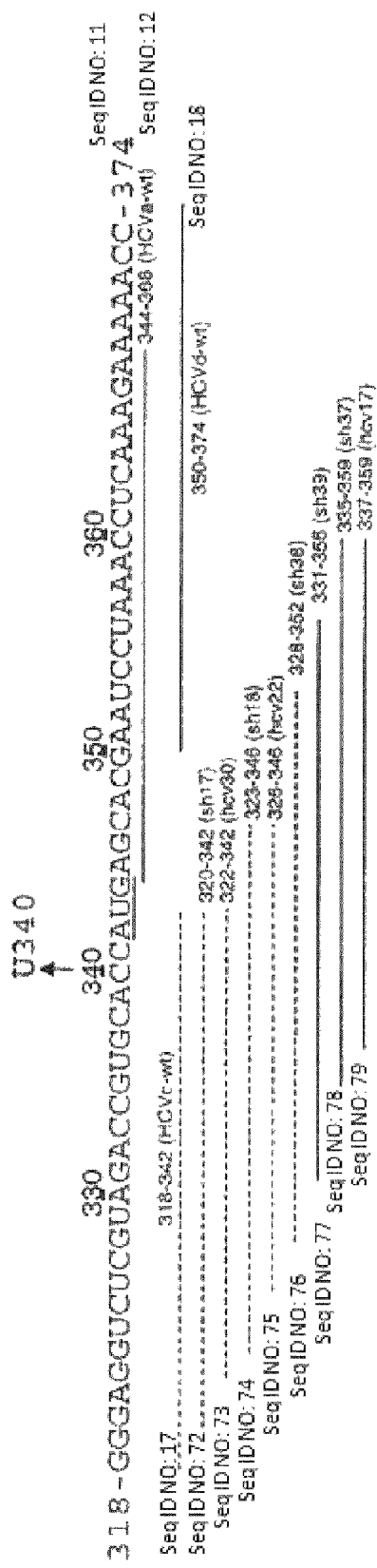
FIG. 11 is a diagrammatic representation of 3'-terminal sequence of the HCV IRES with segments targeted by shRNAs. Mutation C340U (used to assay specificity of shRNAs) is indicated.

It is desirable that a treatment for HCV be effective against mutated HCV. To determine the performance of the RNAs described herein in this regard (e.g., shRNAs targeting HCV IRES), and to address whether off-target effects are problematic, the sensitivity of selected shRNA directed against HCV IRES to point mutations in the target sequence was tested. For these experiments, a C340U mutation was introduced in the HCV IRES using the QuikChange® II Site-Directed Mutagenesis Kit (Stratagene, La Jolla, Calif.). Of the 27 shRNAs that were assayed, nine targeted the mutated region (FIG. 11), therefore their activity could theoretically be affected by this mutation. All of these shRNAs were assayed with the mutated version of pHCV, along with selected shRNAs targeting other sites as controls. For all tested shRNAs, activity was found to be unaffected or slightly decreased compared to the activity of original, perfectly matched target (FIG. 10).

However, in the replicon system, shRNAs were surprisingly found to be SNP-sensitive (see below).

Example 7

Fine Mapping of Target Sites

Figure 12:
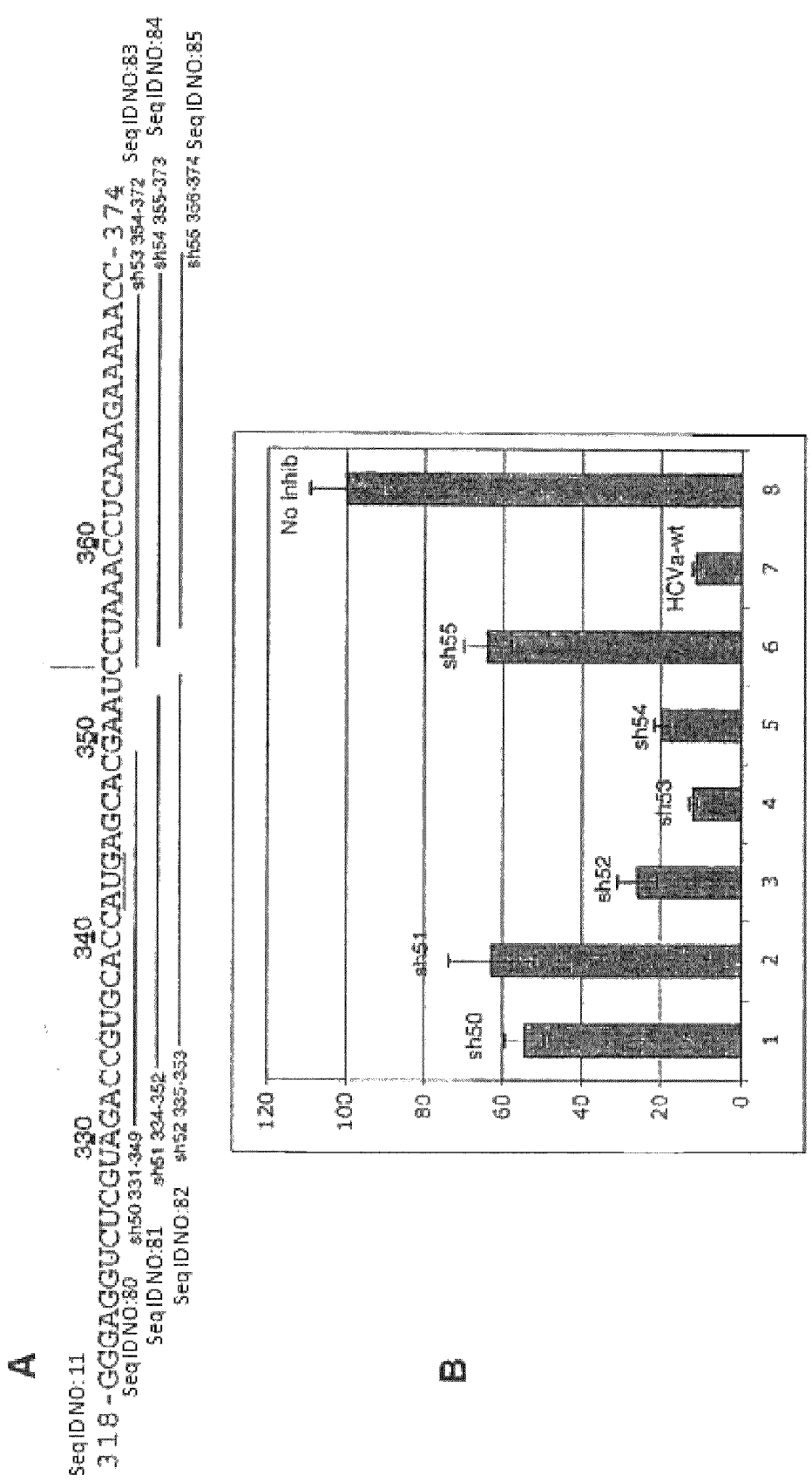
FIG. 12A is a diagrammatic representation of 5'-termini of HCV IRES and targeting positions for six 19-bp shRNAs.
FIG. 12B is a bar graph depicting the results of a screen of shRNAs for the ability to inhibit HCV IRES-mediated gene expression in 293FT cells. Experiments were conducted as for FIG. 10; shRNA concentration, 1 nM.

Six short 19 base pair shRNAs were designed to target a 44 nucleotide site near the 3'-terminus of the HCV IRES: three targeting nucleotides 331-353 and three targeting nucleotides 354-374. These molecules contained 10 nucleotide loops and 5'-GG and 3'-UU overhangs. Screening was performed to identify of non-overlapping candidates that were most effective among those sequences tested for inhibition of HCV expression. All six of the shRNAs tested were able to inhibit activity in the assay system. Three of the six shRNAs (sh52, sh53, and sh54) were identified as the most effective (FIG. 12). This does not preclude the use of those shRNAs that were less effective in a composition, e.g., for treating HCV, for example as part of a composition that includes more than one shRNA and/or siRNA.

Example 8 shRNA Design: Effects of Stem Length, Loop Length and Sequence, and 3'-Terminus

Figure 13:
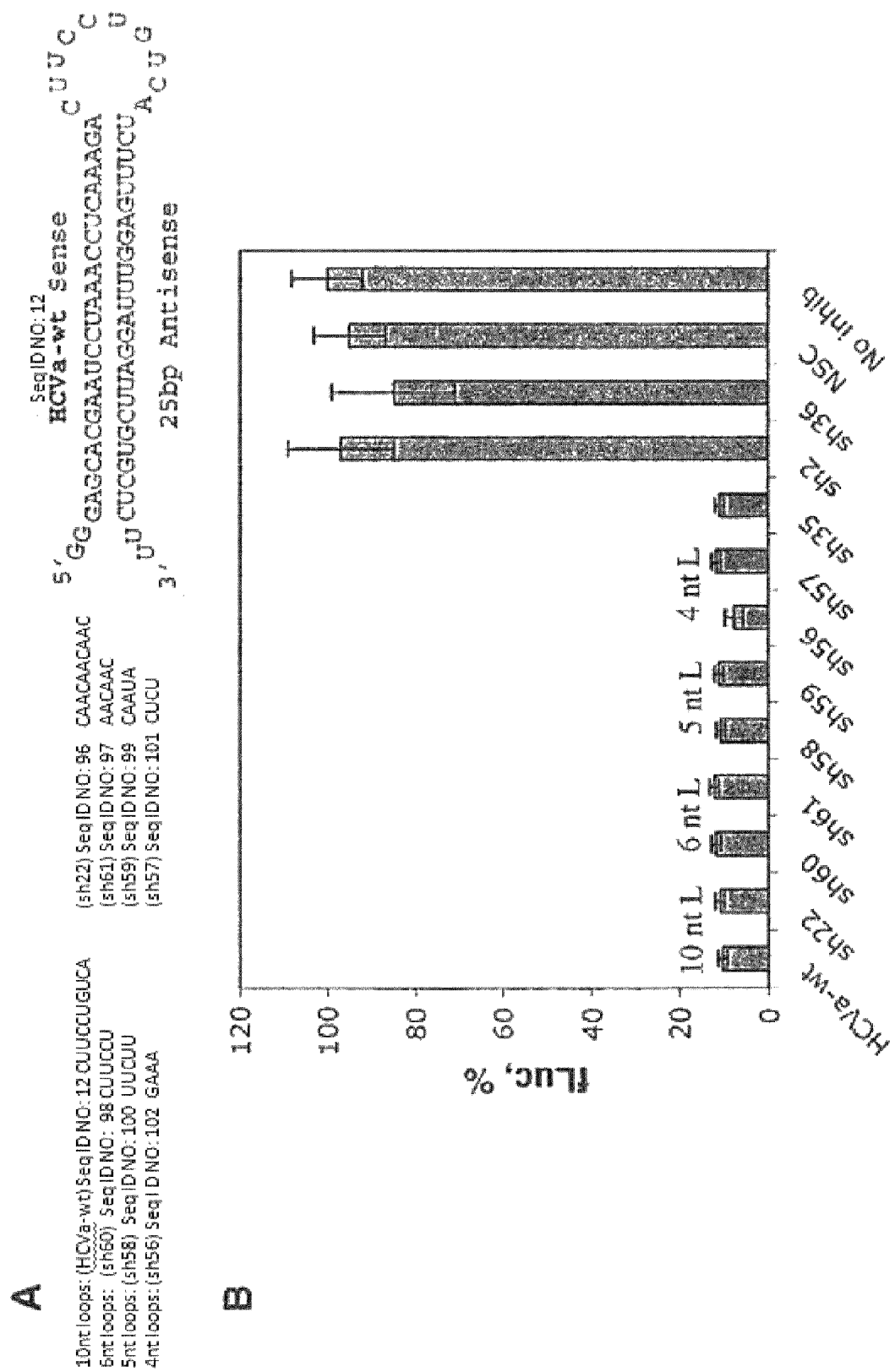
FIG. 13A is a diagrammatic representation of the sequences of tested variants of the depicted 25 base pair shRNA, with the various loop sizes and sequences, as well as 3'-termini that were tested.
FIG. 13B is a bar graph depicting the results of a screen of shRNAs depicted in FIG. 13A for the ability to inhibit HCV IRES-mediated gene expression in 293FT cells. Experiments were conducted as for those of FIG. 10. shRNA concentration, 1 nM. (shRNA sequences are listed in FIG. 16A-B)

Additional experiments were performed to test how shRNA design affects gene silencing activity. HCVa-wt contained a 25 base pair stem with 5'-GG and 3'-UU overhangs (which may form non-canonical base pairs) and a ten nucleotide miR-23 loop. To test the importance of these parameters in the effectiveness for inhibition of expression, each of these parameters was separately varied (FIG. 13A). The microRNA-23 loop sequence was initially selected because it is a naturally occurring sequence (Lagos-Quintana et al., Science, 2001, 293:854-258) and was therefore unlikely to be toxic. Two alternative ten nucleotide loops were tested, along with loops of six nucleotides, five nucleotides, and four nucleotides, each in two versions of a sequence. Neither loop size nor sequence was found to affect the activity of these 25 base pair shRNAs (FIG. 13B; see FIG. 16A-B for sequences).

Small hairpin RNAs lacking the 3'-UU terminal sequence (single-stranded overhang) had the same efficacy as the parental shRNA containing this feature. Control shRNA with full-length (25 nucleotide) sense but short (13 nucleotide) antisense regions had no activity, confirming the importance of duplex structure in the targeting sequence. shRNAs having a 3'-CC instead of 3'-UU terminus (allowing formation of 2 additional Watson-Crick base pairs) were more effective than HCVa-wt for decreasing HCV expression, but also affected SEAP levels. This nonspecific inhibition could be a consequence of the longer stem (27 base pairs), which can induce genes of the interferon responsive pathway and activate protein kinase R (PKR). Surprisingly, moving the loop to the other end of the shRNA resulted in a dramatic reduction of activity (15% inhibition at 1 nM instead of 90%). Possible explanations for this effect include a shift in the position of Dicer processing (and therefore the sequence targeted) as well as a different GC content at the 5'-end.

Figure 14:
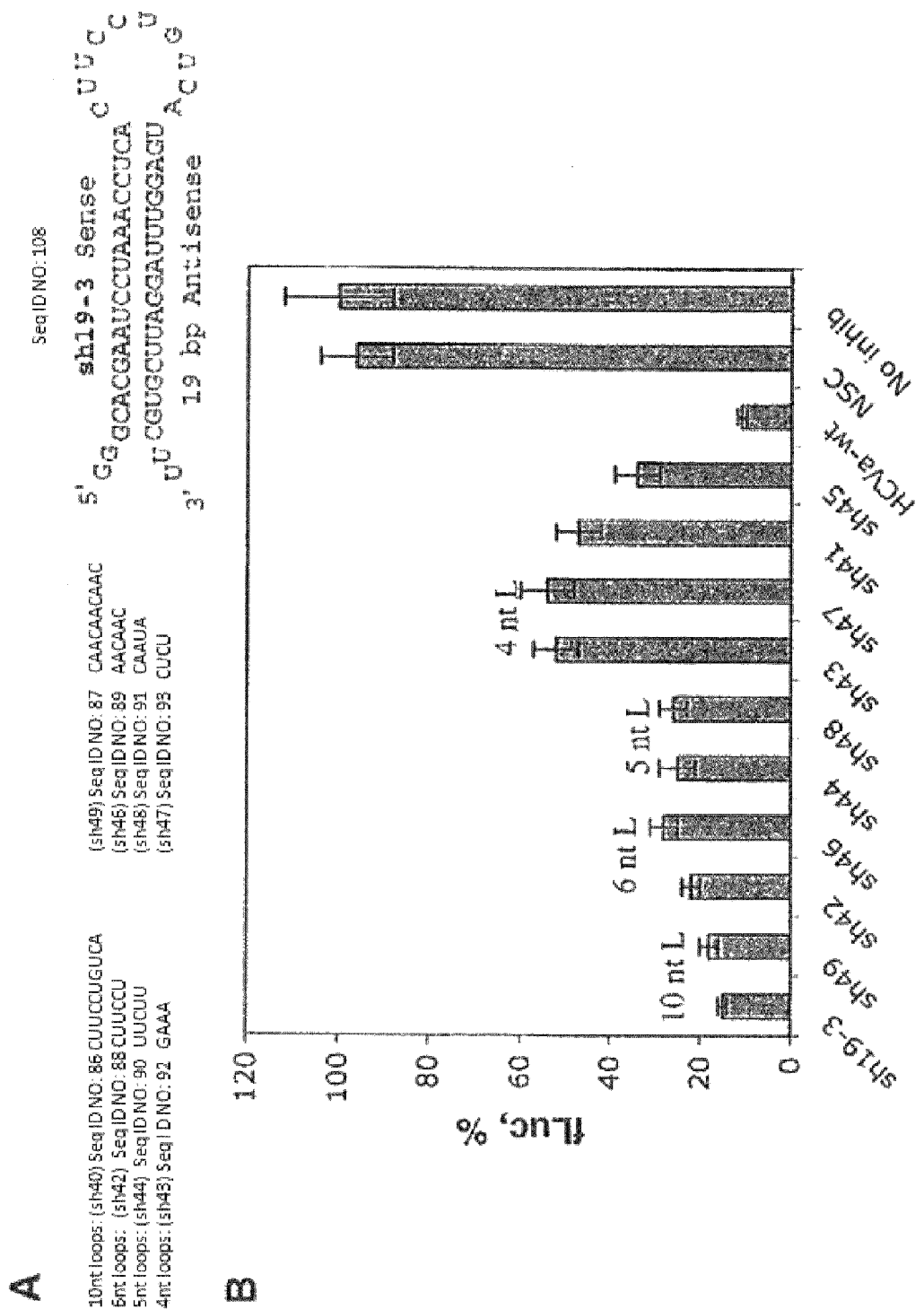
FIG. 14A is a diagrammatic representation of the sequences of tested variants of the depicted 19-bp shRNA with the various loop sizes and sequences tested, as well as 3' termini that were tested.
FIG. 14B is a bar graph depicting the results of a screen of shRNAs depicted in FIG. 14A for the ability to inhibit HCV IRES-mediated gene expression in 293FT cells. Experiments were conducted as described for FIG. 10. shRNA concentration, 1 nM. (shRNA sequences are listed in FIG. 16A-B)

Because 19 base pair shRNAs were shown to display potency similar to 25 base pair shRNA, the effects of loop variations for 19 base pair shRNAs were examined. The results are shown in FIG. 14; see FIG. 16A-B for sequences. Loop sizes of 10, 6, 5, and 4 nucleotides were tested, each in two sequence versions. Sequences containing all loop sizes demonstrated the ability to inhibit gene expression. However, in contrast to the results with 25 base pair shRNAs, reduction of loop size, especially below 5 nucleotides, resulted in reduced activity for the 19 base pair shRNAs for both loop sequences tested. Loops of at least 5-6 nucleotides demonstrated the most activity.

Removal of the 3'-UU also resulted in dramatic reduction of activity for 19 base pair as well as 20 base pair (but not 25 base pair) shRNAs. Without committing to any particular theory, the 3'-UU and 5'-GG may form non-canonical base pairs and the overall size of shRNA duplex is important such that the duplex cannot be less than 21 base pairs for efficient processing. Thus, for 25 base pair shRNAs, neither the size of the loop nor the presence of a 3'-UU matters, whereas these parameters are important for potency of short, e.g., 19 base pair shRNAs. Without committing to any particular theory, it may be that Dicer binds at the termini prior to processing and does not "sense" the loop in the case of longer shRNAs, but for 19 base pair shRNAs the loop is "felt" as Dicer "measures" 19-21 nucleotides from the ends.

Accordingly, it was found that 19 base pair shRNAs can be as potent as 25 base pair shRNAs and 19 base pair siRNA. It was also found that some shRNA molecules were active at low concentrations of 0.1-1 nM ("hyper-potent shRNAs." Other groups typically use 10-25-50-100 nM siRNA).

These data demonstrate that sequences that do not include a 3'-UU that are at least 22 base pairs, e.g., 23 base pairs, 24 base pairs, or 25 base pairs, can be suitable for inhibition of HCV expression. Similarly, loop size is not critical for shRNAs that are at least 22 base pairs in length.

Example 9

HCV Replicon System

Figure 15:
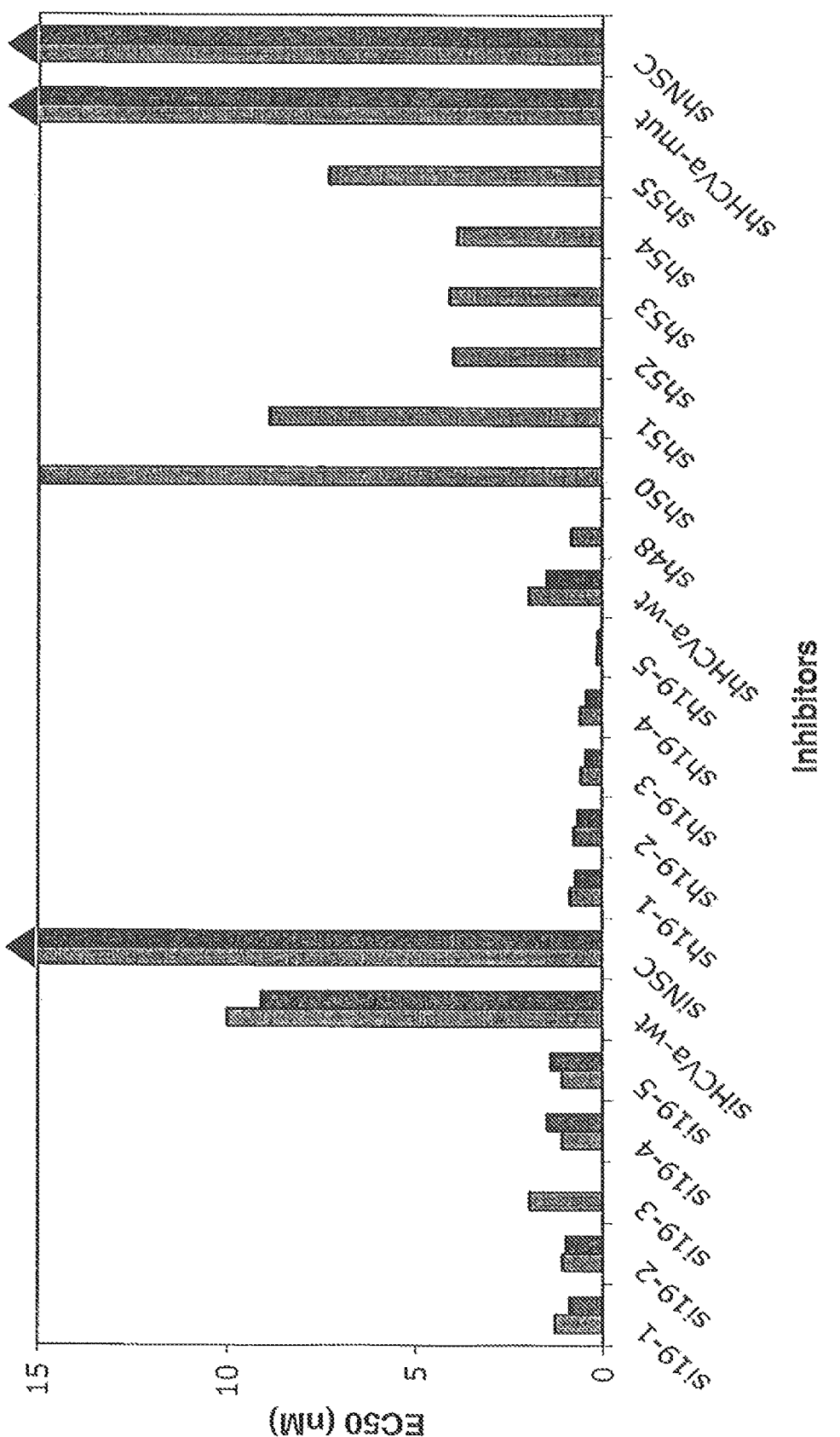
FIG. 15 is a bar graph depicting the results of a screen of shRNAs (and siRNAs) for the inhibitory activity in the HCV replicon system. Human hepatocytes (AVA5, a derivative of the Huh7 cell line) stably expressing HCV subgenomic replicons, were transfected with RNA inhibitors, and the amount of HCV expression was determined. A range of concentrations was tested and the concentration of sh/siRNA that resulted in 50% inhibition (EC50) was determined. Dark and light bars represent the results of two independent experiments.

A number of shRNA and siRNA inhibitors along with negative controls were used to transfect human hepatocytes (AVA5, a derivative of the Huh7 cell line) stably expressing HCV subgenomic replicons (Blight et al., Science, 2000, 290:5498), and the amount of HCV expression was determined. A range of concentrations was tested and the concentration of RNA resulting in 50% inhibition (IC50 or EC50) was determined. IC50s from two independent experiments are shown side-by-side in FIG. 15. The results generally correlated with the data obtained using the fLuc/IRES system in 293 FT cells, with the following differences: (1) 19 base pair shRNAs are more potent than 19 base pair siRNAs in the replicon system, whereas with the reporter system, 19 base pair siRNAs were more potent than shRNAs; (2) shRNA HCVa-wt with point mutations did not demonstrate activity in the replicon system, while it was effective in fLuc/IRES reporter system; (3) in general, 25 base pair siRNA and 25 base pair shRNA had less activity than other 19 base pair shRNAs and siRNAs tested. In general, the IRES and replicon systems are useful for identification of candidate sequences. Methods of confirming the efficacy (e.g., for inhibiting expression of HCV in a subject) of a selected shRNA or siRNA can be further tested using methods described herein and methods known in the art.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Sookoian, S. C., *New therapies on the horizon for hepatitis C*. Ann Hepatol, 2003. 2: 164-70.
2. Randall, G. and C. M. Rice, *Interfering with hepatitis C virus RNA replication*. Virus Res, 2004. 102: 19-25.
3. Radhakrishnan, S. K., T. J. Layden, and A. L. Gartel, *RNA interference as a new strategy against viral hepatitis*. Virology, 2004. 323: 173-81.

4. Hugle, T. and A. Cerny, *Current therapy and new molecular approaches to antiviral treatment and prevention of hepatitis C*. Rev Med Virol, 2003. 13: 361-71.
5. Blight, K. J., A. A. Kolykhalov, and C. M. Rice, *Efficient initiation of HCV RNA replication in cell culture*. Science, 2000. 290: 1972-4.
6. Pietschmann, T. and R. Bartenschlager, *Tissue culture and animal models for hepatitis C virus*. Clin Liver Dis, 2003. 7: 23-43.
7. Mercer, D. F., D. E. Schiller, J. F. Elliott, D. N. Douglas, C. Hao, A. Rinfret, W. R. Addison, K. P. Fischer, T. A. Churchill, J. R. Lakey, D. L. Tyrrell, and N. M. Kneteman, *Hepatitis C virus replication in mice with chimeric human livers*. Nat Med, 2001. 7: 927-33.
8. McCaffrey, A. P., L. Meuse, M. Karimi, C. H. Contag, and M. A. Kay, *A potent and specific morpholino antisense inhibitor of hepatitis C translation in mice*. Hepatology, 2003. 38: 503-8.
9. Lieberman, J., E. Song, S. K. Lee, and P. Shankar, *Interfering with disease: opportunities and roadblocks to harnessing RNA interference*. Trends Mol Med, 2003. 9: 397-403.
10. Layzer, J. M., A. P. McCaffrey, A. K. Tanner, Z. Huang, M. A. Kay, and B. A. Sullenger, *In vivo activity of nuclease-resistant siRNAs*. Rna, 2004. 10: 766-71.
11. Rossi, J. J. and G. J. Hannon, *Unlocking the potential of the human genome with RNA interference*. Nature, 2004. 431: 35-43.
12. McHutchison, J. G. and K. Patel, *Future therapy of hepatitis C*. Hepatology, 2002. 36: S245-52.
13. Wilson, J. A., S. Jayasena, A. Khvorova, S. Sabatinos, I. G. Rodrigue-Gervais, S. Arya, F. Sarangi, M. Harris-Brandts, S. Beaulieu, and C. D. Richardson, *RNA interference blocks gene expression and RNA synthesis from hepatitis C replicons propagated in human liver cells*. Proc Natl Acad Sci USA, 2003. 100: 2783-8.
14. Randall, G., A. Grakoui, and C. M. Rice, *Clearance of replicating hepatitis C virus replicon RNAs in cell culture by small interfering RNAs*. Proc Natl Acad Sci USA, 2003. 100: 235-40.
15. Yokota, T., N. Sakamoto, N. Enomoto, Y. Tanabe, M. Miyagishi, S. Maekawa, L. Yi, M. Kurosaki, K. Taira, M. Watanabe, and H. Mizusawa, *Inhibition of intracellular hepatitis C virus replication by synthetic and vector-derived small interfering RNAs*. EMBO Rep, 2003. 4: 602-8.
16. Kapadia, S. B., A. Brideau-Andersen, and F. V. Chisari, *Interference of hepatitis C virus RNA replication by short interfering RNAs*. Proc Natl Acad Sci USA, 2003. 100: 2014-8.
17. Kronke, J., R. Kittler, F. Buchholz, M. P. Windisch, T. Pietschmann, R. Bartenschlager, and M. Frese, *Alternative approaches for efficient inhibition of hepatitis C virus RNA replication by small interfering RNAs*. J Virol, 2004. 78: 3436-46.
18. Sen, A., R. Steele, A. K. Ghosh, A. Basu, R. Ray, and R. B. Ray, *Inhibition of hepatitis C virus protein expression by RNA interference*. Virus Res, 2003. 96: 27-35.
19. Zhang, J., O. Yamada, T. Sakamoto, H. Yoshida, T. Iwai, Y. Matsushita, H. Shimamura, H. Araki, and K. Shimotohno, *Down-regulation of viral replication by adenoviral-mediated expression of siRNA against cellular cofactors for hepatitis C virus*. Virology, 2004. 320: 135-43.
20. McCaffrey, A. P., L. Meuse, T. T. Pham, D. S. Conklin, G. J. Hannon, and M. A. Kay, *RNA interference in adult mice*. Nature, 2002. 418: 38-9.
21. Kawasaki, H. and K. Taira, *Short hairpin type of dsRNAs that are controlled by tRNA(Val) promoter significantly induce RNAi-mediated gene silencing in the cytoplasm of human cells*. Nucleic Acids Res, 2003. 31: 700-7.
22. Lagos-Quintana, M., R. Rauhut, W. Lendeckel, and T. Tuschl, *Identification of novel genes coding for small expressed RNAs*. Science, 2001. 294: 853-8.
23. Qin, X. F., D. S. An, I. S. Chen, and D. Baltimore, *Inhibiting HIV-1 infection in human T cells by lentiviral-mediated delivery of small interfering RNA against CCR5*. Proc Natl Acad Sci USA, 2003. 100: 183-8.
24. McCaffrey, A. P., K. Ohashi, L. Meuse, S. Shen, A.M. Lancaster, P. J. Lukaysky, P. Sarnow, and M. A. Kay, *Determinants of hepatitis C translational initiation in vitro, in cultured cells and mice*. Mol Ther, 2002. 5: 676-84.
25. Seo, M. Y., S. Abrignani, M. Houghton, and J. H. Han, *Small interfering RNA-mediated inhibition of hepatitis C virus replication in the human hepatoma cell line Huh-7*. J Virol, 2003. 77: 810-2.
26. Kim, D. H., M. Longo, Y. Han, P. Lundberg, E. Cantin, and J. J. Rossi, *Interferon induction by siRNAs and ssRNAs synthesized by phage polymerase*. Nat Biotechnol, 2004. 22: 321-5.
27. Bridge, A. J., S. Pebernard, A. Ducraux, A. L. Nicoulaz, and R. Iggo, *Induction of an interferon response by RNAi vectors in mammalian cells*. Nat Genet, 2003. 34: 263-4.
28. Fish, R. J. and E. K. Kruithof, *Short-term cytotoxic effects and long-term instability of RNAi delivered using lentiviral vectors*. BMC Mol Biol, 2004. 5: 9.
29. Han, J. H., V. Shyamala, K. H. Richman, M. J. Brauer, B. Irvine, M. S. Urdea, P. Tekamp-Olson, G. Kuo, Q. L. Choo, and M. Houghton, *Characterization of the terminal regions of hepatitis C viral RNA: identification of conserved sequences in the 5' untranslated region and poly(A) tails at the 3' end*. Proc Natl Acad Sci USA, 1991. 88: 1711-5.
30. Choo, Q. L., K. H. Richman, J. H. Han, K. Berger, C. Lee, C. Dong, C. Gallegos, D. Coit, R. Medina-Selby, P. J. Barr, and et al., *Genetic organization and diversity of the hepatitis C virus*. Proc Natl Acad Sci USA, 1991. 88: 2451-5.
31. Okamoto, H., S. Okada, Y. Sugiyama, K. Kurai, H. Iizuka, A. Machida, Y. Miyakawa, and M. Mayumi, *Nucleotide sequence of the genomic RNA of hepatitis C virus isolated from a human carrier: comparison with reported isolates for conserved and divergent regions*. J Gen Virol, 1991. 72 (Pt 11): 2697-704.
32. Bukh, J., R. H. Purcell, and R. H. Miller, *Sequence analysis of the 5' noncoding region of hepatitis C virus*. Proc Natl Acad Sci USA, 1992. 89: 4942-6.
33. Rice, C. M., *Virology: fresh assault on hepatitis C*. Nature, 2003. 426: 129-31.
34. Zhang, H., R. Hanecak, V. Brown-Driver, R. Azad, B. Conklin, M. C. Fox, and K. P. Anderson, *Antisense oligonucleotide inhibition of hepatitis C virus (HCV) gene expression in livers of mice infected with an HCV-vaccinia virus recombinant*. Antimicrob Agents Chemother, 1999. 43: 347-53.
35. Jubin, R., N. E. Vantuno, J. S. Kieft, M. G. Murray, J. A. Doudna, J. Y. Lau, and B. M. Baroudy, *Hepatitis C virus internal ribosome entry site (IRES) stem loop IIId contains a phylogenetically conserved GGG triplet essential for translation and IRES folding*. J Virol, 2000. 74: 10430-7.
36. Seyhan A A, Vlassov A V, Ilves H, Egry L, Kaspar R L, Kazakov S A, Johnston B H. *Complete, gene-specific siRNA libraries: production and expression in mammalian cells*. RNA. 2005. 11:837-46.
37. Wang Q, Contag C H, Ilves H, Johnston B H, Kaspar R L. *Small hairpin RNAs efficiently inhibit hepatitis C IRES-mediated gene expression in human tissue culture cells and a mouse model*. Mol Ther. 2005. 12:562-8

We claim:

1. A method of inhibiting hepatitis C virus (HCV) RNA replication or gene expression in a cell, comprising introducing a small interfering RNA into an HCV-containing cell, wherein the antisense sequence of said small interfering RNA consists of a sequence that recognizes a sequence of 19 to 25 nucleotides within the region depicted in nucleotides 344-368 of SEQ ID NO: 11, wherein said antisense sequence is selected from the group consisting of SEQ ID NO:21, SEQ ID NO:22, SEQ ID NO: 23, and SEQ ID NO:24 and the antisense sequence of SEQ ID NO: 12, and wherein said small interfering RNA inhibits HCV RNA replication or gene expression in the cell.

2. A method according to claim 1, wherein said small interfering RNA is an shRNA.

3. A method according to claim 1, wherein said small interfering RNA is an siRNA.

4. A method according to claim 1, wherein said hepatitis C virus is genotype 1a.

5. A method of treating a hepatitis C virus (HCV) infection in a mammal, said method comprising administering to said mammal a composition comprising a therapeutically effective amount of a small interfering RNA wherein the antisense sequence of said small interfering RNA consists of a sequence that recognizes a sequence of 19 to 25 nucleotides within the region depicted in nucleotides 344-368 of SEQ ID NO:11, wherein said antisense sequence is selected from the group consisting of SEQ ID NO:21, SEQ ID NO:22, SEQ ID NO: 23, and SEQ ID NO:24 and the antisense sequence of SEQ ID NO: 12, and wherein said small interfering RNA inhibits HCV RNA replication or gene expression in said mammal, thereby treating HCV infection in said mammal.

6. A method according to claim 1, wherein said small interfering RNA is an shRNA.

7. A method according to claim 1, wherein said small interfering RNA is an siRNA.

8. A method according to claim 1, wherein said hepatitis C virus is genotype 1a.

9. A method according to claim 1, wherein said mammal is a human.

10. A composition comprising a small interfering RNA, wherein the antisense sequence of said small interfering RNA consists of a sequence that recognizes a sequence of 19 to 25 nucleotides within the region depicted in nucleotides 344-368 of SEQ ID NO:11, wherein said antisense sequence is selected from the group consisting of SEQ ID NO:21, SEQ ID NO:22, SEQ ID NO: 23, and SEQ ID NO:24 and the antisense sequence of SEQ ID NO: 12.

11. A composition according to claim 10, wherein said small interfering RNA is an shRNA.

12. A composition according to claim 10, wherein said small interfering RNA is an siRNA.

13. A composition according to claim 10, wherein said composition is a pharmaceutical composition, said pharmaceutical composition further comprising a pharmaceutically acceptable excipient.

14. A kit comprising a small interfering RNA, wherein the antisense sequence of said small interfering RNA consists of a sequence that recognizes a sequence of 19 to 25 nucleotides within the region depicted in nucleotides 344-368 of SEQ ID NO:11, wherein said antisense sequence is selected from the group consisting of SEQ ID NO:21, SEQ ID NO:22, SEQ ID NO: 23, and SEQ ID NO:24 and the antisense sequence of SEQ ID NO: 12.

15. A kit according to claim 14, wherein said small interfering RNA is an shRNA.

16. A kit according to claim 14, wherein said small interfering RNA is an siRNA.

* * * * *